US012704477B2

(12) United States Patent
Choi et al.

(10) Patent No.: US 12,704,477 B2
(45) Date of Patent: Aug. 11, 2026

(54) BIOSENSOR DIAGNOSTIC DEVICE AND BIOSENSOR SYSTEM INCLUDING THE SAME

(71) Applicant: LG ELECTRONICS INC., Seoul (KR)

(72) Inventors: Taekyu Choi, Seoul (KR); Changseok Kim, Seoul (KR); Kyungho Kong, Seoul (KR); Kyoungtaek Lim, Seoul (KR); Inkwan Yeo, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 728 days.

(21) Appl. No.: 18/091,162

(22) Filed: Dec. 29, 2022

(65) Prior Publication Data

US 2023/0329573 A1 Oct. 19, 2023

(30) Foreign Application Priority Data

Apr. 19, 2022 (KR) ........................ 10-2022-0047913

(51) Int. Cl.
*A61B 5/05* (2021.01)
*A61B 10/00* (2006.01)
(Continued)

(52) U.S. Cl.
CPC ........... *G01N 27/4145* (2013.01); *A61B 5/05* (2013.01); *A61B 10/0045* (2013.01);
(Continued)

(58) Field of Classification Search
CPC ............. G01N 27/4145; G01N 27/414; G01N 33/48785; G01N 33/5438;
(Continued)

(56) References Cited

U.S. PATENT DOCUMENTS 9,805,165 B2 10/2017 Xiang et al.
11,342,051 B1 5/2022 Jain et al.
(Continued)

FOREIGN PATENT DOCUMENTS

CA 3175822 A1 10/2021
JP 2000-258493 A 9/2000
(Continued)

OTHER PUBLICATIONS

Cheah et al., "Integrated Platform Addressing the Finger-Prick Blood Processing Challenges of Point-of-Care Electrical Biomarker Testing", Analytical Chemistry, vol. 94, No. 1, published Jan. 3, 2022, pp. 1256-1263.

(Continued)

*Primary Examiner* — Charles Capozzi
*Assistant Examiner* — Michael Stanley Gzybowski
(74) *Attorney, Agent, or Firm* — Birch, Stewart, Kolasch & Birch, LLP

(57) ABSTRACT

A biosensor diagnostic device can include an interface configured to receive an electrical signal from a biosensor cartridge in response to being connected to a connection terminal of the biosensor cartridge; an image reader configured to capture a code image on the biosensor cartridge. And a signal processor configured to process a signal received from the interface for generating diagnostic result information. Also, the biosensor diagnostic device can include a wireless transceiver configured to transmit information corresponding to the code image and the diagnostic result information to a server or an external terminal.

17 Claims, 30 Drawing Sheets

(51) Int. Cl.

| | |
|---|---|
| ***G01N 27/414*** | (2006.01) |
| ***G01N 33/487*** | (2006.01) |
| ***G01N 33/543*** | (2006.01) |
| ***G06K 7/14*** | (2006.01) |

(52) U.S. Cl.

CPC ..... *G01N 27/414* (2013.01); *G01N 33/48785* (2013.01); *G01N 33/5438* (2013.01); *B01L 2200/027* (2013.01); *B01L 2300/0636* (2013.01); *B01L 2300/0645* (2013.01); *B01L 2300/0663* (2013.01); *H01R 2201/20* (2013.01); *H05K 2201/10151* (2013.01)

(58) Field of Classification Search

CPC ....... G01N 33/48707; G01N 33/48771; G01N 33/48778; G01N 33/48792; G01N 27/4146; A61B 5/05; A61B 10/0045; A61B 5/0077; A61B 5/14546; A61B 5/1468; A61B 5/1486; A61B 5/4887; A61B 5/0002; A61B 5/061; A61B 2562/08; B01L 2200/027; B01L 2300/0636; B01L 2300/0645; B01L 2300/0663; B01L 3/502715; H01R 2201/20; H01R 13/465; H01R 13/6683; H01R 2201/12; H01R 12/72; H05K 2201/10151; H05K 2201/10265; H05K 1/181; H05K 2201/10166; H05K 2201/10386; G06K 7/1417; G06K 7/1447; G06Q 20/3223

See application file for complete search history.

(56) References Cited

U.S. PATENT DOCUMENTS

| | | | |
|---|---|---|---|
| 12,455,258 | B2 | 10/2025 | Kim et al. |
| 2004/0244151 | A1 | 12/2004 | Sakata et al. |
| 2008/0280285 | A1 | 11/2008 | Chen et al. |
| 2009/0124876 | A1 | 5/2009 | Nakamura et al. |
| 2014/0052475 | A1 | 2/2014 | Madan et al. |
| 2014/0273187 | A1* | 9/2014 | Johnson ............ G01N 27/3272 435/287.2 |
| 2014/0308459 | A1 | 10/2014 | Miyazaki et al. |
| 2015/0083589 | A1 | 3/2015 | Lee et al. |
| 2015/0268186 | A1 | 9/2015 | Pagels |
| 2015/0352550 | A1 | 12/2015 | Bhargava et al. |
| 2016/0084793 | A1 | 3/2016 | Chen et al. |
| 2018/0272342 | A1 | 9/2018 | Samsoondar |
| 2019/0041355 | A1 | 2/2019 | Merriman et al. |
| 2019/0234907 | A1 | 8/2019 | Edwards et al. |
| 2020/0108385 | A1 | 4/2020 | Temiz et al. |
| 2020/0170552 | A1 | 6/2020 | Cho et al. |
| 2020/0333286 | A1 | 10/2020 | Leon et al. |
| 2021/0003528 | A1 | 1/2021 | Esquivel-Upshaw et al. |
| 2021/0129133 | A1 | 5/2021 | Ohta et al. |
| 2021/0285977 | A1 | 9/2021 | Tu et al. |
| 2021/0365445 | A1 | 11/2021 | Robell et al. |

FOREIGN PATENT DOCUMENTS

| | | | |
|---|---|---|---|
| JP | 2003-149192 | A | 5/2003 |
| JP | 2008-46094 | A | 2/2008 |
| JP | 2013-83506 | A | 5/2013 |
| JP | 2020-126077 | A | 8/2020 |
| KR | 20-0311804 | Y1 | 5/2003 |
| KR | 10-0813398 | B1 | 3/2008 |
| KR | 10-2008-0110356 | A | 12/2008 |
| KR | 10-2010-0072533 | A | 7/2010 |
| KR | 10-2010-0103932 | A | 9/2010 |
| KR | 10-2011-0064754 | A | 6/2011 |
| KR | 10-2012-0101806 | A | 9/2012 |
| KR | 10-2013-0012744 | A | 2/2013 |
| KR | 10-1323373 | B1 | 10/2013 |
| KR | 10-2014-0120138 | A | 10/2014 |
| KR | 10-1507317 | B1 | 3/2015 |
| KR | 10-2016-0017684 | A | 2/2016 |
| KR | 10-1591379 | B1 | 2/2016 |
| KR | 10-2016-0065562 | A | 6/2016 |
| KR | 10-2016-0128542 | A | 11/2016 |
| KR | 10-1779705 | B1 | 9/2017 |
| KR | 10-2030272 | B1 | 10/2019 |
| KR | 10-2019-0136580 | A | 12/2019 |
| KR | 10-2021-0076854 | A | 6/2021 |
| KR | 10-2021-0151487 | A | 12/2021 |
| WO | WO 2019/208901 | A1 | 10/2019 |
| WO | WO 2021/013392 | A1 | 1/2021 |
| WO | WO 2021/224907 | A1 | 11/2021 |

OTHER PUBLICATIONS

Tran et al., “Toward Intraoperative Detection of Disseminated Tumor Cells in Lymph Nodes with Silicon Nanowire Field Effect Transistors”, ACS Nano, vol. 10, No. 2, published on Feb. 9, 2016, pp. 2357-2364.

Sommers et al., “Self-propelled water droplet movement on a laser-etched radial gradient copper surface,” Applied Thermal Engineering, vol. 173, No. 115226, 2020, pp. 1-12.

* cited by examiner

FIG. 4
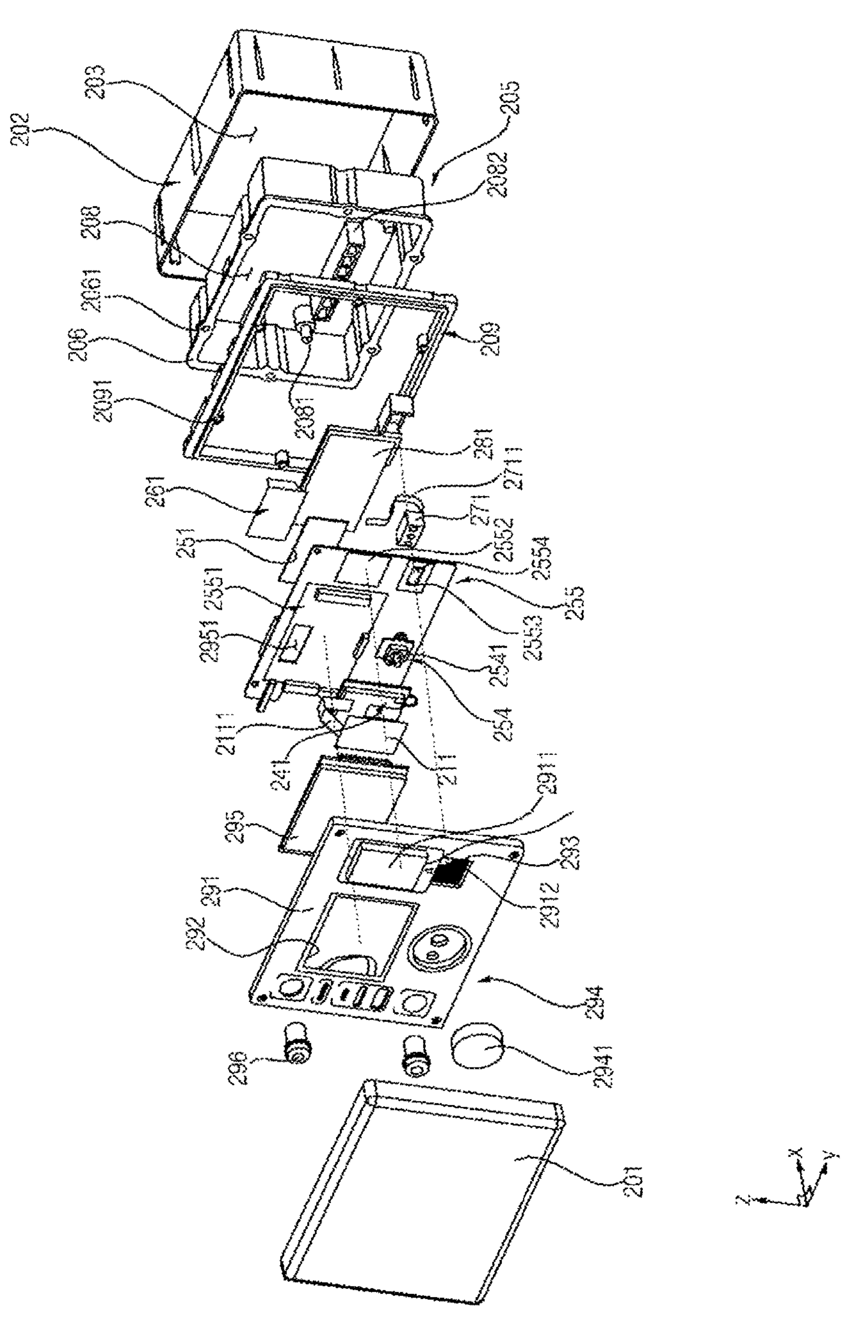

BIOSENSOR DIAGNOSTIC DEVICE AND BIOSENSOR SYSTEM INCLUDING THE SAME

CROSS-REFERENCE TO RELATED APPLICATION

This application claims priority to and the benefit of Korean Patent Application No. 10-2022-0047913, filed in the Republic of Korea on Apr. 19, 2022, the entirety of which is incorporated by reference into the present application.

BACKGROUND

1. Field of the Disclosure

This disclosure relates to a biosensor diagnostic device and a biosensor system including the same and, more specifically, to a biosensor diagnostic device capable of providing a diagnosis result promptly and accurately and a biosensor system including the same.

2. Description of the Related Art

Recently, as diseases having a high infectivity spread, a need for rapid diagnosis and self-diagnosis of the disease in medical fields, such as homes, hospitals, and public health centers, is increasing.

Therefore, it is desirable to develop an immunoassay platform that does not require specialized knowledge or complicated procedures and has a short analysis time.

A biosensor generates an electrical, optical signal, and a color that changes according to a selective reaction between probe material having reactivity for a specific target material contained in a body fluid such as sweat and saliva, or in biological substances such as blood or urine, and the target material. Accordingly, the presence of a specific target material can be checked by using the biosensor.

Conventionally, a strip-type rapid kit has been widely used, and simple color development is performed by determining whether a bio-target material having a certain concentration or higher is present.

However, in the situation of labeling the target material by color development, the conversion of color development may be inaccurate depending on the concentration of the target material, and the color development should be visually determined and can be hard to see or difficult to distinguish for a layperson. Therefore, the accuracy is different depending on the user who makes the determination.

To compensate for this, a biosensor that generates an electrical signal has been proposed.

In a biosensor that generates an electrical signal, a target material is coupled to a channel of a small thin film semiconductor structure, the electrical conductivity of the semiconductor structure is changed by the target material, and the target material is detected through a change in electrical conductivity.

In other words, when a target material is combined in a channel, if an electrochemical reaction occurs or the target material itself has a charge, electrons or holes in the semiconductor structure are accumulated or depleted due to the electric field effect caused by the combination of the probe material and the target material. Thus, the electrical conductivity is changed, which is read as a change in the amount of current.

In such an electrochemical-based biosensor, the resistance of an electrode itself and the interfacial property of a channel where the electrochemical reaction occurs are particularly important.

Meanwhile, in Korean Patent No. 10-2016-0128542, a biosensor using graphene is described only with respect to the attachment of a linker or a receptor for bonding probe material on an electrode of graphene, but application of the biosensor to a product is not described.

In addition, Korean Patent Publication No. 10-2016-0146513 describes a pattern of a sensor device and an electrode unit of a sensor itself, but such a biosensor is described to be directly attached to a human body and used. Accordingly, there is a problem in stability and reaction reliability.

SUMMARY OF THE DISCLOSURE

An object of the present disclosure is to provide a biosensor diagnostic device capable of providing a diagnosis result promptly and accurately and a biosensor system including the same.

Another object of the present disclosure is to provide a biosensor diagnostic device capable of providing a diagnosis result promptly and accurately regardless of receiving an electrical signal below a reference level and a biosensor system including the same.

Yet another object of the present disclosure is to provide a biosensor diagnostic device capable of promptly and accurately providing a diagnosis result regarding whether a plurality of target materials exist, and a biosensor system including the same.

Still another object of the present disclosure is to provide a biosensor diagnostic device capable of promptly and accurately providing a diagnosis result based on an electrical signal from different types of biosensor cartridges and a biosensor system including the same.

Yet still another object of the present disclosure is to provide a biosensor diagnostic device capable of promptly and accurately providing a diagnosis result based on an update and a biosensor system including the same.

To achieve the objects above, a biosensor diagnostic device according to one embodiment of the present disclosure comprises an interface configured to receive an electrical signal from a biosensor cartridge in response to a connection to a connection terminal of the biosensor cartridge, an image reader configured to capture a code image attached to the biosensor cartridge, a signal processor configured to process a signal received from the interface, and a wireless transceiver configured to transmit diagnostic result information output from the signal processor and information corresponding to the captured code image to a server or an external terminal.

Also, the signal processor can extract information corresponding to the code image from the code image captured by the image reader, transmit information corresponding to the code image to the server, and transmit diagnostic result information to the server or the external terminal in response to authentication information being received from the server.

In accordance with an aspect of the present disclosure, the signal processor can extract information corresponding to the code image from the code image captured by the image reader and transmit information corresponding to the code image to the server; and in response to authentication information being received from the server, the interface can supply an electrical signal of a first level to the biosensor cartridge through the interface during a first period and receive an electrical signal of a second level from the biosensor cartridge during a second period after the first period.

In addition, the signal processor can diagnose the existence of a target material based on a level difference between an electrical signal of the first level and an electrical signal of the second level or an electrical signal of the second level and output the diagnostic result information.

In accordance with an aspect of the present disclosure, in response to the level of an electrical signal received from the biosensor cartridge being less than or equal to a reference level during the second period, the signal processor can supply an electrical signal of the first level to the biosensor cartridge through the interface during a third period and receive an electrical signal from the biosensor cartridge during a fourth period after the third period.

In accordance with an aspect of the present disclosure, in response to the level of an electrical signal received from the biosensor cartridge being less than or equal to a reference level during the second period, the signal processor can supply an electrical signal of a third level larger than the first level to the biosensor cartridge through the interface during the third period, receive an electrical signal from the biosensor cartridge during the fourth period after the third period, diagnose the existence of a target material based on the electrical signal received during the fourth period, and output the diagnostic result information.

In addition, the signal processor can supply an electrical signal of the third level larger than the first level through the interface during the third period after receiving update data from the server, receive an electrical signal from the biosensor cartridge during the fourth period after the third period, diagnose the existence of a target material based on the electrical signal received during the fourth period, and output the diagnostic result information.

In accordance with an aspect of the present disclosure, the signal processor can extract information corresponding to the code image from the code image captured by the image reader and transmit the information corresponding to the code image to the server; and the interface can supply electrical signals of multiple levels sequentially to the biosensor cartridge through the interface during the first period in response to authentication information being received from the server and sequentially receive electrical signals of multiple levels from the biosensor cartridge during the second period after the first period.

In addition, the signal processor can diagnose the existence of a plurality of target materials based on a level difference between the multi-level electrical signal during the first period and the multi-level electrical signal during the second period or the multi-level electrical signal during the second period and output the diagnostic result information.

Also, the signal processor can diagnose the existence of a first target material by receiving an electrical signal from a first biosensor cartridge in response to the interface being coupled to a connection terminal of the first biosensor cartridge and output first diagnostic result information; and diagnose the existence of a second target material by receiving an electrical signal from a second biosensor cartridge in response to the interface being coupled to a connection terminal of the second biosensor cartridge and output second diagnostic result information.

In accordance with an aspect of the present disclosure, in response to the interface being coupled to a connection terminal of the first biosensor cartridge, the signal processor can supply an electrical signal of the first level to the first biosensor cartridge; and in response to the interface being coupled to a connection terminal of the second biosensor cartridge, the signal processor can supply an electrical signal of the first level to the second biosensor cartridge.

In accordance with an aspect of the present disclosure, in response to the interface being coupled to a connection terminal of the first biosensor cartridge, the signal processor can receive an electrical signal from the first biosensor cartridge, diagnose the existence of a first target material, and output first diagnostic result information; and in response to the interface being coupled to a connection terminal of the second biosensor cartridge, the signal processor can receive an electrical signal from the second biosensor cartridge, diagnose the existence of a second target material, and output second diagnostic result information.

In accordance with an aspect of the present disclosure, in response to the interface being coupled to a connection terminal of the first biosensor cartridge, the signal processor can supply an electrical signal of the first level to the first biosensor cartridge; and in response to the interface being coupled to a connection terminal of the second biosensor cartridge, the signal processor can supply an electrical signal of the second level different from the first level to the second biosensor cartridge.

Also, the signal processor can extract information on the type of target material from a code image attached to the biosensor cartridge and output an electrical signal of a level changed based on the type of the target material through the interface.

In addition, the signal processor can receive update data from the server and, based on receiving the update data, change the level of an electrical signal supplied to the biosensor cartridge or change the number of levels of a plurality of electrical signals supplied to the biosensor cartridge through the interface.

To achieve the objects above, a biosensor system according to one embodiment of the present disclosure comprises a biosensor cartridge, an interface configured to receive an electrical signal from the biosensor cartridge in response to a connection to a connection terminal of the biosensor cartridge, and a biosensor diagnostic device, in which the biosensor diagnostic device comprises an image reader configured to capture a code image attached to the biosensor cartridge, a signal processor configured to process a signal received from the interface, and a wireless transceiver configured to transmit diagnostic result information output from the signal processor and information corresponding to the captured code image to a server or an external terminal.

Effects of the Disclosure

A biosensor diagnostic device according to one embodiment of the present disclosure comprises an interface configured to receive an electrical signal from a biosensor cartridge in response to a connection to a connection terminal of the biosensor cartridge, an image reader configured to capture a code image attached to the biosensor cartridge, a signal processor configured to process a signal received from the interface, and a wireless transceiver configured to transmit diagnostic result information output from the signal processor and information corresponding to the captured code image to a server or an external terminal. Accordingly, a diagnosis result can be provided promptly and accurately.

In addition, the signal processor can extract information corresponding to the code image from the code image captured by the image reader, transmit information corresponding to the code image to the server, and transmit diagnostic result information to the server or the external terminal in response to authentication information being received from the server. Accordingly, a diagnosis result can be provided promptly and accurately.

Also, the signal processor can extract information corresponding to the code image from the code image captured by the image reader and transmit information corresponding to the code image to the server; and in response to authentication information being received from the server, the interface can supply an electrical signal of a first level to the biosensor cartridge through the interface during a first period and receive an electrical signal of a second level from the biosensor cartridge during a second period after the first period. Accordingly, a diagnosis result can be provided promptly and accurately.

In accordance with an aspect of the present disclosure, the signal processor can diagnose the existence of a target material based on a level difference between an electrical signal of the first level and an electrical signal of the second level or an electrical signal of the second level and output diagnostic result information. Accordingly, a diagnosis result can be provided promptly and accurately.

In accordance with an aspect of the present disclosure, in response to the level of an electrical signal received from the biosensor cartridge being less than or equal to a reference level during the second period, the signal processor can supply an electrical signal of the first level to the biosensor cartridge through the interface during the third period and receive an electrical signal from the biosensor cartridge during a fourth period after the third period. Accordingly, a diagnosis result can be provided promptly and accurately even though an electrical signal having a level less than or equal to a reference level is received.

Also, in response to the level of an electrical signal received from the biosensor cartridge being less than or equal to a reference level during the second period, the signal processor can supply an electrical signal of a third level larger than the first level to the biosensor cartridge through the interface during the third period, receive an electrical signal from the biosensor cartridge during the fourth period after the third period, diagnose the existence of a target material based on the electrical signal received during the fourth period, and output the diagnostic result information. Accordingly, a diagnosis result can be provided promptly and accurately even though an electrical signal having a level less than or equal to a reference level is received.

In addition, the signal processor can supply an electrical signal of the third level larger than the first level through the interface during the third period after receiving update data from the server, receive an electrical signal from the biosensor cartridge during the fourth period after the third period, diagnose the existence of a target material based on an electrical signal received during the fourth period, and output diagnostic result information. Accordingly, a diagnosis result can be provided promptly and accurately based on the update.

In accordance with an aspect of the present disclosure, the signal processor can extract information corresponding to the code image from the code image captured by the image reader and transmit the information corresponding to the code image to the server; and the interface can supply electrical signals of multiple levels sequentially to the biosensor cartridge through the interface during the first period in response to authentication information being received from the server and sequentially receive electrical signals of multiple levels from the biosensor cartridge during the second period after the first period. Accordingly, a diagnosis result can be provided promptly and accurately.

Also, the signal processor can diagnose the existence of a plurality of target materials based on a level difference between the multi-level electrical signal during the first period and the multi-level electrical signal during the second period or the multi-level electrical signal during the second period and output the diagnostic result information. Accordingly, a diagnosis result on the existence of a plurality of target materials can be provided promptly and accurately.

In accordance with an aspect of the present disclosure, the signal processor can diagnose the existence of a first target material by receiving an electrical signal from a first biosensor cartridge in response to the interface being coupled to a connection terminal of the first biosensor cartridge and output first diagnostic result information; and diagnose the existence of a second target material by receiving an electrical signal from a second biosensor cartridge in response to the interface being coupled to a connection terminal of the second biosensor cartridge and output second diagnostic result information. Accordingly, a diagnosis result on the existence of the first target material can be provided promptly and accurately using a plurality of biosensor cartridges.

In accordance with an aspect of the present disclosure, in response to the interface being coupled to a connection terminal of the first biosensor cartridge, the signal processor can supply an electrical signal of the first level to the first biosensor cartridge; and in response to the interface being coupled to a connection terminal of the second biosensor cartridge, the signal processor can supply an electrical signal of the first level to the second biosensor cartridge. Accordingly, a diagnosis result can be provided promptly and accurately using a plurality of biosensor cartridges.

In accordance with an aspect of the present disclosure, in response to the interface being coupled to a connection terminal of the first biosensor cartridge, the signal processor can receive an electrical signal from the first biosensor cartridge, diagnose the existence of a first target material, and output first diagnostic result information; and in response to the interface being coupled to a connection terminal of the second biosensor cartridge, the signal processor can receive an electrical signal from the second biosensor cartridge, diagnose the existence of a second target material, and output second diagnostic result information. Accordingly, a diagnosis result on the existence of a plurality of target materials can be provided promptly and accurately using a plurality of biosensor cartridges.

In accordance with an aspect of the present disclosure, in response to the interface being coupled to a connection terminal of the first biosensor cartridge, the signal processor can supply an electrical signal of the first level to the first biosensor cartridge; and in response to the interface being coupled to a connection terminal of the second biosensor cartridge, the signal processor can supply an electrical signal of the second level different from the first level to the second biosensor cartridge. Accordingly, a diagnosis result can be provided promptly and accurately.

Also, the signal processor can extract information on the type of target material from a code image attached to the biosensor cartridge and output an electrical signal of a level changed based on the type of the target material through the interface. Accordingly, a diagnosis result on the existence of a plurality of target materials can be provided promptly and accurately using a plurality of biosensor cartridges.

In addition, the signal processor can receive update data from the server and, based on receiving the update data, change the level of an electrical signal supplied to the biosensor cartridge or change the number of levels of a plurality of electrical signals supplied to the biosensor cartridge through the interface. Accordingly, a diagnosis result can be provided promptly and accurately based on the update.

A biosensor system according to one embodiment of the present disclosure comprises a biosensor cartridge, an interface configured to receive an electrical signal from the biosensor cartridge in response to a connection to a connection terminal of the biosensor cartridge, and a biosensor diagnostic device, in which the biosensor diagnostic device comprises an image reader configured to capture a code image attached to the biosensor cartridge, a signal processor configured to process a signal received from the interface, and a wireless transceiver configured to transmit diagnostic result information output from the signal processor and information corresponding to the captured code image to a server or an external terminal. Accordingly, a diagnosis result can be provided promptly and accurately based on the update.

BRIEF DESCRIPTION OF THE DRAWINGS

The above and other objects, features and advantages of the present invention will be more apparent from the following detailed description in conjunction with the accompanying drawings, which are described as follows below.

FIG. 4 is an exploded perspective view of the biosensor diagnostic device of FIG. 3 according to an embodiment of the present disclosure.

FIGS. 12A, 12B and 12C are diagrams illustrating a contact angle of a solution according to a micropattern according to an embodiment of the present disclosure.

FIG. 14 is a cross-sectional view of the biosensor cartridge of FIG. 13 taken along line IV-IV' according to an embodiment of the present disclosure.

Figure 17B:
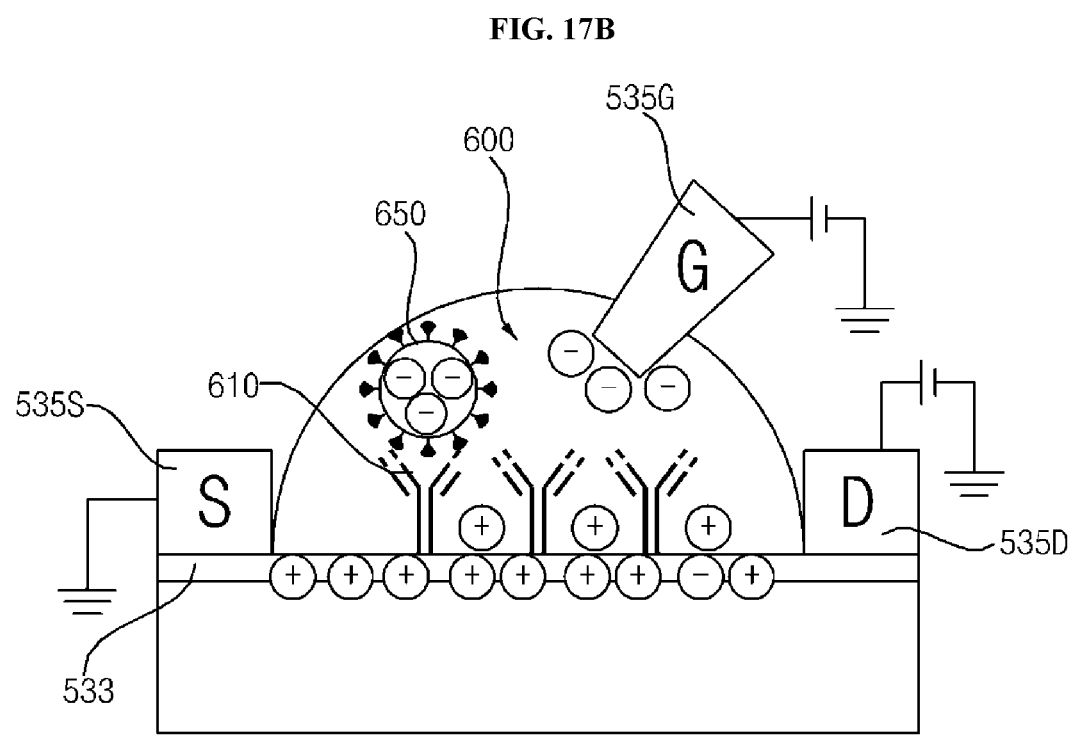

FIGS. 17A and 17B are schematic diagrams showing the response of the sensor chip of FIG. 15 according to target material, according to an embodiment of the present disclosure.

Figure 18:
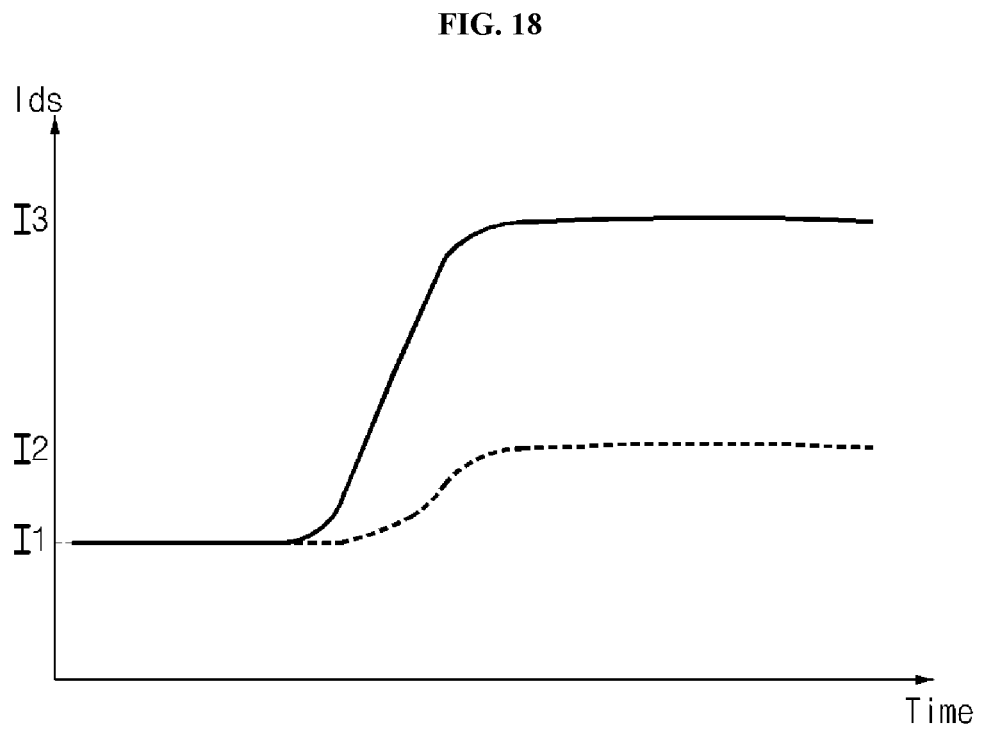

FIG. 18 is a graph showing a change in the output current of the sensor chip according to FIGS. 17A and 17B according to an embodiment of the present disclosure.

DETAILED DESCRIPTION OF THE EMBODIMENTS

In what follows, the present disclosure will be described in more detail with reference to appended drawings.

The suffixes "module" and "unit" for the constituting elements used in the following descriptions are assigned only for the convenience of writing the present disclosure and do not have separate meanings or roles distinguished from each other. Therefore, the "module" and "unit" can be used interchangeably.

In the present specification, target materials are biomaterials representing a specific substrate, and are interpreted as having the same meaning as analytical bodies or analytes. In the present embodiment, the target material can be an antigen. In the present specification, probe material is a biomaterial that specifically binds to a target material and is interpreted as having the same meaning as a receptor or an acceptor. In the present embodiment, the probe material can be an antibody.

The electrochemical-based biosensor combines the analytical ability of the electrochemical method with a specificity of biological recognition and detects a biological recognition phenomenon for a target material as a change in current or potential, by immobilizing or containing a material having biological specificity, e.g., probe material such as an enzyme, an antigen, an antibody, or a biochemical material, on the surface of an electrode.

Hereinafter, a biosensor system according to the present embodiment will be described with reference to FIGS. 1 and 2.

Figure 1:
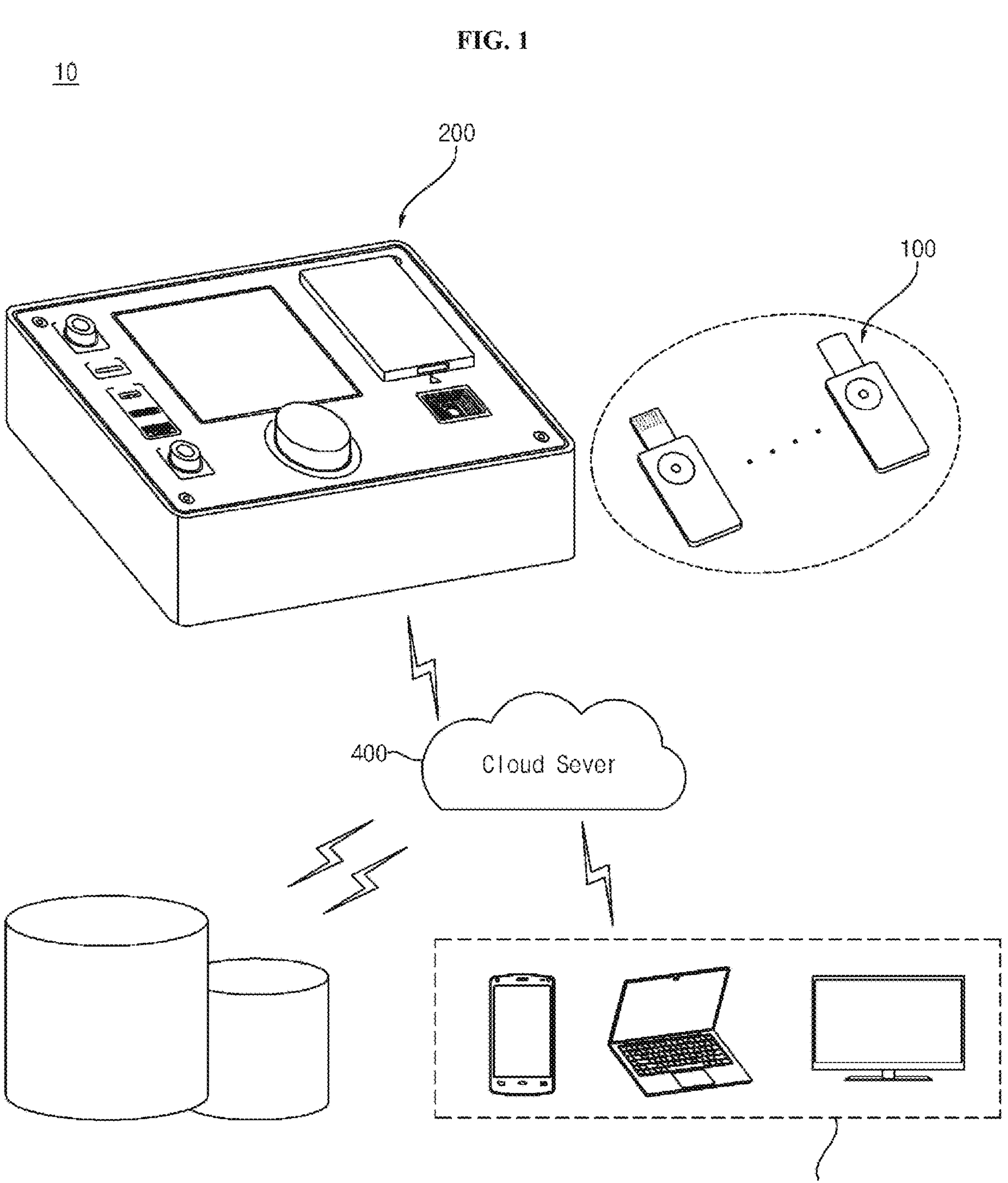
FIG. 1 is a diagram illustrating a biosensor system according to one embodiment of the present disclosure.
Figure 2:
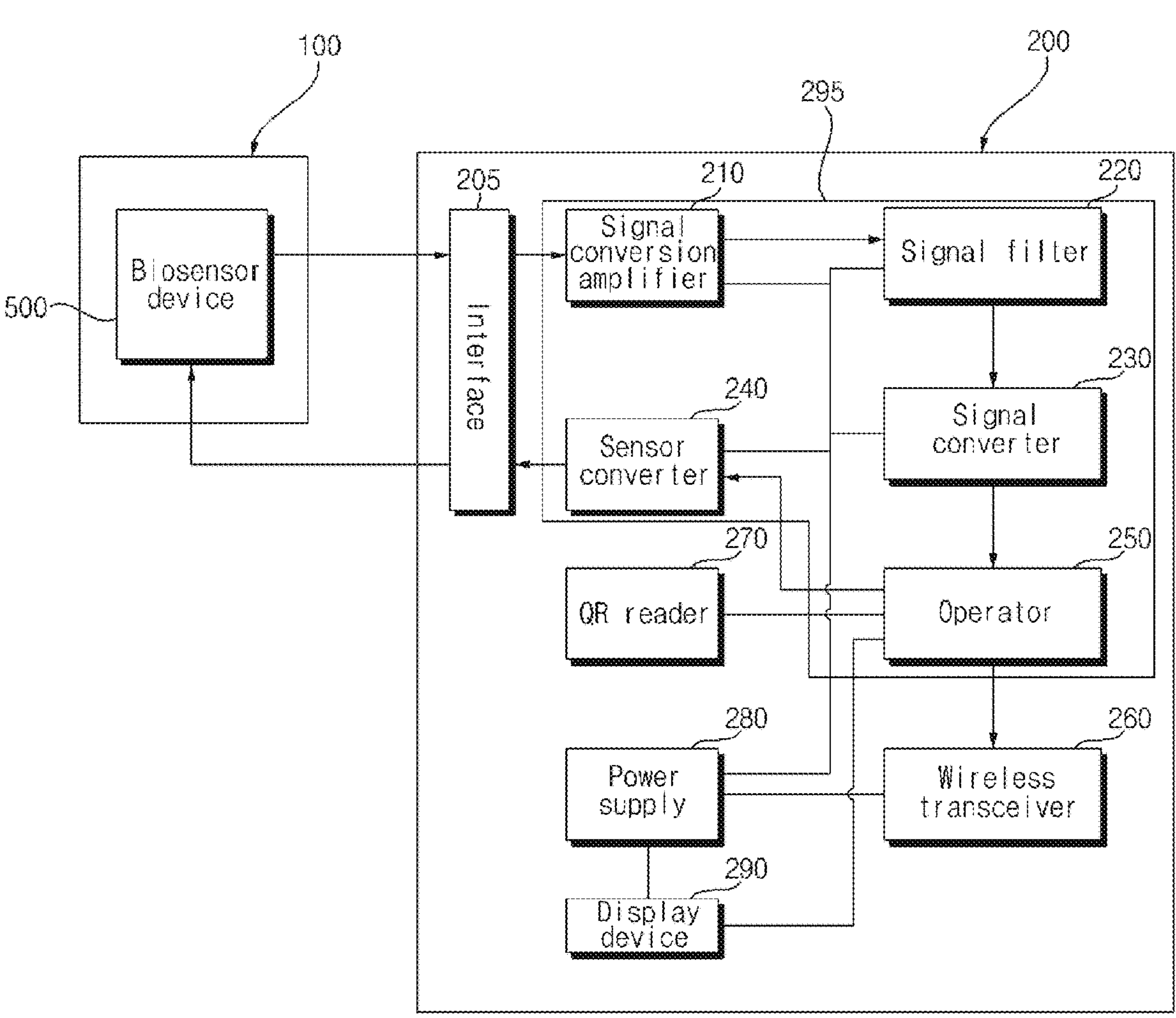
FIG. 2 is a configuration diagram of a biosensor diagnostic device and a biosensor cartridge of FIG. 1 according to an embodiment of the present disclosure.

FIG. 1 is a diagram illustrating a biosensor system 10 according to one embodiment of the present disclosure, and FIG. 2 is a configuration diagram of a biosensor diagnostic device 200 and a biosensor cartridge 100 of FIG. 1.

Referring to FIG. 1, the biosensor system 10 according to one embodiment of the present disclosure comprises a biosensor diagnostic device 200 and a plurality of biosensor cartridges 100.

Meanwhile, the biosensor system 10 according to one embodiment of the present disclosure further includes at least one server 400 and one or more external terminals 300.

When the plurality of biosensor cartridges 100 are inserted, the biosensor diagnostic device 200 reads a detection signal from the biosensor cartridge 100 to read the presence or the absence of a target material.

The biosensor diagnostic device 200 is a portable integrated diagnostic device 200, detects a current change for the presence of a trace amount of a target material from the biosensor cartridge 100, and accordingly diagnoses a disease and delivers a result to a user.

To this end, the biosensor diagnostic device 200 can be portable by integrating each functional block, miniaturizing it, and integrating it in one case or within one housing.

The biosensor diagnostic device 200 can be moved regardless of location, regardless of the presence or absence of an external power source by mounting a battery 281 therein. In addition, the diagnostic device 200 includes a function of compensating a reproducibility and non-uniformity of a sensor by including a pre-processing process of correcting a detection signal from the biosensor cartridge 100 to be able to read a minute signal change.

Also, the biosensor diagnostic device 200 can include a quick response (QR) reader capable of performing authentication by reading a code image such as a QR code disposed on the rear surface of the biosensor cartridge 100 to obtain environmental information for authenticating the biosensor cartridge 100 and a communication module capable of transmitting and receiving a signal for authentication to and from an external cloud server 400.

In the biosensor diagnostic device 200, a program algorithm or application for diagnosing a disease by measuring and analyzing the detection signal from the biosensor cartridge 100 can be installed, and different algorithms are executable based on the type of each biosensor cartridge 100.

In addition, the biosensor diagnostic device 200 includes a display device 290 for directly displaying the diagnosis result to a user and is designed to be directly manipulated through a user interface 296, 297, 294.

The detailed configuration of the integrated biosensor diagnostic device 200 will be described later.

Meanwhile, the biosensor system includes a plurality of biosensor cartridges 100 which is inserted into the biosensor diagnostic device 200 to provide detection signals.

Each of the biosensor cartridges 100 is electrically connected to a diagnostic device 200 in which an algorithm capable of measuring and analyzing an electrical detection signal generated in a biosensor chip 500 is installed.

Specifically, as shown in FIG. 1, the biosensor cartridge 100 can be inserted into and electrically connected to a cartridge insertion module 2911 of the integrated biosensor diagnostic device 200.

The biosensor cartridge 100 can accommodate the biosensor chip 500 corresponding to a biosensor device 500 in a housing 110, 120, and the housing 110, 120 can accommodate a circuit board 150 including a circuit pattern that extends to a connection terminal 153 that is connected to an electrode pad of the biosensor chip 500 and inserted into the insertion module 2911 of an external biosensor diagnostic device 200.

Figure 6:
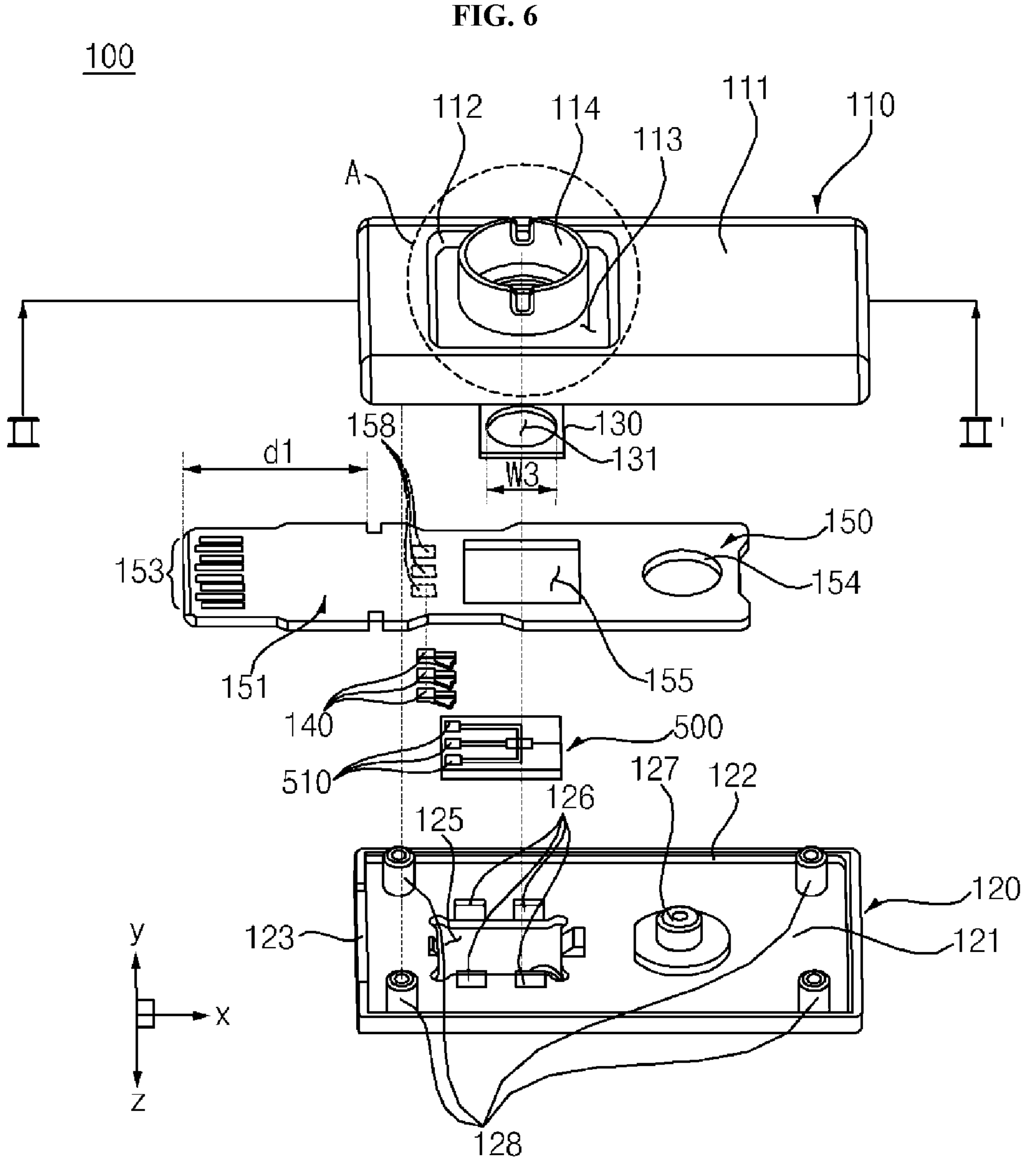
FIG. 6 is an exploded perspective view of an example of the biosensor cartridge of FIG. 1 according to an embodiment of the present disclosure.

The housing 110, 120 can be separated into an upper housing 110 and a lower housing 120, and the upper housing 110 and the lower housing 120 are coupled and fixed while accommodating the biosensor chip 500 and the circuit board, thereby constituting a single biosensor cartridge 100 (e.g., see FIG. 6).

The biosensor cartridge 100 has a connection terminal 153 for physical and electrical coupling with the biosensor diagnostic device 200 exposed from one end to the outside, and a solution accommodating portion 119 for accommodating a specimen is formed on the surface of the upper housing 110.

The solution accommodating portion 119 exposes an inner part of the inner sensor chip 500, and when a specimen is accommodated in the solution accommodating portion 119, the charge concentration of a channel of the biosensor chip 500 is varied according to the antigen-antibody reaction of the biosensor chip 500, so that the current flowing through the electrode of the biosensor chip 500 varies. The varied current is read by the diagnostic device 200 through the connection terminal 153.

In this situation, in order to secure the charge mobility of the biosensor chip 500, a channel can be implemented with various materials, and in particular, a channel can be implemented by using graphene.

The detailed configuration of the biosensor cartridge 100 will be described in detail later.

Meanwhile, the biosensor system can include at least one server 400.

The server 400 can be a manufacturer server 400, and the server 400 can include a processor capable of processing a program. The function of the server 400 can be performed by the manufacturer's central computer (cloud).

For example, the server 400 can be a server 400 operated by a manufacturer of the biosensor cartridge 100 and the diagnostic device 200. As another example, the server 400 can be a server 400 that is provided in a building, and stores state information on devices in the building or stores content required by home appliances in the building.

The server 400 can store firmware information and diagnostic information on the diagnostic device 200 and transmit certification information on the biosensor cartridge 100 requested from the diagnostic device 200.

The server 400 in a biosensor system can be one of a plurality of cloud servers 400 of a manufacturer and can be provided within the biosensor system while a plurality of cloud servers 400 are simultaneously included to allow access to one biosensor diagnostic device 200.

As described above, when a plurality of cloud servers 400 can simultaneously access one biosensor diagnostic device 200, the biosensor diagnostic device 200 can match the ranks with respect to the plurality of cloud servers 400 and can send a certification request sequentially from the highest priority. In this situation, if a response signal is not received from the priority server 400, a certification request can be sent to the server 400 of the next priority.

The server 400 can provide cartridge sensor information including a manufacturing history from the manufacturing stage of the biosensor cartridge 100 and sensor cartridge-specific information to the biosensor diagnostic device 200 as authentication information.

In addition, the server 400 can provide calibration data and update data for the product of a corresponding ID and can transmit to the communicating biosensor diagnostic device 200.

The server 400 can also generate and distribute an upgraded version of a program for analysis for each biosensor cartridge 100.

To this end, the server 400 can receive history information on the manufacturing date, manufacturing conditions, sensor type, test result, etc. of the biosensor cartridge 100 of a manufacturer from a manufacturing server of a separate manufacturer.

In addition, the server 400 can periodically generate and distribute an upgraded version of a program provided to each diagnostic device 200 by receiving, accumulating, and machine learning the diagnosis result values for a corresponding product.

Meanwhile, the biosensor system 10 of the present embodiment can further include a plurality of user terminals 300, but the present disclosure is not limited to the specific embodiment.

When the user terminal 300 is included in the system 10, the biosensor diagnostic device 200 or the cloud server 400 can transmit data related to a diagnosis result to the user terminal 300.

To this end, a dedicated application for the user terminal 300 can be provided from the manufacturer server 400, and various processing of diagnostic data is possible by storing and executing the application in the user terminal 300.

For example, when a user is infected with the same disease for a long period of time, data processing is possible so that periodic test results can be accumulated and displayed, and the processed results can be provided to the user terminal 300 through an application. Accordingly, the user terminal 300 can be able to determine the prognosis for the disease and the expected treatment time or expected recovery time.

The user terminal 300 can be, for example, a laptop, a smart phone, a tablet, or the like on which an application is installed.

The user terminal 300 can communicate directly with the diagnostic device 200 or the server 400 through a network, and the diagnostic device 200 and the server 400 can also communicate directly through a network.

In this situation, wireless communication technologies such as, IEEE 802.11 WLAN, IEEE 802.15 WPAN, UWB, Wi-Fi, ZIGBEE, Z-wave, and BLUETOOTH can be applied to the network and can include a wireless transceiver 260 of each device (the user terminal 300 and the diagnostic device 200) to apply at least one or more communication technologies.

The wireless transceiver 260 (e.g., wireless interface, or wireless communication unit) can be changed depending on the communication method of other devices (the user terminal 300 and the diagnostic device 200) or the server 400 that is a target to communicate with.

As described above, in the biosensor system, the connection terminal 153 of the biosensor cartridge 100 accommodating the specimen is inserted into and electrically connected to the portable integrated biosensor diagnostic device 200 so that a detection signal is read.

The functional configuration of the biosensor diagnostic device 200 for reading the detection signal is shown in FIG. 2.

Referring to FIG. 2, the biosensor diagnostic device 200 includes a plurality of function modules.

Each functional module can be individually packaged and accommodated in the situation of one biosensor diagnostic device 200, and a plurality of functional modules can be packaged as one module and accommodated in a case 201, 202.

The biosensor diagnostic device 200 includes a signal conversion amplifier 210, a signal filter 220, a signal converter 230, an operator 250, a wireless transceiver 260, a power supply 280, a display device 290, a Quick Response (QR) reader 270, and a sensor converter 240 (e.g., a sensor controller).

The signal conversion amplifier 210 first receives a detection signal transmitted from the biosensor cartridge 100 and converts and amplifies the current value of the detection signal so that the current value can be read by the biosensor diagnostic device 200.

The signal conversion amplifier 210 can have an analog circuit including a resistor that generates a voltage drop according to a changed current value which is a detection signal transmitted from the biosensor cartridge 100 and can further include an amplifying circuit that receives and amplifies such a voltage drop.

The amplified signal is transmitted to the signal filter 220 to remove noise and then transmitted to the signal converter 230. The signal converter 230 can convert the amplified analog sensing value from which the noise has been removed into a digital value for a diagnostic operation and can include an analog-digital converter (ADC) for this purpose.

As described above, the signal conversion amplifier 210, the signal filter 220, and the signal converter 230 can all be implemented as a single integrated circuit (IC) chip or one or more processors. Such an integrated circuit chip can correspond to a cartridge insertion module 2911 in FIG. 3.

The sensor converter 240 (e.g., sensor controller) can provide a reference voltage whose level is changed according to the control of the operator 250 to the connection terminal 153 of the connected biosensor cartridge 100, and the biosensor cartridge 100 receives a reference voltage having a varied level from the sensor converter 240 and flows a current value changed by a varied resistance value of a channel to the connection terminal 153. The sensor converter 240 can be mounted together as a voltage level conversion circuit in the integrated circuit chip.

Meanwhile, the biosensor diagnostic device 200 includes an operator 250 (e.g., operation controller) for controlling the operation of the diagnostic device 200 and reading a received digitized detection value.

The control of the diagnostic device 200 can include a separate controller, but it is possible to simultaneously read whether a detection value is detected and control the operation of the entire diagnostic device by executing a program stored in one controller or a processor.

In this situation, the operator 250 can be implemented as a separate integrated circuit chip and can be mounted in a main board 255.

The operator 250 can read whether there exists a target material for the detection value according to the reading program, process the result and provide the result to the display device 290. In addition, such a reading result can be transmitted to a cloud server 400 and a user terminal 300 through a wireless transceiver 260.

The operator 250 can also control the operation of the diagnostic device 200 for the reading of the result. For example, when the connection terminal 153 of the biosensor cartridge 100 is inserted into the cartridge insertion module 2911, the operator 250 can detect the insertion and transmit a QR reading command to the QR reader 270.

Accordingly, the QR reader 270 performs an operation for reading the QR code attached to the rear surface of the cartridge 100 inserted into the cartridge insertion module 211 and transmits the information back to the operator 250.

The operator 250 receives the QR information, performs a certification request to the cloud server 400 accordingly, and when certification information is received from the cloud server 400 and confirmed as genuine, performs reading for the biosensor cartridge 100, and matches the reading result with the certification result of the biosensor cartridge 100 and processes it.

Accordingly, the operator 250 can reduce the error by minimizing the time difference of the result matching by simultaneously executing the module control of the diagnostic device 200 and the execution of the read program.

The operator 250 can include a memory card as a data storage device, a library file for diagnosing biomaterials, and an embedded system board equipped with a signal processing device.

For example, a memory card capable of storing output signal data is inserted into the embedded system board, and a system OS, driving program, library file for analysis, and the like are stored in the memory card.

In addition, signal processing for concentration analysis of biomaterials is calculated through comparison analysis with library files in the CPU of the embedded system board, and the analyzed result is stored again in the memory card. In addition, the wireless transceiver 260 can be mounted together in such an embedded system board but is not limited thereto.

The biosensor diagnostic device 200 includes a display device 290 as a user interface, and the display device 290 includes a liquid crystal display device, a touch panel, and the like to display an analyzed result detected by creating a program considering a user's convenience. As a user interface, it can include various types of terminals, dials, buttons, and the like.

A terminal 297, a dial 296, a button 294, and the like can turn on/off the operation of the biosensor diagnostic device 200 and can be connected to the operator 250 to control the operator 250 according to a user command. That is, as a user's command is input in the interface 297, 296, 294, the diagnosis of the biosensor cartridge 100 can be started, where the display unit 290 displays a progress during the diagnosis process and displays a diagnosis result after the completion of the diagnosis.

The biosensor diagnostic device 200 includes a separate power supply 280 capable of applying power to a plurality of modules, and the power supply 280 includes a battery 281. Accordingly, it is possible to supply power to the internal module from the battery 281 by charging an external power source, and thus the device 200 can be portable.

Meanwhile, the signal conversion amplifier 210, the signal filter 220, the signal converter 230, the sensor converter 240, and the operator 250 can be installed within the signal processor 295 implemented in the form of system-on-chip (SOC).

Meanwhile, an electrical signal from the biosensor cartridge 100 can be delivered to the signal conversion amplifier 210 within the signal processor 295 through the interface 205.

Meanwhile, an electrical signal from the sensor converter 240 within the signal processor 295 can be delivered to the biosensor cartridge 100 through the interface 205.

Hereinafter, a detailed structure according to an example of the biosensor diagnostic device 200 will be described with reference to FIGS. 3 and 4.

Figure 3:
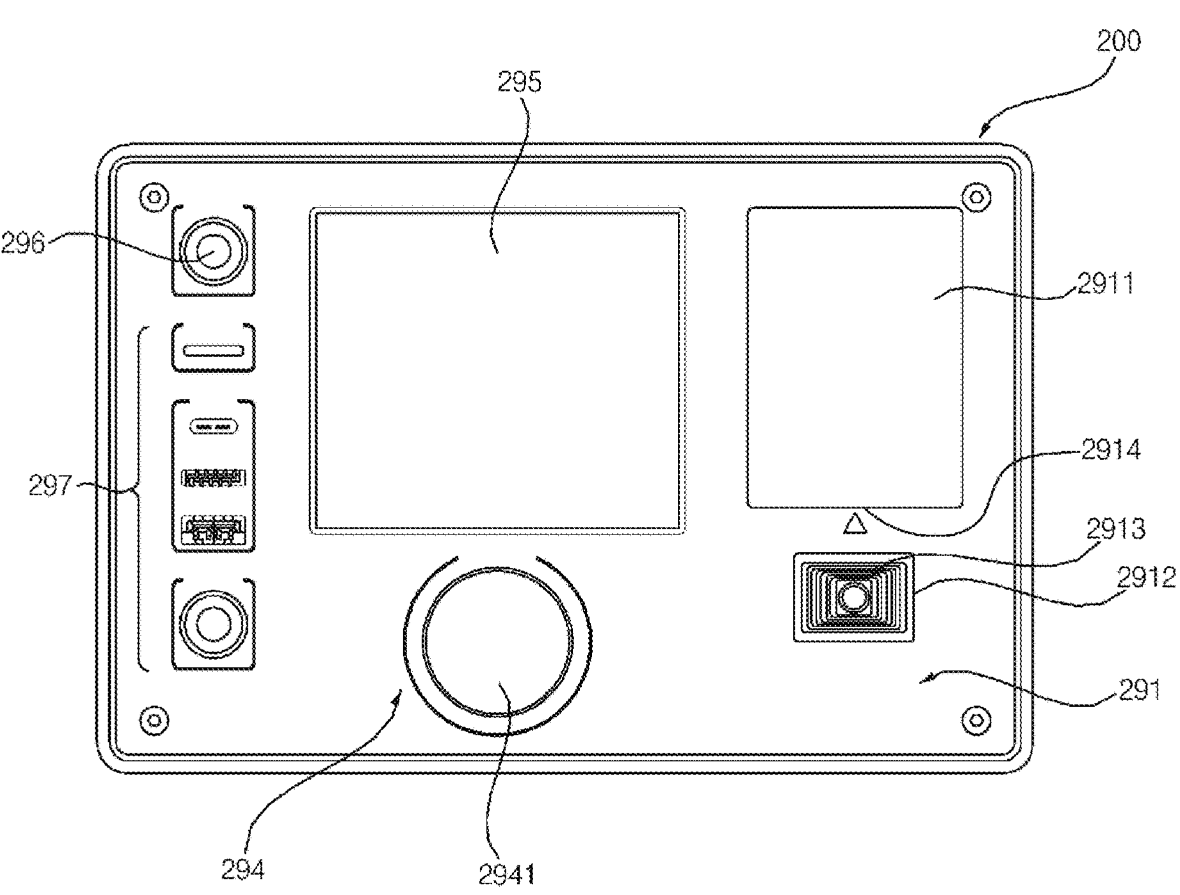
FIG. 3 is a front view of an example of the biosensor diagnostic device of FIG. 1 according to an embodiment of the present disclosure.

FIG. 3 is a front view of an example of the biosensor diagnostic device 200 of FIG. 1, and FIG. 4 is an exploded perspective view of the biosensor diagnostic device 200 of FIG. 3.

Referring to FIGS. 3 and 4, the biosensor diagnostic device 200 according to the present embodiment is provided as a portable integrated device.

Here, the state of being integrated can include all states recognized as a single device in movement, disposition, and use of the diagnostic device 200. For example, the state of being integrated can mean that that it is located together inside the same case and is integrated by the same case, can mean that it is fixed by being fitted or attached to the same member and integrated by the same member, can mean that it is formed together in the same member to constitute a part of the same member, or can mean that it is wrapped or fixed together by the same member. On the other hand, it can be difficult to be considered as being integrated in the case of being connected by a separate output cable or the like.

The integrated biosensor diagnostic device 200 according to the present embodiment can include a separate inner cover 205 (e.g., inner frame) inside the case 201, 202, and a front panel 291 is disposed to cover a plurality of modules accommodated in an accommodating portion 208 of the inner cover 205 and a front surface of the inner cover 205.

In the exploded perspective view of FIG. 4, the left side is defined as a front surface and the right side is defined as a rear surface along the X axis where the plurality of modules overlap, and the Y axis and Z axis perpendicular to the X axis are defined as two axes that forms a reference plane of the front panel 291 provided to a user.

The case 201, 202 of the biosensor diagnostic device 200 according to the present embodiment can include a front case 201 and a rear case 202. The rear case 202 is formed to have an accommodating portion 203 therein (e.g., hollow area or space), and to have a bottom surface and a side surface.

The front case 201 and the rear case 202 can be disposed to face the accommodating portion 203 while the side surfaces are in contact with each other.

The accommodating portion 203 formed by the front case 201 and the rear case 202 is changed from an open space to a closed space according to the opening and closing of the front case 201.

An outer case accommodating the front case 201 and the rear case 202 simultaneously can be further formed. The outer case can be formed in a box type as shown in FIG. 3, can have a handle formed for easy portability, and have a pedestal formed to dispose the diagnostic device 200 at a certain angle.

The bottom surfaces of the front case 201 and the rear case 202 have the same size and define the total area of the biosensor diagnostic device 200.

The bottom surface can be formed in various shapes, and the shape can be a rectangle as shown in FIG. 4, but is not limited thereto, and can be a circle, an ellipse, a rhombus, or the like.

Meanwhile, when the shape of the bottom surface is a rectangle as shown in FIG. 4, the area is a portable size, and in the situation of a polygon, one side can satisfy 30 cm or less, but it is not limited thereto, and it can be further miniaturized.

The height of the side surface forming the accommodating portion 203 of the rear case 202 can be greater than the height of the side surface of the front case 201, and the inner cover 205 is formed in the accommodating portion 203 of the rear case 202.

The inner cover 205 has the same shape as the rear case 202 so that it can be inserted into the accommodating portion 203 of the rear case 202, and the bottom surface of the inner cover 205 can have a smaller area than the rear case 202, but can be fitted to minimize a space between the side surface and the bottom surface of the rear case 202 and the side surface and the bottom surface of the inner cover 205.

The inner cover 205 serves as a cover that achieves a substantial integration, and when the case 201, 202 is damaged, the inner cover 205 can be separated from the case 201, 202 and replaced.

A plurality of modules are accommodated inside the accommodating portion 208 of the inner cover 205.

A supporter 2081, 2082 (e.g., a post or pillar type member) for supporting a module while defining the position of each module can be formed on the bottom surface of the inner cover 205, and the supporter 2081, 2082 can be variously designed depending on the disposition of the inner modules.

The main board 255 is accommodated in the accommodating portion 208 of the inner cover 205.

The main board 255 can be electrically connected to internal modules for executing a plurality of functions, and as shown in FIG. 4, a display module 295 constituting the display device 290 and the cartridge insertion module 2911 in which the signal conversion amplifier 210 and the sensor converter 240 are integrated can be disposed in the front direction of the main board 255. In addition, a control switch 254 of the user interface of the front panel 291 can be disposed on the front surface.

An operation module 251 and a communication module 261 for controlling the operation of the control device and reading a detection signal according to a program can be disposed on the rear surface of the main board 255.

In addition, a QR reading module 271 can be disposed on the rear surface of the main board 255.

A battery 281 for applying power to the main board 255 and each of the functional modules is disposed, and the battery 281 can be disposed adjacent to the bottom surface of the inner cover 205.

Specifically, the front panel 291 includes a reference plane exposed on the front surface of the biosensor diagnostic device 200 as shown in FIG. 3.

The front panel 291 includes a first opening 292 for exposing a display module 295 that is disposed on the rear surface of the front panel 291 and displays an image on the front surface.

The first opening 292 can be covered with a transparent film, but is not limited thereto, and the display device 290 of the display module 295 can be directly exposed.

A plurality of buttons, dials, and terminals 294, 296, 297 and the like for a user interface can be disposed around the first opening 291.

The plurality of buttons, dials, and terminals 294, 296, 297 can be modified in various forms according to design. For example, as shown in FIG. 3, a plurality of buttons 294-2941 can be disposed in a lower side of the first opening 292, and a plurality of dials 296 can also be disposed on the left side of the first opening 292, thereby receiving operation commands directly from a user.

Meanwhile, the cartridge insertion module 2911 is disposed in the right side of the first opening 292 in the front panel 291, and in the right side of the reference plane.

The cartridge insertion module 2911 protrudes from the reference plane to the front surface and includes a terminal portion to be electrically connected by inserting the connection terminal 153 of the cartridge in the Z-axis direction.

Accordingly, a terminal portion is formed in a side surface of the insertion module 2911, and the terminal portion can include at least one insertion hole 2914.

The insertion hole 2914 can be implemented in various ways depending on the shape of the connection terminal 153 of the cartridge. When the connection terminal 153 of the cartridge is formed in an SD card chip type, a USB type such as USB-A, USB-C type, or a PIN type, correspondingly, it can be formed to read an electrode of the connection terminal 153.

In addition, when a plurality of insertion holes 2914 are formed to read various types of connection terminal 153, the plurality of insertion holes 2914 can be disposed in parallel along the X-axis direction in the side surface of the insertion module 2911.

A second opening 293 for exposing the QR reading module 271 is disposed in the lower side of the insertion module 2911.

The second opening 293 is formed in a position aligned with the rear surface of the housing 110 of the cartridge 100 in the X-axis direction in a state in which the connection terminal 153 of the cartridge is inserted into the insertion hole 2914 of the cartridge insertion module 2911.

The second opening 293 can be covered with a transparent film, and the second opening 293 can have a rectangular shape, but an area of the second opening 293 can be smaller than that of the first opening 292.

The second opening 293 serves as a passage through which the QR reading module 271 disposed on the rear surface reads the QR code of the cartridge 100 that is placed on the front surface. In the second opening 293, a light guide part 2912 protruding from the rear surface of the front panel 291 to form a sidewall of the second opening 293 in order to maintain a distance between the QR reading module 271 and the cartridge 100 is formed.

The light guide part 2912 can serve as an illumination for photographing of the QR reading module 271 while maintaining the distance of the QR reading module 271. That is, the light guide part 2912 can include a light guide plate formed on a sidewall of the second opening 293.

A main board 255 in which each module is mounted is disposed on the rear surface of the front panel 291, and the main board 255 can also have a shape similar to the bottom surface of the inner cover 205.

The main board 255 is divided into a display area 2551 in which the display module 295 is disposed in correspondence with the area division of the front panel 291, a cartridge area 2552 corresponding to the cartridge insertion module 2911, a QR area 2553 corresponding to the second opening 293, and a control area 254 corresponding to the button and the dial for a user interface (e.g., see FIG. 4).

The main board 255 is a circuit board on which a circuit is patterned on the front and rear surfaces, and a connection terminal or a connector for electrical connection is disposed in each area. Each functional module can be integrated on the main board 255 after connecting the connection terminal of the board and connector and the connection terminal of each module or connector while being physically fixed in a defined area.

As shown in FIG. 4, a terminal module 241 in which the signal conversion amplifier 210, the signal filter 220, and the sensor converter 240 are integrated is mounted in the cartridge area 2552 of the main board 255 corresponding to the cartridge insertion module 2911. The terminal module 241 can be connected to an insertion hole module 211 into which the connection terminal 153 of the cartridge is inserted by a flexible printed circuit board (FPCB) 2111 or can be implemented as a single component.

In addition, the display module 295 can be an LCD or LED panel module disposed in the display area 2551, and a terminal opening 2951 can be formed in the main board 255 in order to connect the operation module 251 on the rear surface of the main board 255 with the battery 281.

The operator 250 and the communication module 261 can also be connected to the main board 255 through a connector at the rear surface of the main board 255, but the disposition on the main board 255 is not limited thereto.

Meanwhile, the QR reading module 271 that reads a QR code through a QR opening 2554 formed in the QR area 2553 is disposed on the rear surface of the main board 255, and the QR reading module 271 is also electrically connected to the main board 255 through the flexible printed circuit board FPCB 2711 to receive power and control signals.

A side frame 209 is formed for the disposition and fixing of such modules. The side frame 209 fixes the inner cover 205 and the front panel 291, and the inner cover 205 is fixed to the side frame 209 through a screw hole 2061 extended from one end portion 206 of the side surface. Each module is fixed at a specific position on the main board 255 through a plurality of other fixing parts, the main board 255 is physically fixed by coupling a screw and a screw hole between a plurality of fixing protrusions 2081 and 2082 protruding from the bottom surface of the inner cover 205 and the front panel 291.

Each module and component disposed therebetween is fixed by fixing the main board 255, the front panel 291, and the inner cover 205, and an electrical connection is maintained without being shaken during movement.

In addition, the front panel 291 and the inner cover 205 are fixed together through the screw hole and the screw of the side frame 209 to be integrated. Fixing and assembling of each component proceeds by the screw hole and the screw, thereby making it easy to disassemble and reassemble.

The front case 201, the rear case 202, the inner cover 205, and the front panel 291 can be formed of a resin, such as polycarbonate or plastic for portability.

The biosensor diagnostic device 200 is, as shown in FIG. 3, provided to a user by exposing the front panel 291 in a form of having a space for accommodating a plurality of modules therein, and various external cases can be applied.

In particular, in the reference plane of the front panel 291 provided to a user as shown in FIG. 3, a screen of the display module 295 is provided, and various buttons and dials for a user interface are provided. In particular, a power button, a plurality of control buttons, and a USB terminal can be provided. In addition, the cartridge insertion module 2911 is provided to one side of the display module 295, and the connection terminal 153 is inserted into the insertion hole 2914 parallel to the reference plane of the panel 291, so that diagnosis of the biosensor cartridge 100 is possible.

Hereinafter, the biosensor cartridge 100 applied to the present embodiment will be described with reference to FIGS. 5 to 12.

Figure 5A:
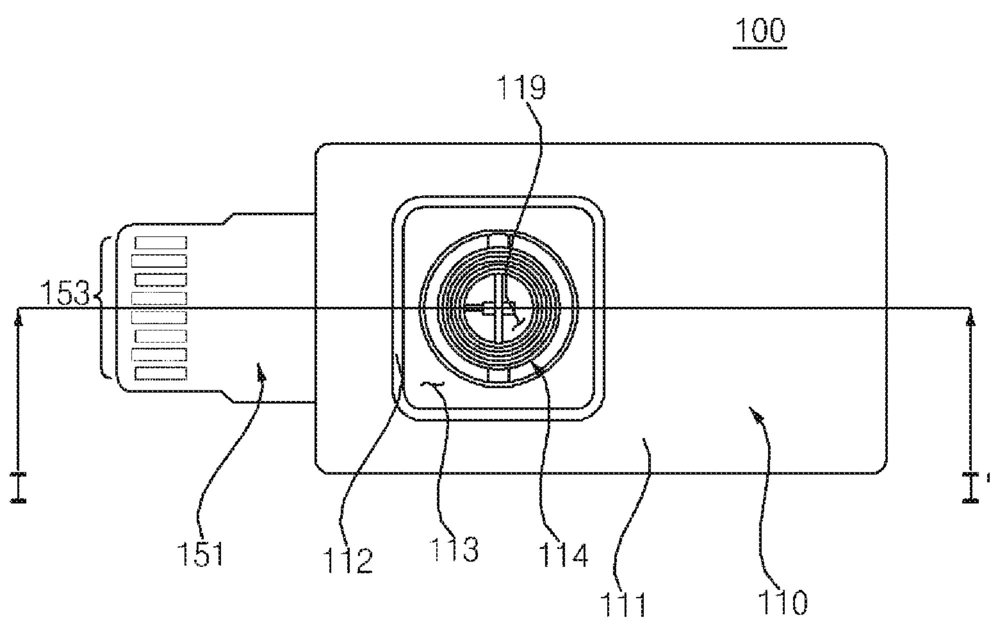
FIGS. 5A and 5B are top and rear views of an example of the biosensor cartridge of FIG. 1 according to an embodiment of the present disclosure.
Figure 5B:
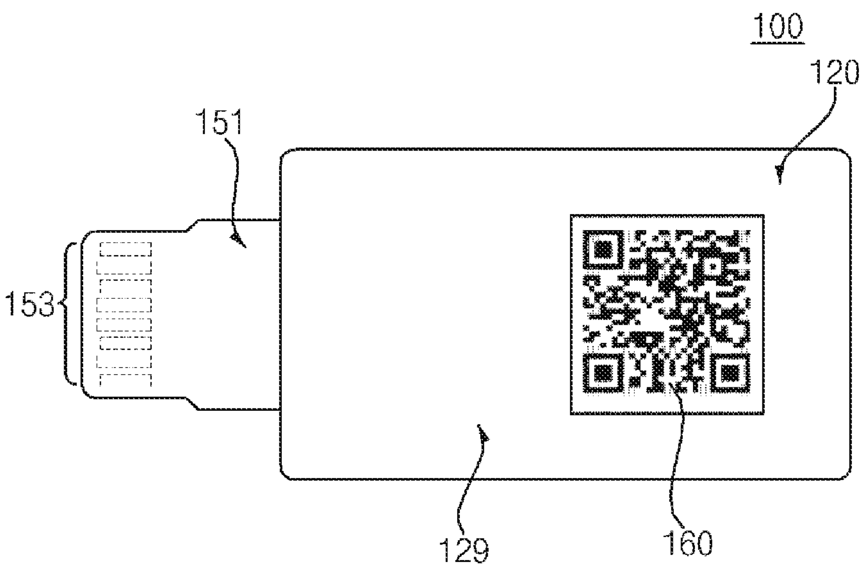
Figure 7:
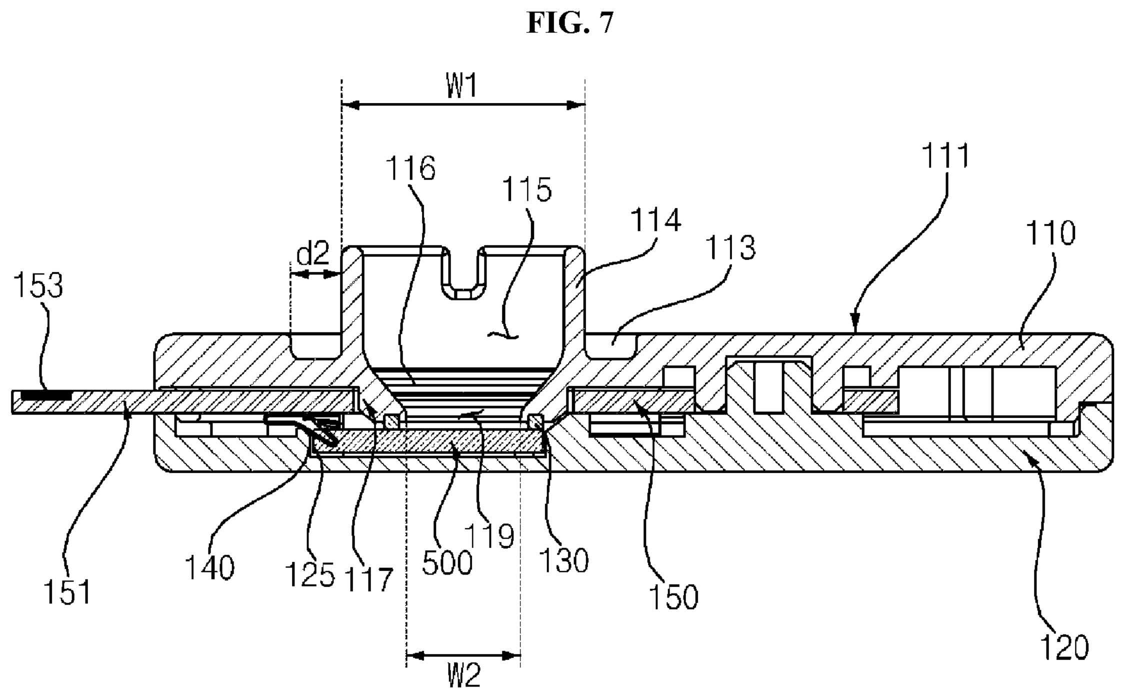
FIG. 7 is a cross-sectional view of the biosensor cartridge of FIGS. 5 and 6 taken along lines I-I' and II-II' according to an embodiment of the present disclosure.
Figure 8:
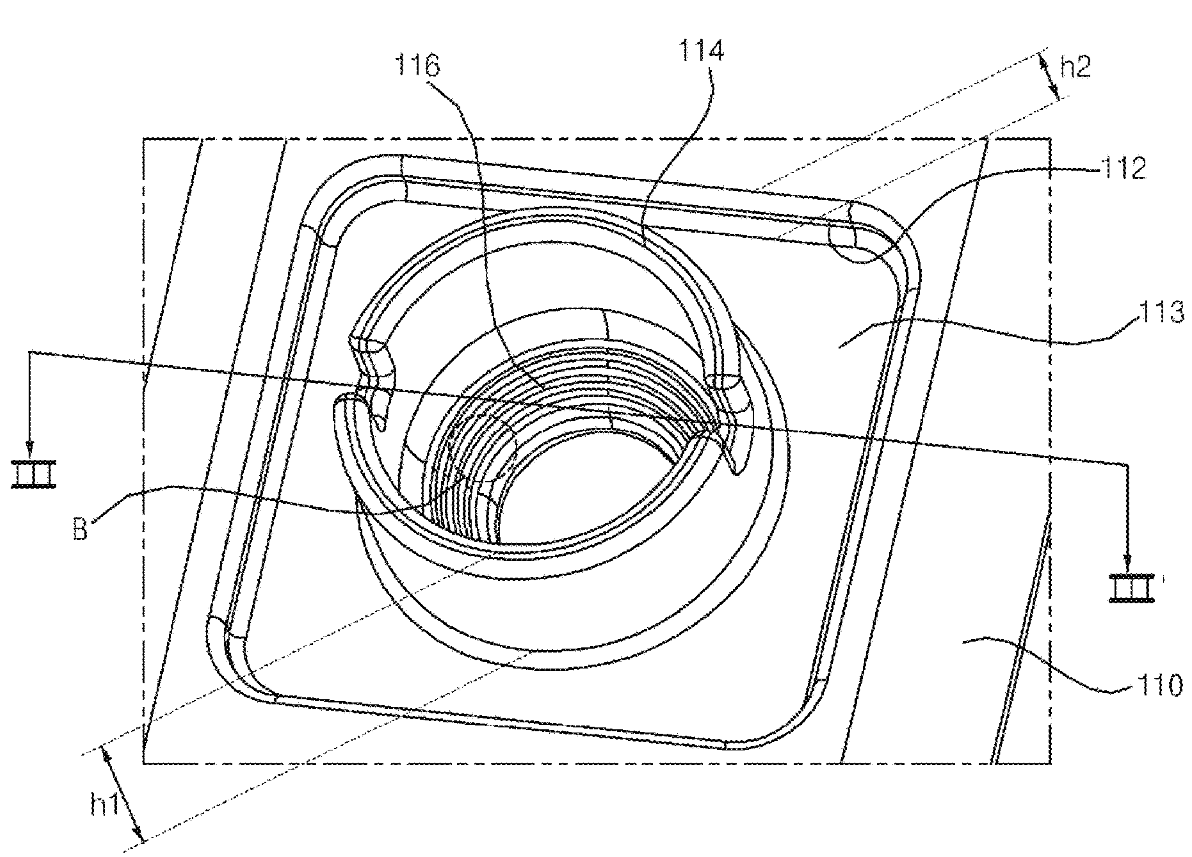
FIG. 8 is an enlarged view of region A of FIG. 6 according to an embodiment of the present disclosure.
Figure 9:
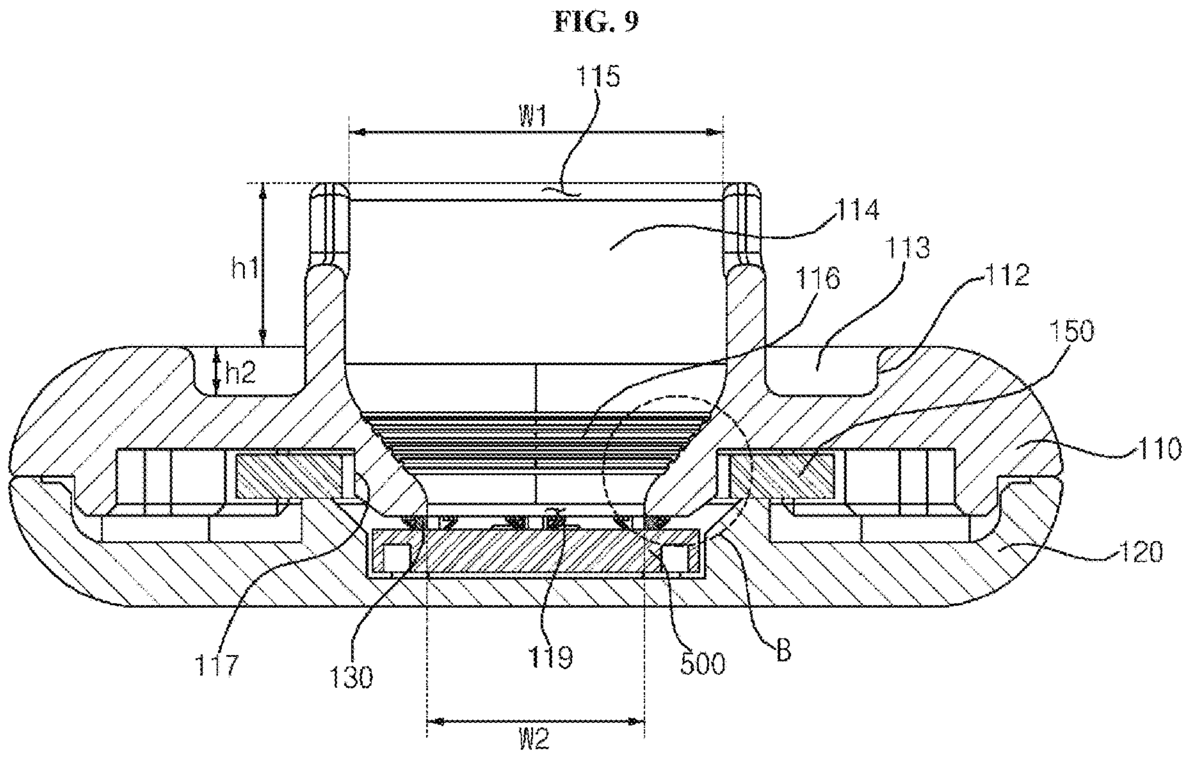
FIG. 9 is a cross-sectional view of the biosensor cartridge of FIG. 8 taken along line III-III' according to an embodiment of the present disclosure.
Figure 10:
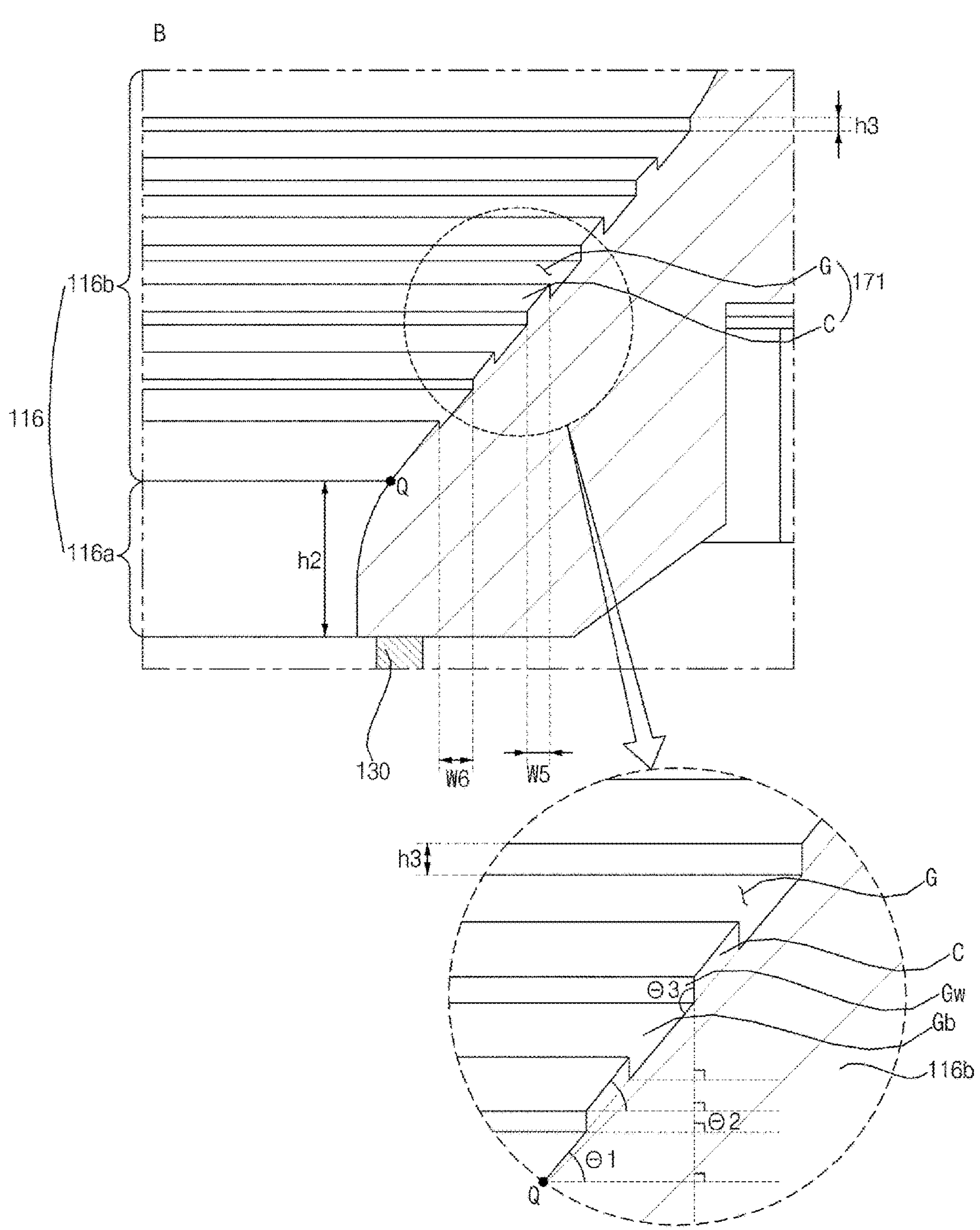
FIG. 10 is an enlarged view of region B of FIG. 9 according to an embodiment of the present disclosure.
Figure 11:
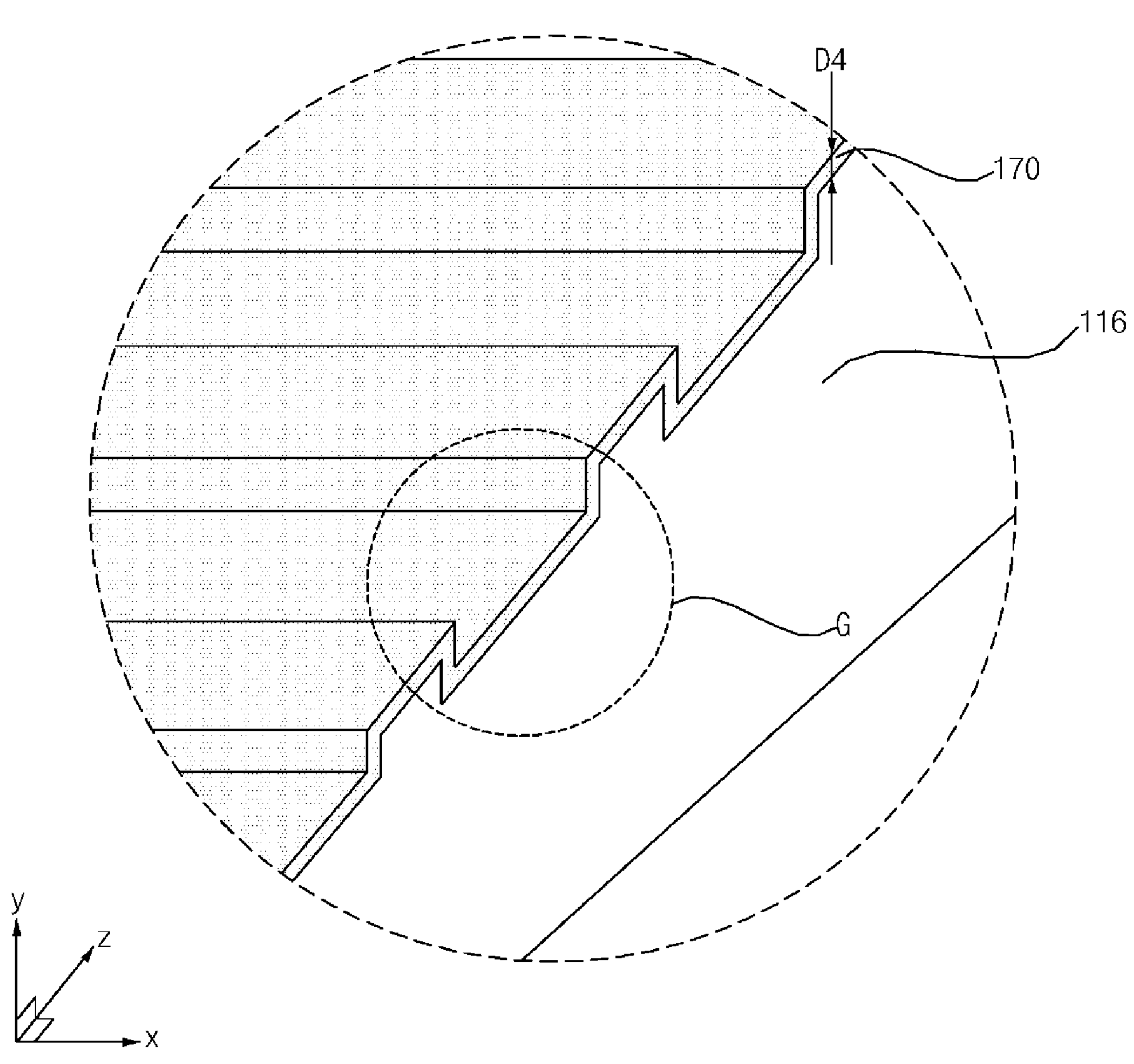
FIG. 11 shows another application example of the biosensor cartridge of FIG. 10 according to an embodiment of the present disclosure.

FIGS. 5A and 5B are top and rear views of an example of the biosensor cartridge 100 of FIG. 1, FIG. 6 is an exploded perspective view of an example of the biosensor cartridge 100 of FIG. 1, and FIG. 7 is a cross-sectional view of the biosensor cartridge 100 of FIGS. 5 and 6 taken along lines I-I' and II-II'. At this time, FIG. 8 is an enlarged view of region A of FIG. 6, FIG. 9 is a cross-sectional view of the biosensor cartridge of FIG. 8 taken along line III-III', FIG. 10 is an enlarged view of region B of FIG. 9, FIG. 11 shows another application example of the biosensor cartridge of FIG. 10, and FIGS. 12A, 12B and 12C are diagrams illustrating a contact angle of a solution according to a micropattern.

Referring to FIGS. 5A to 12, the biosensor cartridge 100 according to the present embodiment accommodates a biosensor chip 500 that generates an electrical detection signal according to a target material and has a structure of including a connection terminal 153 capable of transmitting the detection signal to an external diagnostic device 200.

Specifically, the biosensor cartridge 100 is formed of a bar type housing 110, 120, a partial surface 151 of the circuit board 150 protrudes from the end surface of the side surfaces of the housing 110, 120, and a connection terminal 153 that is inserted into the external diagnostic device 200 and transmits the detection signal is formed on the partial surface 151 of the protruding circuit board 150.

The accommodating portion 119 for accommodating a specimen is formed on an upper surface 111 of the housing 110, 120, and a QR label 160 can be attached to the lower surface or rear surface of the housing 110, 120.

The connection terminal 153, which protrudes from the side surface of the housing 110, 120 and is exposed, is disposed in the same direction as the lower surface of the housing 110, 120 and is not exposed when the cartridge 100 is viewed from the upper surface. Accordingly, it is possible to reduce the risk that the specimen flowing out of the accommodating portion 119 touches the connection terminal 153.

The biosensor cartridge 100 includes housing 110, 120, a biosensor chip 500, and a circuit board 150.

The circuit board 150 is also formed in a bar type and has one end where a connection terminal 153 is formed so that the connection terminal 153 of the circuit board 150 is coupled to be exposed to the outside of the housing 110, 120, thereby forming the entire shape of cartridge 100.

Specifically, the housing 110, 120 includes a lower housing 120 and an upper housing 110.

The lower housing 120 includes a bar-type bottom surface 121 and a side surface 122 surrounding the bottom surface 121. The bottom surface 121 includes a plurality of coupling protrusions 127, 128 protruding toward the upper housing 110, and each of the coupling protrusions 127, 128 is fitted with a coupling groove of the upper housing 110 so that the upper and lower portions of the housing 110, 120 are coupled and integrated.

A substrate protrusion 127 defining a position while fixing the circuit board 150 toward the upper housing 110 is formed on the bottom surface 121 of the lower housing 120, and a plurality of sensor protrusions 126 defining a chip area 125 in which the biosensor chip 500 is disposed are formed in one side thereof.

The sensor protrusion 126 is disposed to correspond to the size of the biosensor chip 500 to define a chip area 125 in which the biosensor chip 500 is disposed and is formed to have a certain elasticity so that the biosensor chip 500 can be fitted. Each sensor protrusion 126 has a protruding structure having an inclination toward the chip area 125 so that it is not damaged by the edge of the sensor protrusion 126 when the biosensor chip 500 is mounted. However, since the sensor protrusion 126 does not electrically connect the biosensor chip 500, it can be implemented in various forms, and can be formed as a rail structure for sliding coupling in addition to fitting.

A biosensor chip 500 is disposed in the chip area 125.

The biosensor chip 500 is a semiconductor-based biosensor and is divided into a sensor area 530 that reacts according to a target material in the specimen through contact with the specimen, and a pad area 510 for transmitting a detection signal generated according to the sensor area 530 to the circuit board 150.

The pad area 510 can be patterned to be disposed in one side of the biosensor chip 500 as shown in FIG. 6, and accordingly, the electrical connection between the circuit board 150 and the biosensor chip 500 is performed in the pad area 510.

The biosensor chip 500 can have different sizes depending on the size of the cartridge, for example, can have a rectangular shape of 8 mm*6 mm, or can have a square shape of 6 mm*6 mm. The size of the biosensor chip 500 can be variously implemented according to the performance of the biosensor chip 500 or the purpose of the biosensor chip 500.

The detailed structure of the biosensor chip 500 will be described in detail later.

The circuit board 150 is disposed on the biosensor chip 500.

The circuit board 150 can be provided as a rigid board like a printed circuit board (PCB) board, and the biosensor chip 500 is electrically/physically bonded to the lower portion.

The circuit board 150 includes a sensor opening 155 through which a sensor area 530 of the biosensor chip 500 is exposed, and the sensor opening 155 has a size smaller than that of the biosensor chip 500. In addition, the opening 155 can have a size corresponding to the sensor area 530 of the biosensor chip 500 and has a size to expose the sensor area 530.

The circuit board 150 further includes a protrusion hole 154 through which the substrate protrusion 127 of the lower housing 120 penetrates to fix the circuit board 150, and accordingly, the circuit board 150 and the lower housing 120 are fixed.

The circuit board 150 can be implemented by a plurality of circuit patterns patterned on a base member (not classified by reference numerals, denoted by 150 in the drawing) as the deposition structure thereof, and an insulating layer covering the circuit pattern.

The circuit pattern and the insulating layer can be formed on a rear surface of the base member, and a reinforcing plate can be attached to the front surface of the base member. A rear surface of the circuit board 150 can be defined as a surface facing the lower housing 120, and a front surface of the circuit board 150 can be defined as a surface facing the upper housing 110.

The required strength at the time when a part of the circuit board 150 is used as the connection terminal 153 that is inserted into the diagnostic device 200 can be satisfied by attaching the reinforcing plate to the rear surface of the circuit board 150 as described above.

On the rear surface of the circuit board 150, a circuit pattern including a plurality of connection pads 158 for connecting to the biosensor chip 500 is formed, and a circuit pattern that extends to the connection pad 158 to transmit the detection signal from the connection pad 158 to the external diagnostic device 200 is formed to be connected to the connection terminal 153 of the front surface.

Accordingly, the number of connection terminals 153 of the circuit board 150 can be equal to or larger than the number of pads of the biosensor chip 500.

The plurality of connection terminals 153 can be spaced apart from each other at one end of the exposed surface 151 of the circuit board 150, e.g., at one end of the circuit board 150, and disposed in parallel.

For example, when the biosensor chip 500 has three pads, the number of the connection pads 158 of the circuit board 150 also satisfies three, and the number of the connection terminal 153 satisfies three or more.

The connection terminal 153 further includes terminals not electrically connected to each connection pad 158 and can be used as a terminal for electrostatic discharge (ESD) blocking.

As shown in FIG. 6, the circuit pattern patterned on the front surface of the circuit board 150 can include eight connection terminals 153. In such a connection terminal 153, when the biosensor chip 500 is driven in multi-channel to be connected to a plurality of connection pads 511 and to transmit and receive signals, six connection terminals can be allocated as a connection terminal 153 for transmitting and receiving signals of each pad by connecting to the source pad, drain pad, and gate pad of the biosensor chip 500 corresponding to each channel, and two connection terminals are applicable as a terminal for ESD and incoming detection signal generation.

Such a connection terminal 153 can be formed as a USB-A type depending on an embodiment, but a USB-C type having more terminals as shown in FIG. 1 can also be utilized.

Also, the connection terminal 153 can be implemented as a pin type, and more terminals can be implemented.

Thus, the number of pads of the connection terminal 153 can increase in proportion to the number of probe material applied to the biosensor chip 500, e.g., the number of source electrodes (or the number of drain electrodes).

Meanwhile, the circuit board 150 includes a plurality of coupling grooves, and the plurality of coupling grooves are formed to be able to fit while specifying a position when the upper housing 110 and the lower housing 120 are coupled.

Meanwhile, the upper housing 110 has a structure where the upper surface 111 and the rear surface are different from each other as shown in FIG. 6.

The upper housing 110 faces the lower housing 120 and is coupled to the lower housing 120 and serves as an upper case capable of accommodating the circuit board 150 and the biosensor chip 500 therein. In addition, an accommodating portion 119 exposing the sensor area 530 of the biosensor chip 500 is formed in the upper housing 110 to accommodate a test target specimen.

The upper housing 110 is formed to have rigidity that can firmly support the connecting member 140 by pressing the connecting member 140 with a certain force.

The upper housing 110 and the lower housing 120 can be configured to surround the surfaces of the biosensor chip 500 and the circuit board 150 to protect the biosensor chip 500 and the circuit board 150 from the outside. Due to the strong coupling between the upper housing 110 and the lower housing 120, the specimen provided to the biosensor chip 500 through the accommodating portion 119 can be prevented from leaking into the housing 110, 120.

At this time, when the upper housing 110 and the lower housing 120 are coupled, an opening through which the connection terminal 153 of the circuit board 150 protrudes is formed in one side of the side surface, e.g., in a cross-section, so that the connection terminal 153 is exposed to a cross-section and is inserted into the insertion hole 2914 of the external diagnostic device 200 as the connection terminal 153 of the cartridge.

The accommodating portion 119 for exposing the sensor area 530 of the biosensor chip 500 and accommodating a specimen is formed on the upper surface 111 of the upper housing 110. The accommodating portion 119 is a space for inducing a reaction with the exposed sensor area 530 by accommodating a test target specimen in a fluid state, e.g., in a liquid state, and the accommodating portion 119 forms a conical channel (e.g., a funnel shape) whose diameter becomes narrower as it approaches the sensor area 530 from the upper surface 111.

In what follows, the accommodating portion 119 of the upper housing 110 will be described in detail with reference to FIGS. 8 to 12.

The accommodating portion 119 is formed to have an inclined surface 116 such that a diameter W1 of the opening of the upper surface is larger than a diameter W2 of the opening at the distal end of the accommodating portion 119.

The diameter W2 of the opening at the distal end of the accommodating portion 119 can be 3 mm to 6 mm (e.g., 4.5 mm). Preferably, it can satisfy 3.8 to 4.5 mm, more preferably 4 mm to 4.3 mm (e.g., 4.15 mm). However, it is not limited thereto and can be variable depending on the overall size of the cartridge 100 and the size of the biosensor chip 500.

At this time, a first inclination angle θ1 of the inclined surface 116—the angle of the inclined surface 116 with respect to the horizontal direction (x-axis) in which the biosensor chip 500 is placed, when viewed from the cross section in FIG. 7—can be uniform but can have an inflection point.

That is, the first inclination angle θ1 increases as it approaches the sensor area 530, and it forms verticality in the outermost area 116*a* closest to the sensor area 530, so that it can be changed to a cylindrical passageway.

That is, as shown in FIG. 10, the inclined surface 116 has an inclined area 116*b* having the first inclination angle θ1 and has an outermost area 116*a* extending from the inclined area 116*b* and perpendicular to the horizontal direction (x-axis) after the inflection point Q, to the lower portion of the inclined area 116*b*.

As described above, since the accommodating portion 119 has the inclined surface 116, a concave groove having a depth that is a height from the upper surface of the upper housing 110 to the sensor area 530 is formed. A specimen is collected in the groove to induce a reaction with the probe material in the sensor area 530.

Meanwhile, the accommodating portion 119 further includes a guard 114 (e.g., side wall) for preventing the specimen of the accommodating portion 119 from flowing to the outside as shown in FIGS. 5A to 9. The guard 114 can be formed in a cylindrical shape and is formed to surround the opening of the upper surface 111 of the upper housing 110 and protrude upward (in the y-axis) from the upper surface 111.

Accordingly, the diameter W1 of the guard 114 can be the same as the diameter of the opening of the upper surface 111.

A guard groove 113 of a certain depth is formed on the upper surface 111 of the upper housing 110 while surrounding the accommodating portion 119. The guard groove 113 is to prevent the specimen overflowing from the accommodating portion 119 from flowing out of the housing 110 or spilling and is formed to be recessed by a predetermined depth h2 from the upper surface 111.

The depth h2 of the guard groove 113 can be formed to satisfy ⅓ to ½ of the thickness of the upper surface of the upper housing 110.

The guard groove 113 can be formed in a circular shape identical to the shape of the guard 114 but can be formed in a rectangular shape having a minimum distance d2 or more from the guard 114 as shown in FIG. 7.

The height h1 of the guard 114 can be greater than the depth h2 of the guard groove 113 and can have a height equal to or smaller than the overall thickness of the housing 110, 120.

As described above, the accommodating portion 119, where the specimen and the sensor area 530 contact each other, firstly has a concave cup shape to accommodate the specimen and provides a space where the target material of the specimen and the probe material of the sensor area 530 react with each other. In addition, the accommodating portion 119 forms a guard 114 surrounding the opening of the upper surface 111 to secure the amount of the specimen by accommodating the overflowing specimen secondarily, and to prevent the risk of exposing the specimen to the outside.

In addition, tertiarily, the guard groove 113 is formed around the guard 114 to accommodate the specimen when the specimen overflows the guard 114 or flows to the outside of the guard 114, thereby preventing the specimen that can contain hazardous substances from exposing to the outside. For example, the guard groove 113 can form a type of moat or overflow/spill containment area.

Thus, the test can be safely performed by changing the shape of the accommodating portion 119 for accommodating the specimen in the upper housing 110.

The accommodating portion 119 of the upper housing 110 accommodates a liquid test sample, and the test sample is randomly put into the accommodating portion 119, making it difficult to adjust the input amount.

In other words, when a large amount of test specimens are put into the accommodating portion 119 for a prompt and accurate response, depending on the size of the biosensor cartridge 100 and the limit of the accommodation volume of the accommodating portion 119, there is a risk that the test specimen can flow into the area outside the guard 114 of the accommodating portion 119.

As described above, when the test specimen flows to the outside, there is a risk that it can contain dangerous pathogens (e.g., viruses or bacteria), fatal to the user, and since the specimen flowing to the outside is in a liquid state, an electronic component can be damaged (e.g., a short circuit) if the specimen is injected into the diagnostic device 200 or touches the connection terminal 153.

Therefore, the present embodiment employs a super water-repellent pattern structure 171 applied to the accommodating portion 119 so that even if a small amount of the test specimen is put in, all the test specimens are collected into the sensor area 530 of the biosensor chip 500 exposed by the lower opening of the accommodating portion 119 to induce a sufficient reaction. For example, the super water-repellent pattern structure 171 can have a hydrophobic property.

Specifically, referring to FIGS. 10 and 11, when the inclined surface 116 of the accommodating portion 119 includes the included area 116*b* inclined with the first inclination angle θ1, a plurality of super water-repellent pattern structure 171 is formed in the inclination area 116*b*.

The super water repellent structure 171 is intended to lower the surface energy of the inclined area 116*b*.

As the surface energy of the inclined surface 116 becomes lower, the contact angle of water to the surface increases, and the number of adhered specimens decreases.

When a small amount of test specimen is injected into the inclined surface 116, the injected specimen is induced to flow downward without being fixed to or stuck to the inclined surface 116 by the low surface energy of the inclined surface 116.

As shown in FIG. 10, the super water-repellent pattern structure 171 includes a plurality of pattern grooves G forming concentric circles around the lower opening of the accommodating portion 119 and a plurality of protrusions C between the pattern grooves G, the pattern grooves G and protrusions C continuously intersecting to form the super water-repellent pattern structure 171 (e.g., also see FIG. 8).

In other words, when the bottom surface Gb of the pattern groove G and the side surfaces Gw on both sides of the bottom surface Gb form the pattern groove G, the side surface Gw of the pattern groove G forms the side surface Gw of the protrusion C. For example, the pattern grooves G and the protrusions C can be repeatedly arranged in an alternating manner (e.g., can form a type of ribbed funnel).

The continuous pattern structure 171 can be formed entirely along the inclined surface 116 of the inclined area 116*b*.

Each pattern groove G has a ring shape, and the ring shapes of the plurality of pattern grooves G have the same center (e.g., concentric rings) and are formed along the circumferences of the respective circles having different radii, thereby not overlapping each other.

The pattern groove G can have a different contact angle $\theta_a$ with respect to the specimen liquid depending on the width W6 of the pattern groove G and the separation distance W5 between pattern grooves G, namely, the width of the pattern protrusion C (e.g., see FIG. 10).

Figures 12A, 12B:
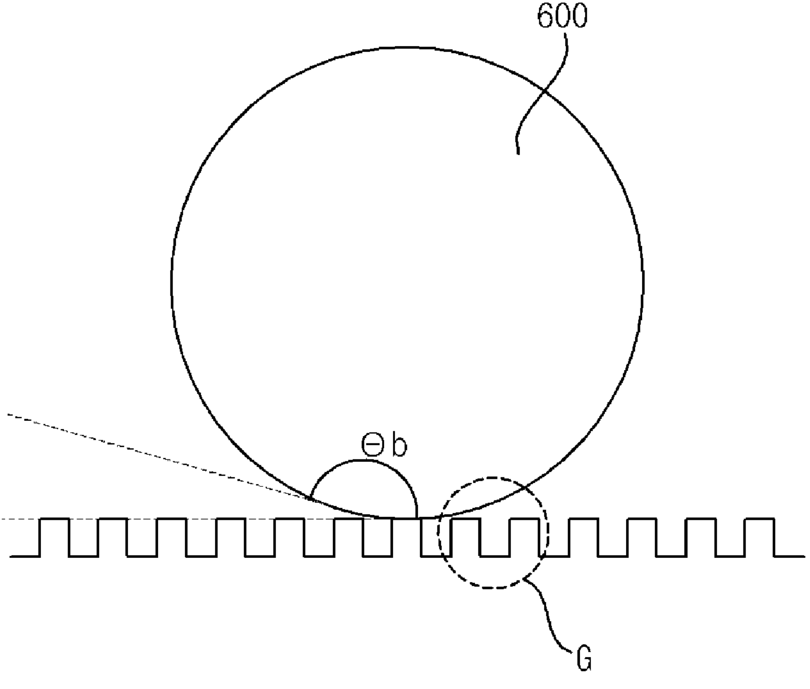

As shown in FIG. 12A, as the surface energy of the surface increases, the liquid flowing on the surface adheres more to the surface and stops flowing, and the droplet does not maintain the spherical shape of the liquid. Such a state is defined as the Wenzel state, hydrophilicity, or surface wetting; conversely, as shown in FIG. 12B, when the droplet maintains the spherical shape, and the contact angle between the liquid and the surface is 100 degrees or more, the corresponding state is defined as Cassier-Baxter state, that is, hydrophobicity or water repellency.

Therefore, when the surface energy is very low, and the surface exhibits water repellency, droplets of the liquid flowing on the surface make a contact angle against the surface at 100 degrees or more, and the surface allows the liquid to flow without getting wet. In addition, super water repellency is obtained when the contact angle is 120 degrees or more.

The inclined area 116*b* of the accommodating portion 119 according to the embodiment has a pattern structure 171 for having super water repellency, and the pattern structure 171 for maintaining the super water repellency can be maintained by controlling the width W6 of the pattern groove G and the separation distance W5 between the pattern grooves G, namely, the width of the pattern protrusion C.

Specifically, when the depth h3 of the pattern groove G is fixed to 25 μm to 55 μm, preferably 30 μm to 50 μm (e.g., 40 μm), the pattern structure 171 for super water repellency can be implemented by controlling the width W6 and the separation distance W5 of the pattern grooves G.

The depth h3 of the pattern groove G satisfies the numerical range above in consideration of the accommodation volume of the entire accommodating portion 119.

The width W6 of the pattern groove G can be 1.5 to 4.5 times the width W5 of the pattern protrusion C.

Preferably, at this time, the width W6 of the pattern groove G satisfies the range of 100 μm to 250 μm, and the width W5 of the pattern protrusion C, namely, the separation distance between the pattern grooves G can satisfy the range of 80 μm to 160 μm (e.g., 120 μm).

In this way, by forming a pattern of micro-units, a sufficient super water-repellent effect can be realized, and by forming a pattern having a size larger than a nano-pattern, the pattern can be implemented without involving laser processing but can be formed together with a mold during the injection process of the upper housing 110.

Therefore, the process cost and damage to the pattern due to laser processing can be reduced, and defects can be reduced as a sufficient separation distance is ensured between the pattern protrusions C.

As described above, a plurality of ring-shaped pattern grooves G formed in the inclined area 116*b* are continuously formed to have super water repellency, and the specimen touching the inclined area 116*b* is forced to go to the lower sensor area 530.

At this time, the bottom surface Gb of the pattern groove G of the pattern structure 171 having the super water repellency is inclined with the same first inclination angle θ1 as the inclination angle of the inclined surface 116, and the inclination angle of a plurality of the bottom surfaces Gb of the pattern grooves G can be the same.

In addition, the side surface Gw of the pattern groove G can be formed to be perpendicular θ2 to the horizontal plane, namely, a plane (X-axis) on which the biosensor chip 500 is placed. Accordingly, the angle θ3 between the pattern groove G and the bottom surface Gb has an inclination angle of 90+first inclination angle.

As described above, as the side surface Gw of the pattern groove G is inclined with respect to the bottom surface Gb at an angle θ3 greater than 90 degrees, the angle of separation from the mold during the injection process of forming the pattern is not controlled separately, and the patterns may be separated in the vertical direction.

Also, the vertical pattern structure 171 with respect to the horizontal plane can minimize the impact energy at the time the specimen falls because the specimen is accommodated by being fallen vertically in the same manner (e.g., which can help reduce any splashing).

At this time, the upper surface of the pattern protrusion C can be inclined at the same angle as the bottom surface Gb of the pattern groove G.

On the other hand, the inclined surface 116 can further include a super water-repellent coating surface 170, as shown in FIG. 11.

The super water-repellent coating surface 170 can be formed only on the inclined surface 116 but can also be formed on the entire accommodating portion 119, namely, on the whole of the inclined surface 116, the protrusion C, and the protrusion groove G.

The super water-repellent coating surface 170 can be formed by conformal coating of a fluorine-based material to a uniform thickness. The fluorine-based material can include PFA fluorine-based acrylate, methacrylate, or perfluoro polyether (PFPE), a fluorine-based polymer, H2C═CHCO2 (CH2)xCyFz.

The super water-repellent coating surface 170 can be formed to have a fourth thickness d4, where the thickness can range from several tens of nm to several μm.

In other words, the thickness of the coating surface 170 is formed to be significantly lower than the height of the protrusion and thereby does not offset the super water-repellent pattern structure 171.

Figure 12C:
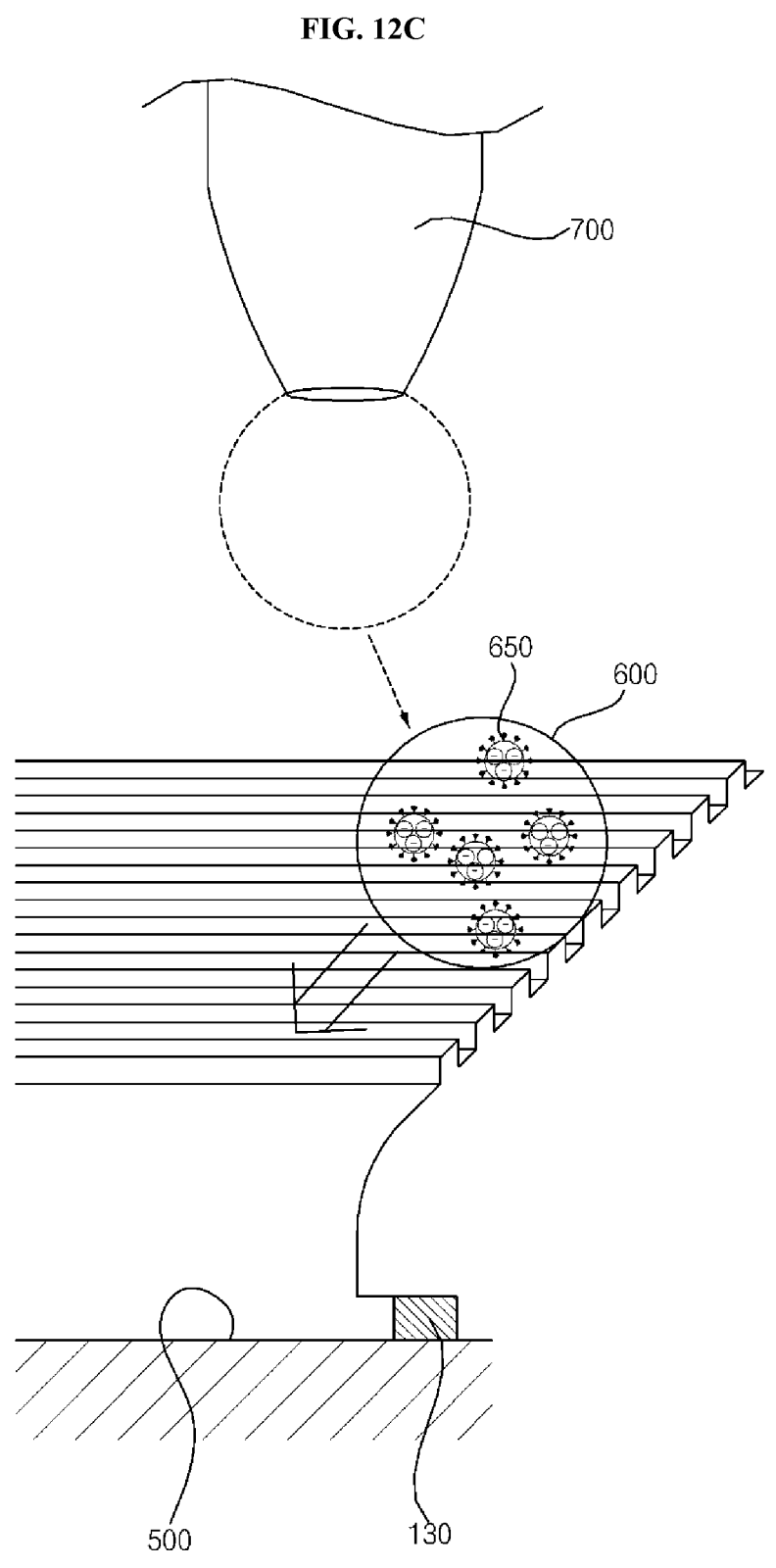

As shown in FIG. 12C, the biosensor cartridge of the present embodiment forms a super water repellent pattern structure 171 on the inclined surface 116 of the accommmodating portion 119; therefore, when a specimen 600 from the outside falls and settles on the inclined surface 116 having a first inclination angle θ1, even if part of the specimen 600 falls on the inclined surface 116, the specimen is not absorbed by the inclined surface 116 because of the low surface energy of the inclined surface 116 but flows downward at a high contact angle.

In other words, in addition to the structure that flows downward at the first inclination angle θ1 of the inclined surface 116, the pattern structure 171 that lowers the surface energy makes the specimen to flow directly downward without being absorbed in or stuck to the inclined surface 116 and collects all specimens 600 in the central sensor area 530 within a short time period.

Therefore, even if a small amount of specimen 600 is injected, all the specimen 600 is collected in the lower sensor area 530 without being absorbed by or stuck to other structures; thus, the input amount of specimen 600 can be reduced, and the risk of the specimen 600 flowing to the outside can be significantly reduced due to ability to use a smaller amount of specimen 600.

Meanwhile, the rear surface of the upper housing 110 can include an inclined portion to form the inclined surface 116 of the accommodating portion 119.

Accordingly, as shown in FIG. 9, the sensor area 530 of the biosensor chip 500 is exposed upward by the sensor opening 115 of the circuit board 150, and the lower opening of the accommodating portion 119 is aligned with the exposed sensor area 530.

At this time, the opening 115 of the circuit board 150 is fitted to surround the rear surface of the inclined surface 116 of the accommodating portion 119, thereby fixing the positions of the circuit board 150 and the upper housing 110.

In addition, to this end, the rear surface of the inclined surface 116 of the accommodating portion 119 is formed to have a vertical step 117 in an area where it meets the opening 115 of the circuit board 150.

That is, the rear surface of the inclined surface 116 of the accommodating portion 119 forms an inclined portion along the inclined surface 116 at an angle equal to or greater than the inclination angle of the inclined surface 116 of the accommodating portion 119, and is inclined at an angle equal to or greater than the inclined surface 116 to form a space coupled to the circuit board 150.

At this time, at a portion to which the opening 155 of the circuit board 150 is coupled, a step 117 corresponding to the cut surface of the opening 155 of the circuit board 150 can be formed for fitting with the opening 155 of the circuit board 150. Accordingly, the step 117 can be formed perpendicular to a horizontal plane (x-axis on which the sensor chip is placed).

The step 117 can have a spaced distance from the side surface of the opening 155 of the circuit board 150, but is not limited thereto, and can be fitted and coupled.

It is easy to fix the circuit board 150 in a situation of being fitted and coupled without a separation distance, but a separation distance can be formed for tolerance.

In addition, when the rear surface of the circuit board 150 is placed in the lower housing 120, a separation distance for tolerance can be ensured from the rear surface of the upper housing 120.

As described above, the front surface of the circuit board 150 and the rear surface of the upper housing 110 can be coupled with a certain tolerance distance to prevent distortion or bending of the circuit board 150, and to be applied as a buffer for an error in the process to reduce the defect rate.

In addition, even if the separation distance for such a tolerance is included, the circuit board 150 and the housing 110, 120 can be clearly coupled by combining with the upper and lower housings 110 and 120 by a plurality of coupling grooves and coupling holes.

Accordingly, the circuit board 150 is firstly fixed while the step 117 of the rear surface of the accommodating portion 119 and the sensor opening 115 of the circuit board 150 are fitted, and is secondarily fixed while the fixing protrusion 127 of the lower housing 120 and the fixing hole 154 of the circuit board 150 are coupled, so that the position is specified.

Meanwhile, a sealing part 130 can be further formed between the upper housing 110 and the sensor area 530.

The sealing part 130 is formed as a separate element as shown in FIG. 6 and is coupled and compressed at the time of the housing 110, 120 coupling, thereby preventing the specimen from flowing to the outside of the sensor area 530.

Figure 13:
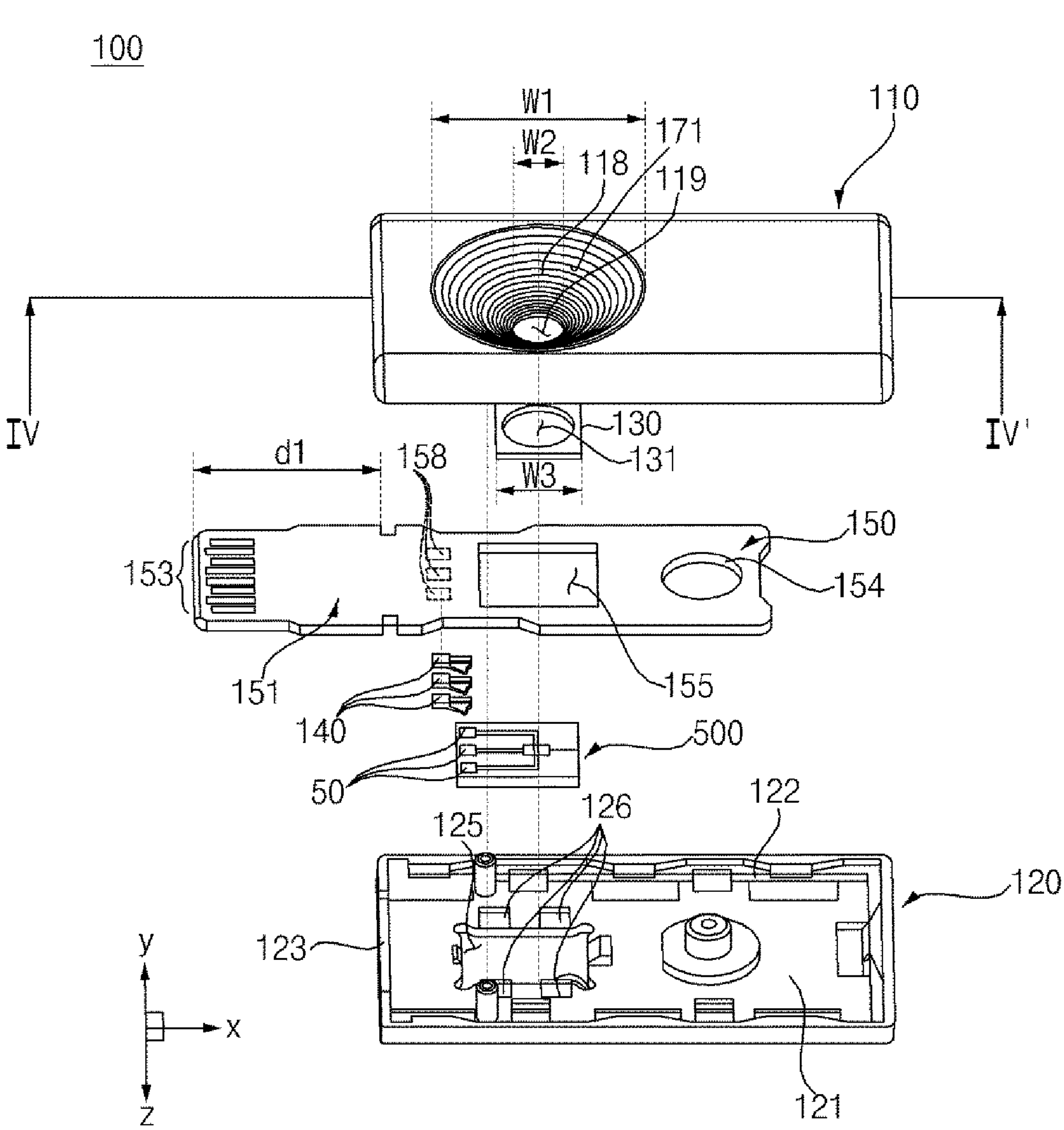
FIG. 13 is an exploded perspective view of another example of the biosensor cartridge of FIG. 1 according to an embodiment of the present disclosure.

At this time, the sealing part 130 can have a sealing opening 131 having a diameter W3 larger than the diameter W2 of the rear opening of the accommodating portion 119 as shown in FIG. 7 and FIG. 13, and the rear opening and the sealing opening 131 can be disposed to have a concentric circle. Accordingly, at the time of assembling, as shown in FIG. 7, the sealing part 130 is disposed outside the lower opening of the accommodating portion 119 to form a concave groove.

This is designed to avoid danger that the elastic sealing part 130 is pushed to the sensor area 530 by the compression of the sealing part 130 and covers the sensor area 530 in contact with the specimen, as a tolerance is set when the sealing part 130 is compressed.

As described above, it is possible to ensure the sealing of the specimen while securing the area of the sensor area 530 by adjusting the size of the sealing opening 131 of the sealing part 130 and the opening size of the accommodating portion 119.

Meanwhile, the sealing part 130 can be a closed cell type waterproof pad having elasticity but is not limited thereto.

Meanwhile, the connection pad 158 formed on the rear surface of the circuit board 150 is formed in the same number as the pad 511 of the biosensor chip 500, and a connecting member 140 is disposed for electrical and physical connection between the connection pad 158 of the circuit board 150 and the pad 511 of the biosensor chip 500.

As shown in FIG. 6, the connecting member 140 can be formed separately for each pad 158 and can be formed as a clip-type elastic contact piece. Such a connecting member 140 can be a C-clip or a spring terminal.

Each connecting member 140 can include a first surface in contact with the pad area 510 of the circuit board 150 and a second surface configured to be elastically deformable by being bent in the length direction of the first surface from one side surface of the first surface.

The first surface is formed to have a certain length and is in contact with the pad area 510 of the circuit board 150, and the second surface is in contact with the pad 511 of the lower sensor chip 500 and elastically deformed.

To this end, in the state where the connection pad 158 of the circuit board 150 and the first surface are in contact with each other through welding or soldering, when the circuit board 150 is disposed in the lower housing 120 in which the biosensor chip 500 is disposed, a bending portion is elastically deformed as pressure is applied vertically to the connecting member 140 by assembling the upper housing 110 and the lower housing 120.

At this time, the angle is changed so that the second surface is parallel to the first surface as a spring coupling portion is pushed into the inside of the second surface. Thus, the second surface is in contact with the pad 510 of the biosensor chip 500 to maintain a conducting state, so that physical coupling and electrical coupling occur simultaneously.

As described above, since the probe material in the biosensor chip 500 is not exposed to high temperature in a bonding process by performing electrical connection of the biosensor chip 500 with the circuit board 150 without a separate bonding process, it is possible to prevent a problem that protein modification occurs.

That is, in the presence of probe material vulnerable to heat due to the characteristics of the biosensor, the characteristics of the probe material can be maintained by excluding a heating process, and electrical connection between the biosensor chip 500 and the circuit board 150 becomes possible.

Meanwhile, on the rear surface 129 of the lower housing 120 of the biosensor cartridge 100, e.g., the rear surface 129 of the cartridge 100 exposed to the outside, a QR label 160 including a QR code in which sensor information including a product ID and a manufacturing serial number for genuine product certification of the biosensor cartridge 100 is stored is attached.

The QR code can be attached to the central area of the rear surface 129 of the lower housing 120 so that the rear surface 129 of the lower housing 120 of the cartridge 100 can be aligned over the second opening 293 which is the QR opening when the cartridge 100 is coupled with the external diagnostic device 200.

The QR code can include all sensor information for genuine product certification. As an example, the QR code can include biosensor chip 500 information and cartridge information as well as the product ID and manufacturing serial number. The information of the biosensor chip 500 can include the type of probe material activated in the biosensor chip 500, a disease to be diagnosed, a manufacturing date, a manufacturing location, and a manufacturing serial number of the biosensor chip 500. In addition, the cartridge information can include an assembly date, a test date, expiration date, and a sensor ID of the biosensor cartridge 100.

The stored QR code is read from the QR reading module 271 of the diagnostic device 200 at the same time when it is inserted into the diagnostic device 200, and a process for genuine product certification can be performed with the cloud server 400.

The biosensor cannot determine whether it is an imitation or not. Even if it is genuine, sensor errors are often found or decided from accumulated test data after manufacturing and sales. Therefore, a process of classifying the biosensor cartridge 100 in which an error has occurred is required before the test proceeds.

In the situation of the biosensor cartridge 100, it is possible to check an error including a current risk to a corresponding type of the biosensor cartridge 100 through such a certification procedure.

The biosensor cartridge 100 according to the present embodiment does not include a separate memory chip for storing sensor-specific information for such a certification procedure.

When such a memory chip is separately included, the size of the circuit board 150 increases, and the size of the housing 110, 120 increases according to the size of the circuit board 150. In addition, as the circuit of the circuit board 150 becomes complicated, the number of pins used in the connection terminal 153 increases, thereby causing problems in miniaturization and cost of the cartridge 100.

Like the biosensor cartridge 100 according to the present embodiment, by attaching a QR label 160 on which a QR code is printed to the rear surface of the housing, such a memory chip can be replaced, and the time difference between reading of the sensor result and certification can be minimized by reading the QR code almost simultaneously with the coupling of the cartridge 100 and the diagnostic device 200.

Such a QR code can be prevented from being arbitrarily attached and detached by attaching it as a security label 160 such as a VOID label on the rear surface of the lower housing 120.

In such a biosensor cartridge 100, in a state in which the biosensor chip 500 is placed in the lower housing 120, the upper housing 110 coupled to the circuit board 150 to which the connecting member 140 is attached is pressed for assembling with the lower housing 120, so that the biosensor chip 500 and the circuit board 150 are physically and electrically attached and fixed.

In this situation, the attachment of the upper housing 110 and the lower housing 120 can be further strengthened by performing fusion on an edge attachment area of the upper housing 110 and the lower housing 120.

Such fusion can be performed by ultrasonic fusion, but is not limited thereto, and can be performed through a separate adhesive member.

The edge attachment area formed as described above is continuously formed in the entire edge excluding an open portion through which the connection terminal 153 protrudes, e.g., in the distal end of the side surfaces of the upper housing 110 and the lower housing 120, thereby preventing moisture or foreign substances from penetrating into the interior from the outside.

Figure 14:
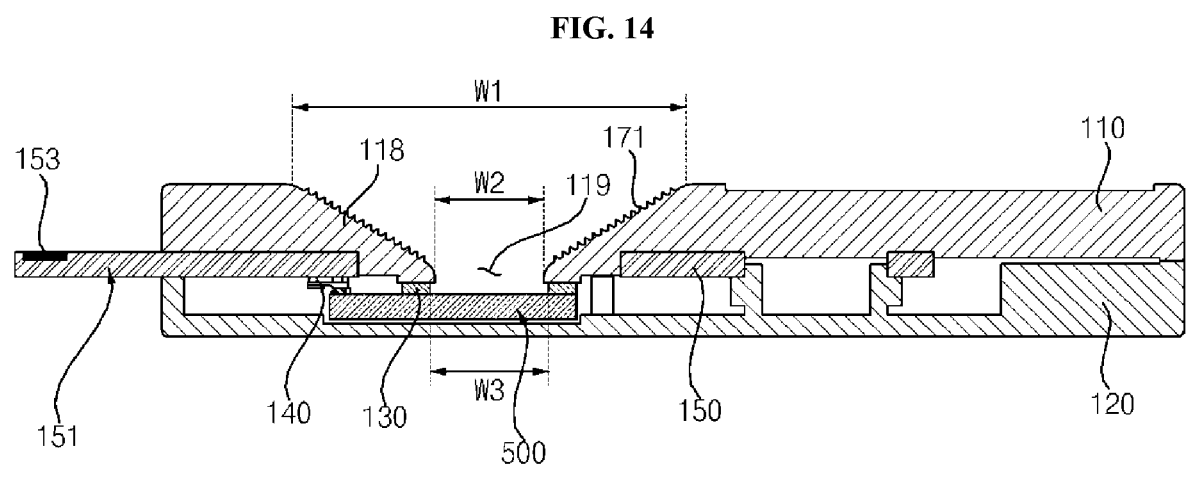

Such a biosensor cartridge 100 can be changed to a configuration shown in FIGS. 13 and 14.

The sensor cartridge 100 according to a second embodiment can be configured as shown in FIGS. 13 and 14.

FIG. 13 is an exploded perspective view of another example of the biosensor cartridge 100 of FIG. 1, and FIG. 14 is a cross-sectional view of the biosensor cartridge 100 of FIG. 13 taken along line IV-IV'.

In the biosensor cartridge 100 of FIGS. 13 and 14, since the configuration of the lower housing 120, the biosensor chip 500, and the circuit board 150 is the same as that of the biosensor cartridge 100 of FIGS. 6 and 7, and the attachment configuration of the upper housing 110 and the lower housing 120 is also the same as that of FIG. 10, a description thereof is omitted.

In the biosensor cartridge 100 of the second embodiment, the accommodating portion 119 can be formed differently from the first embodiment.

Referring to FIGS. 13 and 14, in the biosensor cartridge 100 according to the second embodiment, the accommodating portion 119 for accommodating the specimen in the upper housing 110 and guiding the specimen to the sensor area of the lower biosensor chip 500 is formed.

Specifically, the accommodating portion 119 is a space for inducing a reaction with the exposed sensor area 530 by accommodating a test target specimen in a fluid state, e.g., in a liquid state, and the accommodating portion 119 is concavely recessed from the upper surface to form a conical passage, e.g., a channel or funnel, the diameter of which becomes narrower as it approaches the sensor area 530.

Accordingly, the accommodating portion 119 is formed to have an inclined surface 118 such that the diameter W1 of the opening of the upper surface is larger than the diameter of the opening W2 at the distal end of the accommodating portion 119.

In the accommodating portion 119, since the diameter W1 of the opening of the upper surface is expanded to be wider than the area of the biosensor chip 500, the difference between the diameter W1 of the opening of the upper surface and the diameter W2 of the opening at the distal end of the accommodating portion 119 is significantly large.

For example, the diameter W1 of the opening of the upper surface can satisfy two to three times the diameter W2 of the opening at the distal end of the accommodating portion 119.

As the difference between the diameter W1 of the opening in the upper surface and the diameter W2 of the opening at the distal end of the accommodating portion 119 becomes larger, the accommodating volume of the accommodating portion 119 increases, so that a large amount of specimen can be accommodated.

Figure 15:
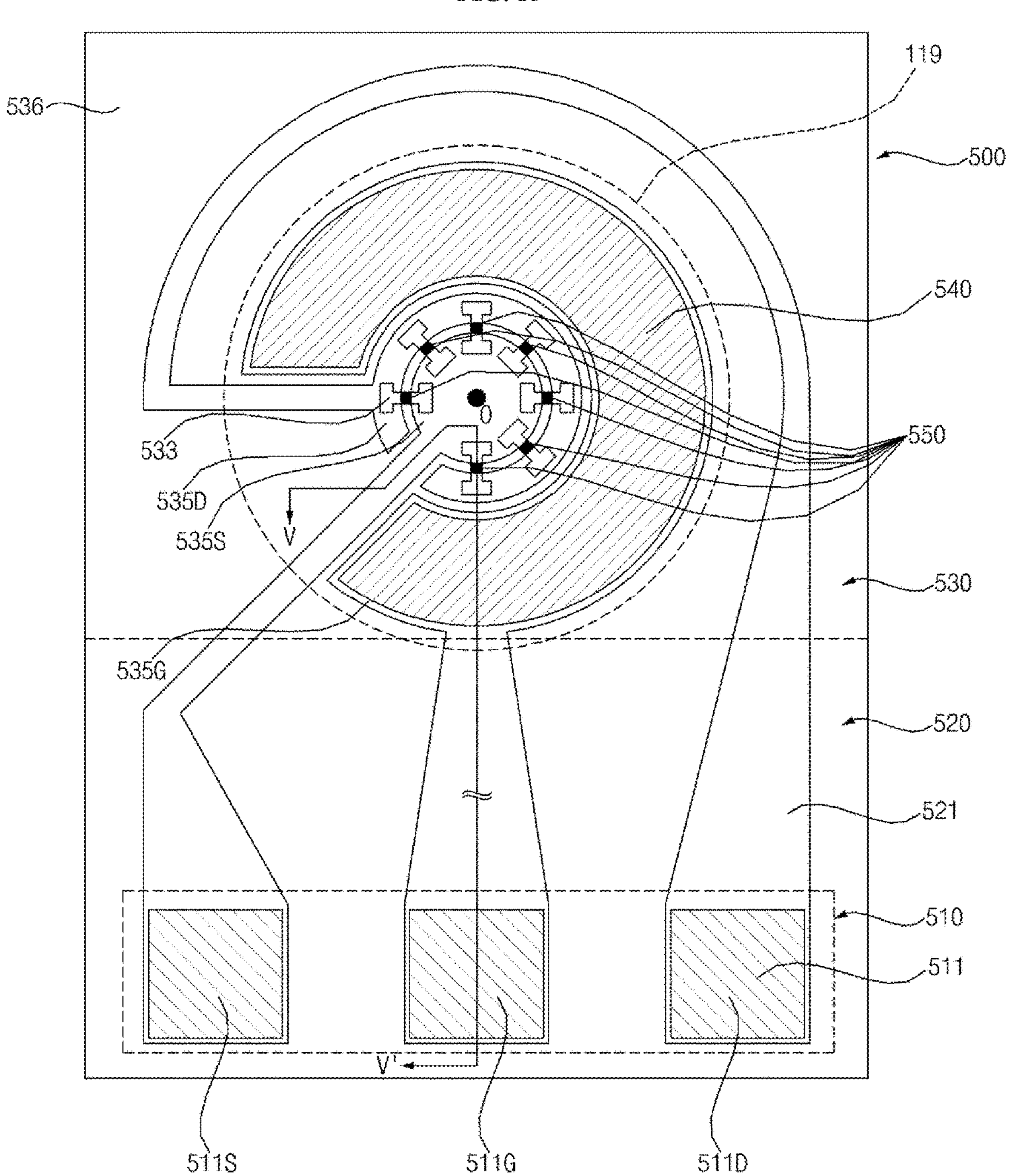
FIG. 15 is a top view of one example of a sensor chip applicable to the biosensor cartridge of FIGS. 6 to 14 according to an embodiment of the present disclosure.

At this time, the inclination angle of the inclined surface 118—the angle of the inclined surface with respect to the horizontal direction in which the biosensor chip 500 is placed when viewed from the cross section in FIG. 15—can be uniform but can have an inflection point.

That is, the inclination angle increases as it approaches the sensor area 530, it forms a verticality in the outermost area closest to the sensor area 530, so that it can be changed to a cylindrical passageway.

As described above, since the accommodating portion 119 has the inclined surface 118, a concave groove having a depth that is a height from the upper surface of the upper housing 110 to the channel area is formed. A specimen is collected in the groove to induce a reaction with the probe material in the sensor area 530.

As described above, the biosensor cartridge 100 accommodates the biosensor chip 500 inside the housing 110, 120, and is provided to accommodate the circuit board 150 for transmitting the detection information of the biosensor chip 500 to the external diagnostic device 200.

Since the super water repellent pattern structure of FIGS. 8 to 12C described above is also applied to the inclined surface 118 of FIGS. 13 and 14, and the descriptions thereof are the same, they will be omitted.

In what follows, a biosensor chip 500 according to the present embodiment will be described with reference to FIGS. 15 to 18.

Figure 16:
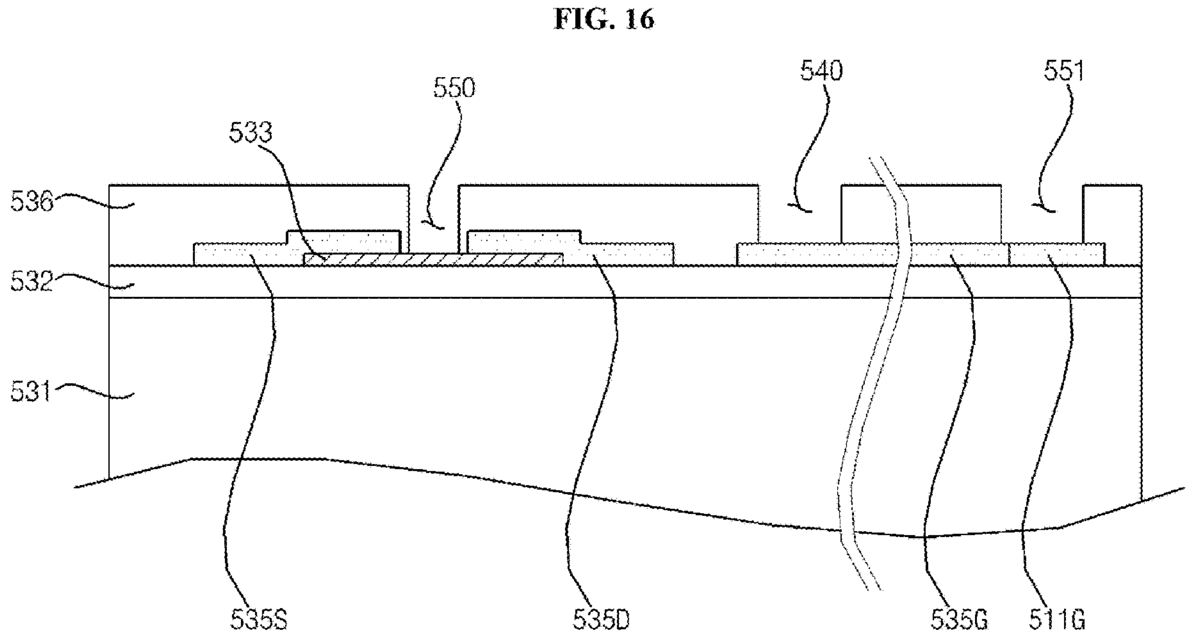
FIG. 16 is a cross-sectional view of the sensor chip of FIG. 15 taken along a line V-V' according to an embodiment of the present disclosure.
Figure 17A:
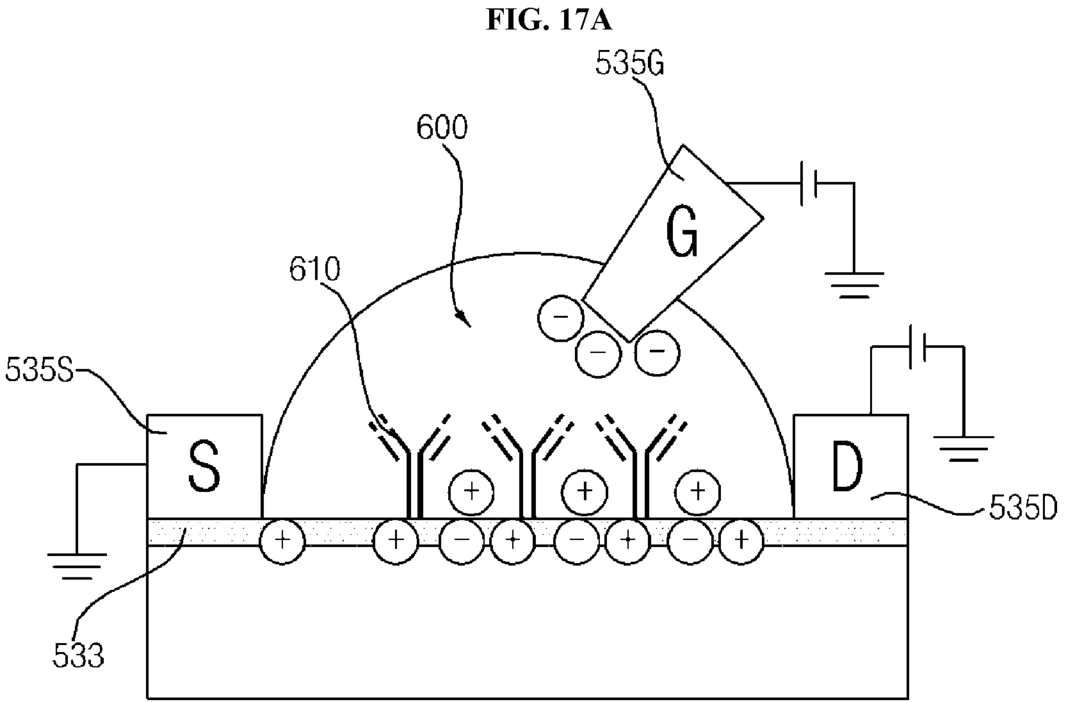

FIG. 15 is a top view of one example of a biosensor chip 500 applicable to FIGS. 6 to 14, FIG. 16 is a cross-sectional view of the biosensor chip 500 of FIG. 15 taken along a line V-V', FIGS. 17A and 17B are schematic diagrams showing the response of the biosensor chip 500 of FIG. 15 according to target material, and FIG. 18 is a graph showing a change in the output current of the sensor chip according to FIGS. 17A and 17B.

The biosensor chip 500 detects a target material from a specimen introduced into the inside by the accommodating portion 119 of the biosensor cartridge 100, and transmits an electrical signal generated by reacting with the detected target material to the pad 158 of the circuit board 150 through the electrode pad 511.

For example, the specimen can refer to saliva, a body fluid including sweat, blood, a solution diluted with serum or plasma, and the like, as a biological material.

The biosensor chip 500 is a semiconductor-based sensor chip 500 and can be manufactured as a biosensor chip 500 to which graphene is applied.

The biosensor chip 500 can have various sizes depending on the type of target material, the number of target materials, and the size of the cartridge 100 and can be designed to have a size of, for example, 6×6 mm or 6×8 mm.

Referring to FIGS. 15 and 16, the biosensor chip 500 according to the present embodiment can have a rectangular shaped plane, have a front surface on which a sensor area 530 exposed to the outside through the accommodating portion 119 is formed, and be partitioned into a pad area 510 which is spaced apart from the sensor area 530 and connected to the pad 158 of the circuit board 150 through the connecting member 140 and a connection portion 520 connecting the sensor area 530 and the pad area 510.

A probe material, for example, an antigen, an antibody, and an enzyme, which detects a target material from a contacted specimen and reacts with or attaches to the target material to generate an electrical signal, is attached to the sensor area 530.

When the sensor area 530 comes into contact with a specimen, it interacts with a target material included in the specimen to generate an electrical signal. Accordingly, the external diagnostic device 200 connected to the biosensor 100 can analyze an electrical signal generated from the biosensor 100 to detect the presence or concentration of the target material.

The sensor area 530 includes a transistor structure, and has a structure where probe material is attached to a channel area 550 of the transistor.

Specifically, the sensor area 530 includes a plurality of circular or ring-shaped electrodes 535S, 535D, and 535G forming a concentric circle, and a plurality of channel areas 550 are formed between the plurality of electrodes 535S, 535D, and 535G, particularly, between the source electrode 535S and the drain electrode 535D.

An insulating layer 532 is formed on the semiconductor substrate 531, and the insulating layer 532 can be formed of oxide or nitride. When the semiconductor substrate 531 is a silicon substrate, the insulating layer 532 can be formed of silicon oxide or silicon nitride and can be formed by various methods. For example, a silicon oxide layer can be formed on the surface through heat treatment.

A plurality of channels 533 are formed on the insulating layer 532 to be spaced apart from each other.

A plurality of channels 533 are disposed by being spaced apart by a predetermined distance from the circle center O of the sensor area 530, and a central area is exposed to form the channel area 550.

The plurality of channels 533 are disposed by being spaced apart from each other on the circumference of an imaginary circle having a radius of a predetermined distance from the center O of the circle. For example, the plurality of channels 533 can be arranged similar to spokes on a wheel.

The plurality of channels 533 can be disposed to be spaced apart by the same angle; for example, as shown in FIG. 15, seven channels 533 can be formed, and each channel 533 can be spaced apart from the other at an angle of 45 degrees.

Alternatively, five channels 533 can be disposed so that each channel 533 can be spaced apart at an angle of 60 degrees.

One channel 533 can be patterned in a specific shape and can be formed by a semiconductor material but can also be formed by a graphene-based material that is highly reactive as a highly conductive material.

The channel 533 includes an area overlapping with the source electrode and the drain electrode 535S, 535D and a channel area 550 exposed to the outside through the accommodating portion 119 between two overlapping areas.

The channel area 550 can have lower resistance in the channel area 550 as the channel 533 is formed in a dumbbell shape or an I-shape to have a narrower width than the overlapping area as shown in FIG. 15 but is not limited to the specific situation; instead, the channel area 550 can be formed in a bar type to have the same width from the overlapping area to the channel 533.

A source electrode 535S having the shape of the smallest circle can be formed at the center O of the circle of the sensor area 530. The source electrode 535S can be formed to have the smallest diameter and to overlap one end of the channel 533; the source electrode 535S simultaneously overlaps a plurality of channels 533 and applies a source voltage simultaneously to a plurality of channels 533.

A drain electrode 535D can be formed outside the channel area 550 to be spaced apart from the source electrode 535S.

The drain electrode 535D can be formed in a ring shape and is formed along the circumference of an imaginary circle that surrounds the channel area 550 and has a larger diameter than that of the channel area 550.

The drain electrode 535D can also overlap the plurality of channels 533 simultaneously to receive current from the plurality of channels 533 simultaneously.

One end of the drain electrode 535D is cut to form a passage through which the connection portion 521 of the source electrode 535D passes (e.g., forming a cut area or a notched area). For example, a connection portion of the source electrode 535S passes through the cut area in the notched ring shape of the drain electrode 535D. In other words, when viewed from above in a plan view, the drain electrode 535D and the source electrode 535S can form coupled arrangement similar to a ball and socket joint.

A gate electrode 535G is formed along the circumference of an imaginary circle having a larger diameter surrounding the drain electrode 535D.

The gate electrode 535G can have the largest area and occupy ½ to ⅔ of the sensor area 530. The gate electrode 535G is formed to be spaced apart from the source electrode, the gate electrodes 535S and 535D, and the channel area 550.

The gate electrode 535G also forms a passage so that the connection portions 521 of the grain electrode and the source and drain electrodes 535S and 535D are connected to the pad 511, and one end of the gate electrode 535G is disconnected. For example, the gate electrode 535G can also include a cut out area or a notched portion (e.g., a "C" shape) for wiring connections to the source and drain electrodes 535S and 535D. For example, the gate electrode 535G can have a letter "C" shape in which both of the connection portions 521 of the source electrode and the drain electrode 535S, 535D can fit into the opening or mouth of the letter "C" shape.

The electrodes 535S, 535D, and 535G of the sensor area 530 designed as shown in FIG. 15 are formed in the same layer.

Accordingly, the source electrode, the drain electrode, and the gate electrodes 535S, 535D, and 535G are all formed in the same layer and formed in one process.

For example, the source electrode, the drain electrode, and the gate electrode 535S, 535D, and 535G can be respectively formed by forming an electrode layer (e.g., a same metal layer) and simultaneously patterning a corresponding electrode layer.

Thus, a process step can be reduced, and a process time and cost can be reduced by simultaneously forming three electrodes 535S, 535D, and 535G that do not overlap each other.

The metal layer can be formed of at least one of Ni, Zn, Pd, Ag, Cd, Pt, Ga, In, and Au, but is not limited thereto.

A passivation layer 536 is formed on the electrodes 535S, 535D, and 535G.

The passivation layer 536 is formed on the entire biosensor chip 500 to protect the sensor area 530 and the electrodes 535S, 535D, and 535G.

The passivation layer 536 can be formed of a material resistant to moisture and can be formed of, for example, an oxide layer, a nitride layer, or a carbide layer.

In addition, the passivation layer 536 can be applied with a polymer resin but is not limited thereto.

The passivation layer 536 exposes only the upper portion 551 of the plurality of channel areas 550, the gate electrode 540, and the plurality of pads 511 in the biosensor chip 500; and covers all other areas.

Accordingly, the area exposed by the passivation layer 536 is very limited.

In particular, in the sensor area 530, only the gate electrode 535G and the channel area 550 are exposed to induce a reaction by directly contacting the specimen.

In the pad area 510, each pad 511 is exposed in an insulated state, and electrically in contact with each pad 158 of the circuit board 150 through a connecting member through an upper connecting member 140.

As shown in FIG. 17A, probe material 610 is attached to each of the channel areas 550 exposed as described above to activate the sensor.

The probe material 610 is a material that reacts specifically to a target material to be detected by the sensor. When the target material is an antigen, an antibody can be attached thereto, or when the target material is an antibody, an antigen can be attached thereto.

When the channel 533 is formed of graphene, a linker material can be attached for smooth connection between the probe material 610 and graphene, and a process of attaching the probe material 610 after attaching a linker material on graphene is defined as an activation process.

The linker material is different depending on the material constituting the channel 533 and the probe material 610, and in the situation of graphene, it can be a polymer structure having a nano size, for example, can be formed of at least one of polyurethane, polydimethylsiloxane, Norland Optical Adhesives NOA, epoxy, polyethylene terephthalate, polymethyl methacrylate, polyimide, polystyrene, polyethylene naphthalate, polycarbonate, and combinations thereof.

In addition, the linker material can be formed of a combination of polyurethane and NOA (e.g., NOA 68). However, the linker material is not limited thereto, and can be made of various polymers having flexibility.

An electrical detection signal according to a reaction of the biosensor chip 500 can be described with reference to FIGS. 17A and 17B.

When the target material does not exist in the specimen as shown in FIG. 17A, the source electrode 535S receives a source voltage and the gate electrode 535G receives a gate voltage by the voltage applied to each pad 511.

The gate electrode 535G is exposed to the accommodating portion 119 and comes into contact with the specimen provided from the outside to apply a bias voltage to the specimen. Therefore, the specimen exists in a state of being partially charged with respect to the voltage of the gate electrode 535G.

At this time, the drain current Ids read from the drain electrode 535D is as shown in FIG. 18.

That is, when there is no target material reacting with the probe material 610 in the specimen 600, the drain current Ids has a first value I1, which is defined as a reference current.

At this time, as shown in FIG. 17B, when the target material 650 does exist in the specimen 600, the channel 533 is charged with a specific carrier as the target material 650 reacts with the probe material 610. For example, as shown in FIG. 17B, a depletion state in which charges are accumulated in the channel 533 can proceed.

Accordingly, as the drain current Ids read from the drain electrode 535D increases, it has a second value I2 of FIG. 18, thus indicating a positive reading for the presence of the target material 650.

At this time, the amount of accumulated charge is proportional to the area of the channel 533. Thus, when the number of channel 533 is one, the drain current Ids has a second value I2. When the number of channels 533 is two or more, the drain current Ids has a third value I3 greater than the second value I2. When the number of channels 533 is three or more, the drain current Ids can have a value greater than the third value I3, thus indicating a positive reading for the presence of the target material 650. Accordingly, the value of the drain current Ids read from the drain electrode 535D is amplified by the multiple channels.

At this time, even when one channel 533 does not operate (e.g., if one channel is defective) as the plurality of channels 533 are spaced apart from each other, the existence of the target material can be recognized by causing the drain current Ids to increase or decrease in another channel 533. Thus, redundancy can be provided by the multiple channels.

As described above, the graphene channel sensor chip 500 has a multi-channel structure having a plurality of channels spaced apart from each other, thereby amplifying a drain current and compensating for a malfunctioning channel.

In such a biosensor chip 500, both the gate electrode 535G and the channel area 550 can be exposed by the distal end opening of the accommodating portion 119 having a circle larger than the circumference of the gate electrode 535G.

In addition, the plurality of channel areas 550 are formed to be spaced apart at the same angle and at the same distance from the center O of the sensor area 530 opened by the accommodating portion 119 such that the specimen is uniformly contacted and formed in a shape surrounding the source and drain electrodes 535S and 535D in order to dispose the channel 533 between the source and drain electrodes 535S and 535D, thereby optimizing a structure.

FIG. 15 shows electrode connection portion 521 connected from one end of each electrode 535S, 535D, and 535G to the pad 511; since each electrode connection portion 521 is made of the same metal layer as the electrodes 535S, 535D, and 535G, the connection portions do not overlap each other.

FIG. 15 illustrates a situation in which the pad 511 is formed in a line on one end of the biosensor chip 500, but the present disclosure is not limited to the specific situation.

The design of the biosensor chip 500 can be variously changed as long as the transistor in which the gate electrode 535G and the plurality of channels 533 are exposed is maintained in the accommodating portion 119.

Accordingly, the position of the pad 511 can also be variously changed. However, the positions of the connecting member 140 and the connection pad 158 of the circuit board 150 are also changed according to the change in the position of the pad 511.

Figure 19:
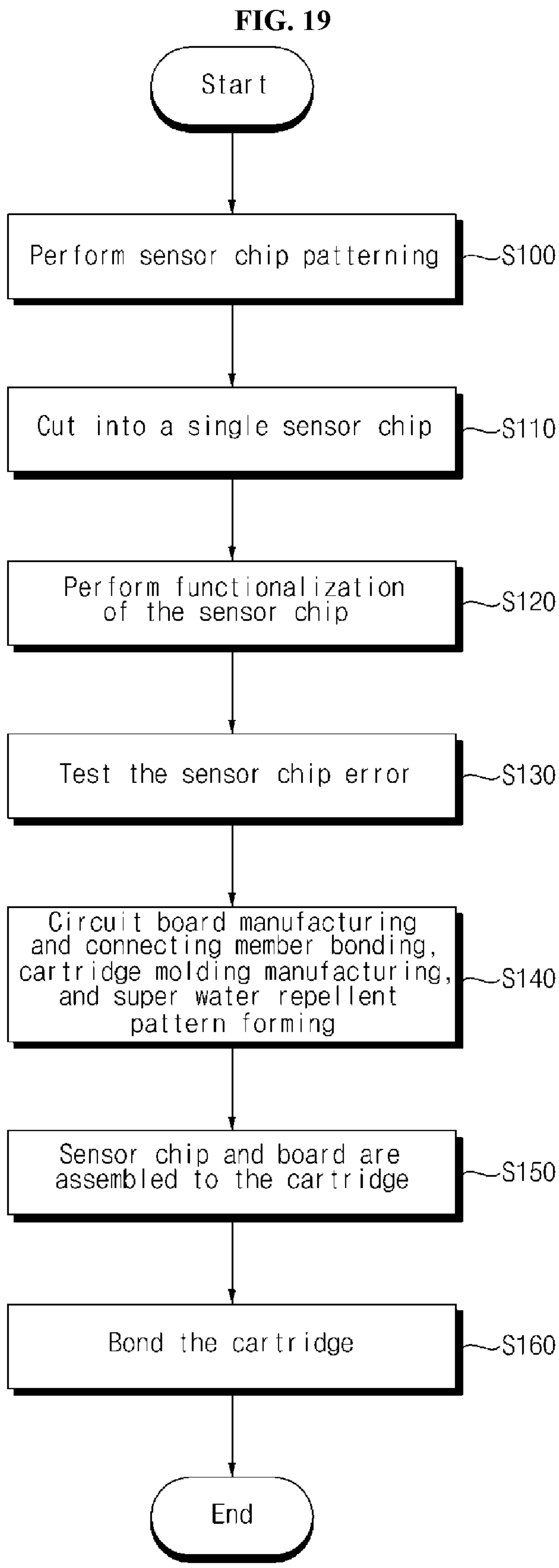
FIG. 19 is a flowchart illustrating a manufacturing process of the biosensor cartridge of FIG. 5 according to an embodiment of the present disclosure.

The biosensor cartridge 100 accommodating the graphene-based multi-channel sensor chip 500 is manufactured through the process shown in FIG. 19.

Hereinafter, a method of manufacturing a graphene-based multi-channel sensor chip 500 according to the present disclosure will be described with reference to FIG. 19.

Referring to FIG. 19, firstly, patterning of the biosensor chip 500 for manufacturing the biosensor chip 500 is performed on a semiconductor wafer S100.

The manufacturing of the biosensor chip 500 is a process for manufacturing the biosensor chip 500 of FIGS. 15 and 16, and an insulating layer 532 made of oxide or nitride is formed on the semiconductor substrate 531.

When the semiconductor substrate 531 is a silicon substrate, the insulating layer 532 can be formed of silicon oxide or silicon nitride and can be formed by various methods. For example, a silicon oxide layer can be formed on the surface through heat treatment.

A plurality of channels 533 are formed on the insulating layer 532 to be spaced apart from each other.

At this time, one semiconductor wafer is designed to simultaneously manufacture a plurality of unit biosensor chips 500 and can perform channel patterning for manufacturing the plurality of unit biosensor chips 500 S100.

A channel layer is patterned with a plurality of channels 550 designed for each unit sensor chip 500.

For example, when the plurality of channels 550 are formed of graphene, the graphene is stacked on the insulating layer and then patterned to form a plurality of channels 550 spaced apart from each other in the area of the unit sensor chip 500.

Next, at least one metal layer among Ni, Zn, Pd, Ag, Cd, Pt, Ga, In, and Au for forming the electrode 535S, 535D, 535G as shown in FIG. 15 is stacked, and the metal layer is patterned to simultaneously form the source electrode, the drain electrode, and the gate electrode 535S, 535D, 535G, the pad 511 connected to each electrode, and the connection portion 521 for connecting them. The passivation layer 536 is formed on the electrode 535S, 535D, and 535G, and patterning is performed to expose only the plurality of channel areas 550, the gate electrode 540, and the plurality of pads 511.

When a plurality of unit biosensor chips 500 are generated on one semiconductor wafer as described above, a cutting process of cutting the plurality of unit biosensor chips 500 into a single biosensor chip 500 is performed (S110).

The cutting process can be performed by laser scribing, and laser scribing can be performed together with a physical cutting process.

A single sensor chip 500 cut from the plurality of unit biosensor chips 500 is defined as the biosensor chip 500 of FIG. 15, and functionalization of the biosensor chip 500 is performed (S120).

The functionalization of the biosensor chip 500 is defined as a process of attaching probe material that performs a specific reaction to a target material to be detected by each sensor to an exposed channel area of each biosensor chip 500.

For the functionalization of the biosensor chip 500, when the channel 533 is formed of graphene, a linker material can be attached for a smooth connection between the probe material 610 and graphene, a process of attaching the probe material 610 after attaching the linker material on the graphene is performed.

The linker material is different depending on the material constituting the channel 533 and the probe material 610, and in the situation of graphene, it can be a polymer structure having a nano size, for example, can be formed of at least one of polyurethane, polydimethylsiloxane, Norland Optical Adhesives NOA, epoxy, polyethylene terephthalate, polymethyl methacrylate, polyimide, polystyrene, polyethylene naphthalate, polycarbonate, and combinations thereof.

In addition, the linker material can be formed of a combination of polyurethane and NOA (e.g. NOA 68). However, the linker material is not limited thereto, and can be made of various polymers having flexibility.

When the functionalization of the biosensor chip 500 is completed, a test process of the biosensor chip 500 is performed (S130).

In the test of the biosensor chip 500, the biosensor chip 500 is injected into a test equipment and the test equipment is connected to the exposed pad 511, so that the alignment and electrical signals of the pad 511 are read to measure a resistance.

Thus, a physical test on whether patterning is performed accurately according to a design and a functional test on whether electrical connection is performed can be simultaneously performed.

In addition, the basic resistance value of each sensor chip 500 is received, and a failure can be determined according to whether a corresponding basic resistance value is within a certain range.

When such an error check is finished, the failure sensor chip is classified and only the biosensor chip 500 that passed the check can be used as a valid chip.

Meanwhile, the circuit board 150 can be manufactured through a separate process. As described above, the circuit board 150 fabricated by cutting and punching a base member, which is the base material of the circuit board 150, according to the design of the circuit board 150, forming a circuit pattern in one side of the base member, and attaching a supporting plate 159 on the other side of the circuit board 150.

In this situation, one side of the circuit board 150 is disposed as a rear surface, and the connection pad 158, which is a part of the circuit pattern, is exposed on the rear surface.

The connecting members 140 are respectively attached to the exposed connection pad 158 according to a preset number (S140).

The bonding of the pad 158 and a first surface of the connecting member 140 can be performed by soldering to simultaneously satisfy the electrical and physical attachment. Accordingly, a second surface of the connecting member 140 is maintained as a free end.

Meanwhile, the upper housing 110 and the lower housing 120 can be manufactured through a separate process.

Separate molds can be manufactured respectively for the upper housing 110 and the lower housing 120 to perform a molding process; at this time, when the upper housing 110 is molded, the mold can be manufactured to form the super water-repellent pattern structure 171 together on the inclined surface of the accommodating portion 119 of the upper housing 110.

In this way, when a resin material such as polycarbonate is injected into the mold, and then the mold is removed in the vertical direction, the upper housing 110 in which the super water-repellent pattern structure 171 is formed on the inclined surface 116 is manufactured.

Therefore, the super water repellent pattern structure 171 can be formed by one injection without a separate laser ablation process, and a super water repellent coating surface 170 can be selectively formed on the accommodating portion 119 of the upper housing 110.

Next, in a state in which the biosensor chip 500 is disposed in the area of the biosensor chip 500 of the lower housing 120 of the cartridge 100 and the circuit board 150 is placed thereon, the upper housing 110 is pressed, so that the second surface of the connecting member 140 is fixed in a state of being bonded to the pad 511 of the biosensor chip 500 (S150).

Accordingly, electrical connection and physical connection between the circuit board 150 and the biosensor chip 500 are simultaneously achieved.

In this state, the ends of the side surfaces of the lower housing 120 and the upper housing 110 of the cartridge 100 are ultrasonically fused to induce the melting of some resin and harden the melted resin to integrate the cartridge 100 (S160). The manufacturing is completed in such a way that the physical separation of the upper housing 110 and the lower housing 120 is impossible by the fusion.

Through such a manufacturing process, failure of the biosensor chip 500 is firstly filtered and then assembling is performed. In the assembling step, a high-temperature process by wire bonding is not applied, so that the functionalized sensor chip 500 is prevented from being deteriorated due to heat.

In addition, since a process for protecting a device by performing plastic molding is not added after wire bonding of the biosensor chip 500, deterioration of the probe material of the biosensor chip 500 due to high temperature is prevented.

Figure 20:
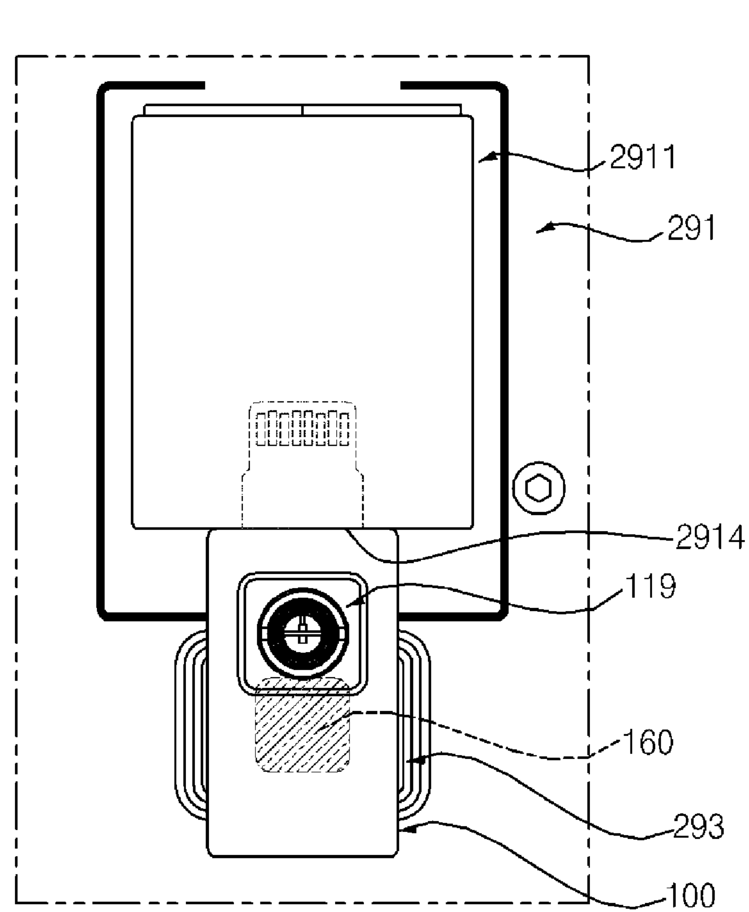
FIG. 20 shows a combination of a biosensor cartridge and a biosensor diagnostic device in the biosensor system of FIG. 1 according to an embodiment of the present disclosure.

The biosensor cartridge 100 accommodating the graphene-based multi-channel sensor chip 500 manufactured as described above performs the certification of the sensor cartridge 100 and the diagnosis of the specimen by inserting the connection terminal 153 of the cartridge into the insertion hole 2914 of the insertion module 2911 of the diagnostic device of FIG. 3 as shown in FIG. 20.

FIG. 20 is a coupling diagram in which the biosensor cartridge 100 is coupled to the biosensor diagnostic device 200 in the biosensor system of FIG. 1.

As shown in FIG. 20, when a test target specimen is received in the accommodating portion 119 of the biosensor cartridge 100 in the biosensor system 10 according to the present embodiment, the connection terminal 153 of the biosensor cartridge 100 is inserted into the insertion hole 2914 of the cartridge insertion module 2911 of the biosensor diagnostic device 200.

As described above, the specimen can be a body fluid, such as saliva or sweat, or blood.

When a plurality of insertion holes 2914 are disposed, the connection terminal 153 is inserted into the corresponding insertion hole 2914 of a type matching the type of the connection terminal 153.

The insertion of the cartridge connection terminal 153 can be performed in the same manner as the insertion of the USB memory as the cartridge connection terminal 153 is similar to the USB terminal.

As described above, when the biosensor cartridge 100 and the biosensor diagnostic device 200 are coupled for analysis, the state shown in FIG. 20 is maintained.

That is, the accommodating portion 119 in which the test targeting specimen is accommodated is located outside the diagnostic device 200 and transmits an electrical signal in a state in which only the connection terminal 153 is inserted into the diagnostic device 200 through the insertion hole 2914.

The rear surface 129 of the lower housing 120 of the cartridge 100 faces the front panel 291, the QR label 160 attached to the rear surface 129 of the lower housing 120 is aligned with the QR opening 293 of the front panel 291, and the QR reading module 271 is turned on so that the camera reads the QR code of the QR label 160 of the rear surface 129 of the cartridge 100 on the QR opening 293. For example, a camera can be located under the end portion of the cartridge 100 for reading the QR code (e.g., see FIG. 1, FIG. 3 and FIG. 20).

The operator 250 decodes the QR information to extract sensor information stored as QR information. In this situation, the sensor information can include the biosensor chip 500 type, linker information, probe material information, product ID, board ID, manufacturer information, manufacturing date, assembly date, expiration date, test date, manufacturing number, and the like.

The operator 250 can perform a certification of the biosensor cartridge 100 by at least one cloud server 400 connectable through the wireless communication module 261.

When the biosensor cartridge 100 is genuine, the correction data is downloaded from the cloud server 400 (S60), the cartridge insertion module 2911 is driven to read the detection signal of the cartridge connection terminal 153 from the sensor converter 240, the signal conversion amplifier 210, and the signal filter 220.

At this time, the gate voltage and the source voltage are transmitted to the cartridge 100 through the sensor controller 260, and the drain current that is changed accordingly is read from the signal conversion amplifier 210.

Such read drain current value is amplified, and digitized after noise is removed, and transmitted to the operator 250.

A detection signal is decoded by executing a stored algorithm with respect to the drain current value which is the transmitted digitized detection signal, thereby reading whether the target material exists in the specimen currently accommodated in the cartridge 100.

At this time, the operator 250 downloads the correction data for a corresponding cartridge from the cloud server 400 after genuine product certification, and accordingly upgrades a corresponding algorithm, so that the optimized algorithm for the accumulated results of the same type of cartridge can be applied to the analysis.

The operator 250 reads the detection signal by performing the upgraded algorithm and transmits the result to the display module 295 for visualization or display.

In addition, it can operate to transmit a corresponding reading result to the cloud server 400, and transmit to a connected user terminal 300, so that a user can be notified by a designated user terminal 300.

The biosensor is not easy to determine whether it is an imitation. Even if it is genuine, sensor errors are often found from test data accumulated after manufacturing and sales. Therefore, a process of classifying the biosensor cartridge 100 in which an error has occurred is required before the test proceeds.

The biosensor system of the present embodiment can check an error including a current risk to a corresponding type of the biosensor cartridge 100 through such a certification procedure.

In addition, as the insertion of cartridge 100 and the genuine product certification are performed simultaneously, certification is performed by using a separate QR reader, and then the certified cartridge is applied to the diagnostic device 200 so that two-step operation of diagnosis can be merged into one operation. Therefore, the user's convenience is increased, and the genuine product certification of cartridge and the cartridge diagnosis are performed almost simultaneously and proceeded in a state where the cartridge inserted, so that the diagnosis result of a corresponding cartridge and the information of the cartridge are not mixed and can be clearly matched.

Figure 21A:
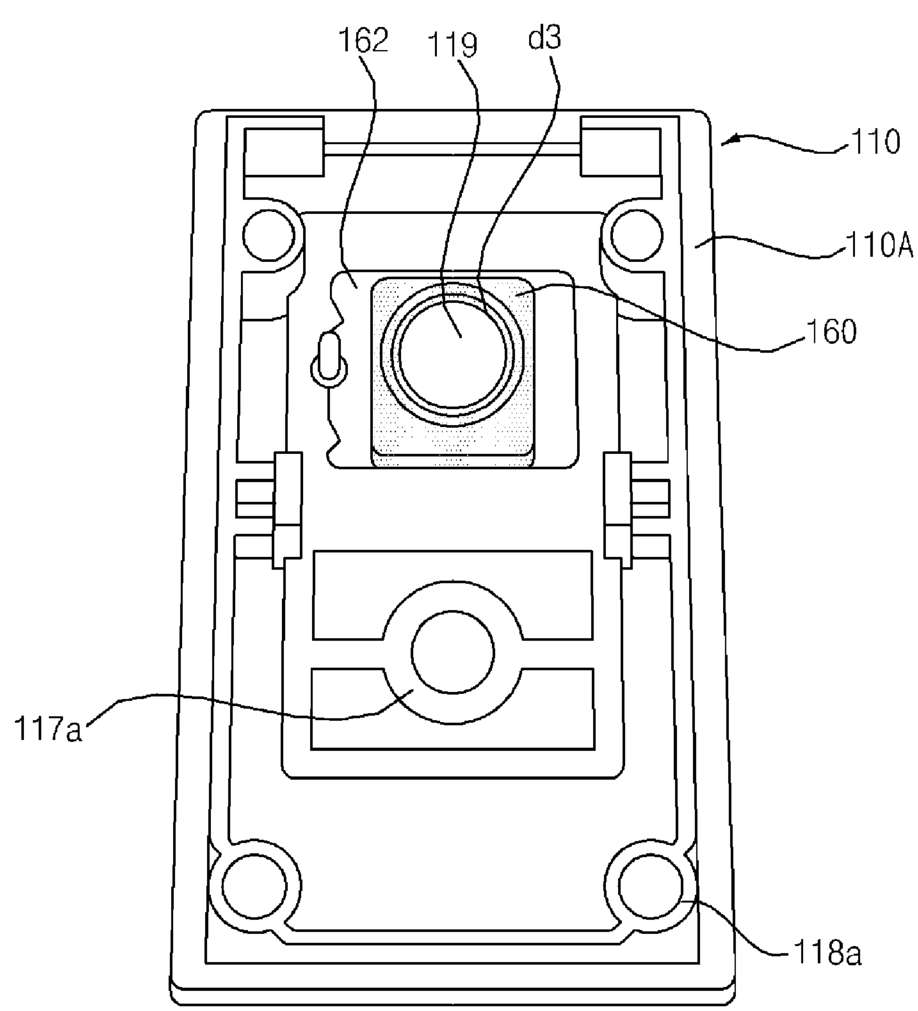
FIGS. 21A and 21B are internal top and cross-sectional views of another example of the biosensor cartridge of FIG. 1 according to an embodiment of the present disclosure.
Figure 21B:
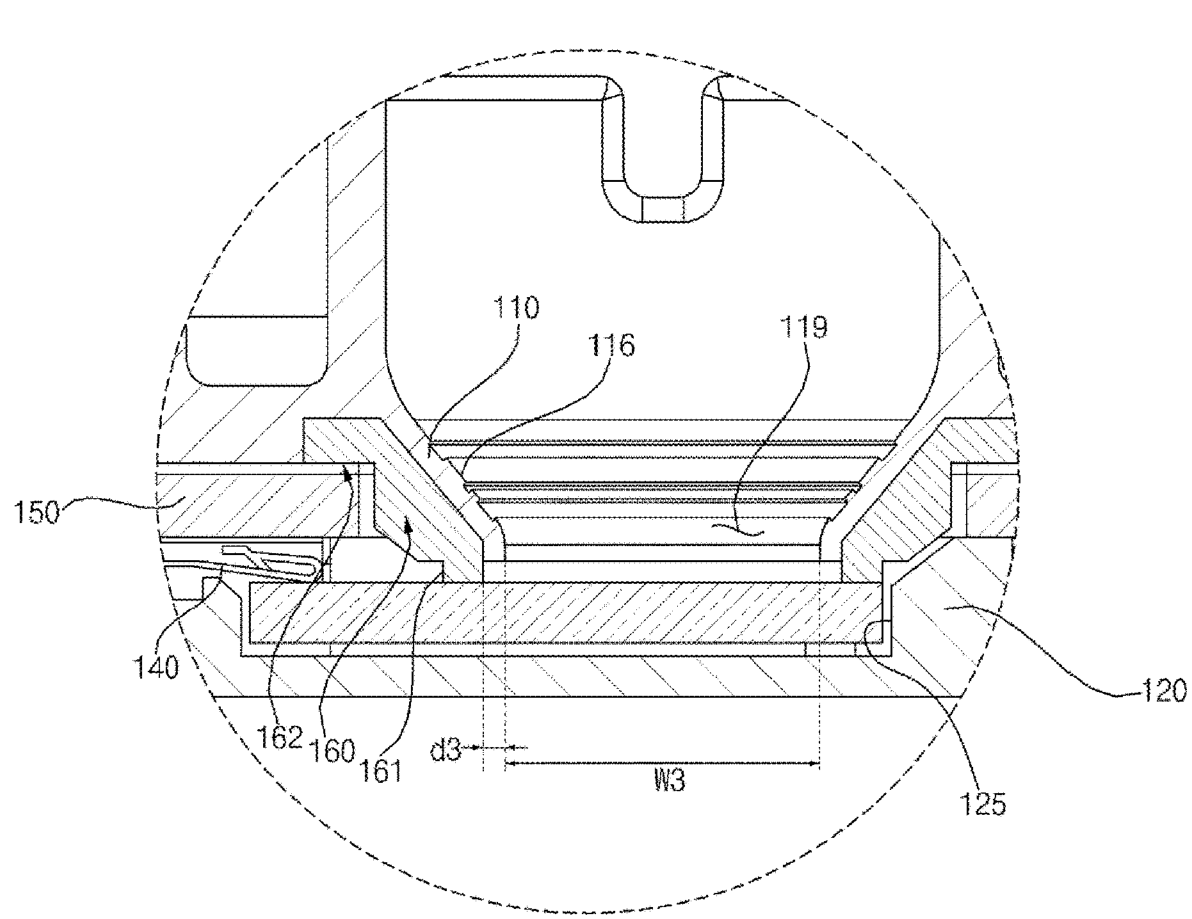

The biosensor cartridge 100 of the biosensor system 10 can be deformed into the shape shown in FIGS. 21A to 21B.

In what follows, a biosensor cartridge according to another embodiment of the present disclosure will be described with reference to FIGS. 21A and 21B.

FIG. 21A shows a rear view of the upper case of another example of the biosensor cartridge 100 of FIG. 1, and FIG. 21B shows a cross-sectional view of FIG. 7 to which the upper case of FIG. 21A is applied.

The configuration of the lower housing 120, the biosensor chip 500, and the circuit board 150 of the biosensor cartridge 100 of FIGS. 21A and 21B is the same as that of the biosensor cartridge 100 of FIGS. 6 and 7; also, since the attachment configuration of the upper housing 110 and the lower housing 120 is the same as that of FIG. 10, a description thereof will be omitted.

Referring to FIGS. 21A and 21B, the biosensor cartridge 100 according to the present embodiment accommodates the biosensor chip 500 that generates an electrical detection signal according to a target material and has a structure that includes a connection terminal 153 capable of transmitting the detection signal to an external diagnostic device 200.

At this time, on the rear surface of the upper housing 110 of the biosensor cartridge 100, a molding portion 160 for bonding with and sealing the circuit board 150 and the biosensor chip 500 is formed together.

The upper housing 110 faces the lower housing 120 and is coupled to the lower housing 120 and serves as an upper case capable of accommodating the circuit board 150 and the biosensor chip 500 therein. In addition, an accommodating portion 119 exposing the sensor area 530 of the biosensor chip 500 is formed in the upper housing 110 to accommodate a test target specimen.

The upper housing 110 is formed to have rigidity that can firmly support the connecting member 140 by pressing the connecting member 140 with a predetermined force.

When the upper housing 110 and the lower housing 120 are combined, an opening protruding the connection terminal 153 of the circuit board 150 is formed in the cross-section, and the connection terminal 153 is exposed to be inserted into the insertion hole 2914 of the external diagnostic device 200 as the connection terminal 153 of the cartridge. Due to the strong coupling between the upper housing 110 and the lower housing 120, the sample provided to the biosensor chip 500 through the accommodating portion 119 can be prevented from leaking into the housings 110 and 120.

The accommodating portion 119 for exposing the sensor area 530 of the biosensor chip 500 and accommodating a specimen is formed on the upper surface 111 of the upper housing 110. The accommodating portion 119 is a space for inducing a reaction with the exposed sensor area 530 by accommodating a test target specimen in a fluid state, e.g., in a liquid state, and the accommodating portion 119 forms a conical channel whose diameter becomes narrower as it approaches the sensor area 530 from the upper surface 111.

Therefore, the accommodating portion 119 is formed to have an inclined surface 116 such that the diameter W1 of the opening of the upper surface is larger than the diameter W2 of the opening at the end of the accommodating portion 119.

At this time, an inclination angle θ1 of the inclined surface 116—the angle of the inclined surface 116 with respect to the horizontal direction (x-axis) in which the biosensor chip 500 is placed, when viewed from the cross-section in FIG. 7—can be uniform but can have an inflection point.

That is, the inclination angle increases as it approaches the sensor area 530, and it forms a verticality in the outermost area closest to the sensor area 530 so that it can be changed to a cylindrical passageway.

As described above, since the accommodating portion 119 has the inclined surface 116, a concave groove having a depth equal to the height from the upper surface of the upper housing 110 to the sensor area 530 is formed; a specimen is collected in the groove to induce a reaction with the probe material in the sensor area 530.

The rear surface of the upper housing 110 can include an inclined portion to form the inclined surface 116 of the accommodating portion 119, as shown in FIG. 21B.

At this time, the rear surface of the upper housing 110 of FIGS. 21A and 21B further includes a molding portion 160 formed along the inclined portion.

The molding portion 160 replaces the sealing part 130 of FIG. 7.

That is, the biosensor cartridge 100 of FIGS. 21A and 21B forms the molding portion 160 sealing between the sensor region 530 of the biosensor chip 500 and the upper housing 110 in the rear surface of the upper housing 110.

The molding portion 160 is not formed as a separate element but is integrated with the rear surface of the upper housing 110 through secondary injection during molding of the upper housing 110 and is formed and simultaneously hardened.

The upper housing 110 and the lower housing 120 can be made of at least one of polymethyl methacrylate, polycarbonate, cyclic olefine copolymer, polyethylene sulfone, and polystyrene or a material obtained by a combination of at least two or more of the above. However, the material for the housing 110, 120 is not necessarily limited to the specific example above and can be made of a polydimethylsiloxane material, which is a silicone-based organic polymer.

For example, during the first injection of the upper housing 110, polycarbonate or a polymer containing a predetermined amount of a glass fillet in the polycarbonate is injected into the mold. At this time, at a second stage, liquid silicone is injected to be formed along the rear surface of the upper housing 110, specifically along the inclined portion, and to protrude by being extended below the lower opening of the inclined surface 116 to protrude.

As described above, by sequentially injecting different materials into the mold, it is possible to manufacture the upper housing 110 and the molding portion 160 in an integrated manner.

In this situation, since the liquid silicone has predetermined elasticity with a hardness of 40, material and process costs can be reduced compared to implementing a separate sealing member.

On the other hand, the molding portion 160 formed by the hardening of the liquid silicone is aligned with the lower opening of the inclined surface 116 as shown in FIGS. 21A and 21B and includes a molding opening exposing the sensor area 530 to the lower opening.

That is, the molding portion 160 can have a molding opening 165 having a diameter W3 larger than the diameter W2 of the rear opening of the accommodating portion 119, and the rear opening and the sealing opening 131 can be arranged to have concentric circles. Accordingly, as shown in FIG. 21B, the molding portion 160 is disposed outside the lower opening of the accommodating portion 119 to form a concave groove at the end 161 in contact with the sensor area 530.

The structure above is intended to provide a tolerance when the molding unit 160 is compressed and thus avoid the risk of covering the sensor area 530 in contact with a specimen when the molding unit 160 having elasticity is pushed into the sensor area 530 due to compression of the molding portion 160.

As described above, it is possible to ensure the sealing of the specimen while securing the area of the sensor area 530 by adjusting the size of the molding opening 165 of the molding portion 160 and the opening size of the accommodating portion 119.

In addition, when being fitted so that the opening 115 of the circuit board 150 surrounds the rear surface of the inclined surface 116 of the accommodating portion 119, the molding portion 160 is formed to have a step 162 vertically in the area where the molding portion 160 meets the opening 115 of the circuit board 150.

That is, the molding portion 160 located on the rear surface of the inclined surface 116 of the accommodating portion 119 can form a step 162 corresponding to the cross-section of the opening 155 of the circuit board 150 for being fitted and coupled with the opening 155 of the circuit board 150 at the portion to which the opening 155 of the circuit board 150 is coupled.

The step 162 can have a separation distance from the side surface of the opening 155 of the circuit board 150, but is not limited thereto, and can be fitted and coupled.

It is easy to fix the circuit board 150 when being fitted and coupled without a separation distance, but a separation distance can be formed for tolerance. At this time, it is required that the width of the separation distance range from 0.05 mm to 0.2 mm.

In addition, when the rear surface of the circuit board 150 is placed in the lower housing 120, a separation distance for tolerance can be ensured from the rear surface of the upper housing 120.

As described above, since the front surface of the circuit board 150 and the molding portion 160 formed in the rear surface of the upper housing 110 are coupled with a predetermined tolerance distance, it is possible to prevent a distortion of the circuit board 150 and compensate for a process error, thereby reducing the defect rate.

As described above, since the molding portion 160 is coupled to the circuit board through the step 162 and is injected together with the upper housing 110 to contact the sensor area 530, alignment is made simple when the cartridge 100 is assembled, and the manufacturing process is simplified.

A biosensor diagnostic device 200 according to one embodiment of the present disclosure comprises an interface 205 receiving an electrical signal from a biosensor cartridge 100 in response to a connection to a connection terminal 153 of the biosensor cartridge 100, an image reader 270 capturing a code image attached to the biosensor cartridge 100, a signal processor 295 processing a signal received from the interface 205, and a wireless transceiver 260 transmitting diagnostic result information Infc output from the signal processor 295 and information Infa corresponding to the captured code image to a server 400 or an external terminal 300. Accordingly, a diagnosis result can be provided promptly and accurately.

The operation of the biosensor diagnostic device 200 will be described in more detail with reference to FIG. 22.

Figure 22:
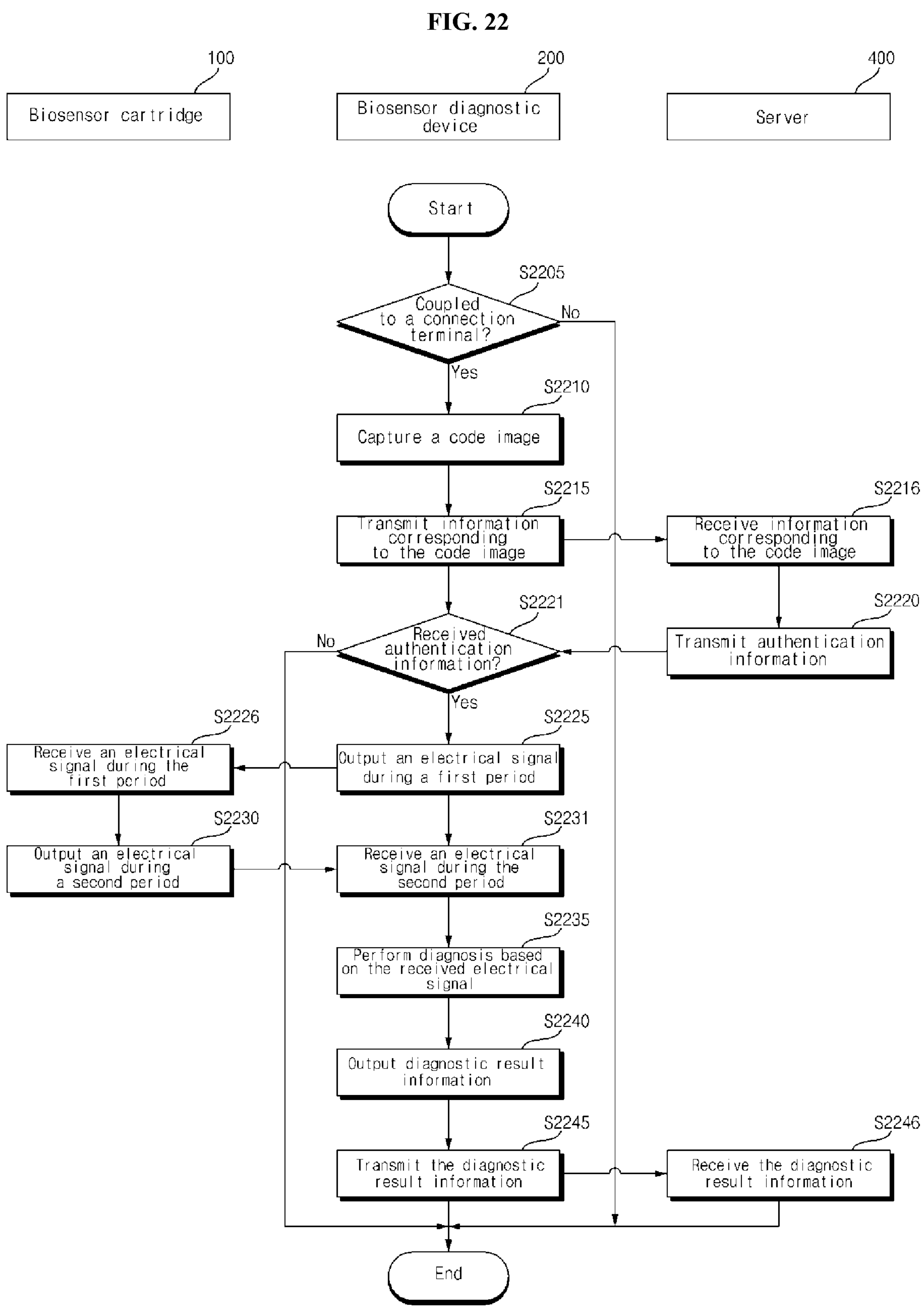
FIG. 22 is a flowchart illustrating a method for operating a biosensor system according to one embodiment of the present disclosure.

FIG. 22 is a flowchart illustrating a method for operating a biosensor system according to one embodiment of the present disclosure, and FIGS. 23A to 24B are diagrams referenced to describe the operation method of FIG. 22.

Referring to the figure, the signal processor 295 within the biosensor diagnostic device 200 of the biosensor system 10 according to one embodiment of the present disclosure determines whether the connection terminal 153 of the biosensor cartridge 100 is coupled to the interface 205 S2205.

For example, when current flows to the outside through the interface 205, the signal processor 295 within the biosensor diagnostic device 200 can determine that the connection terminal 153 of the biosensor cartridge 100 is coupled to the interface 205.

When the connection terminal 153 of the biosensor cartridge 100 is coupled to the interface 205, the image reader 270 within the biosensor diagnostic device 200 captures a code image attached to the biosensor cartridge 100 S2210 (e.g., the QR code on the back of the biosensor cartridge 100).

The captured code image can be transmitted to the signal processor 295 in the biosensor diagnostic device 200.

The signal processor 295 in the biosensor diagnostic device 200 can transmit the captured code image or information Infa corresponding to the captured code image, through the wireless transceiver 260, to the external server 400 or an external terminal 300 S2215.

For example, the signal processor 295 in the biosensor diagnostic device 200 can extract information Infa corresponding to the code image from the code image captured by the image reader 270 and transmit the information Infa corresponding to the code image to the server 400.

Figure 23A:
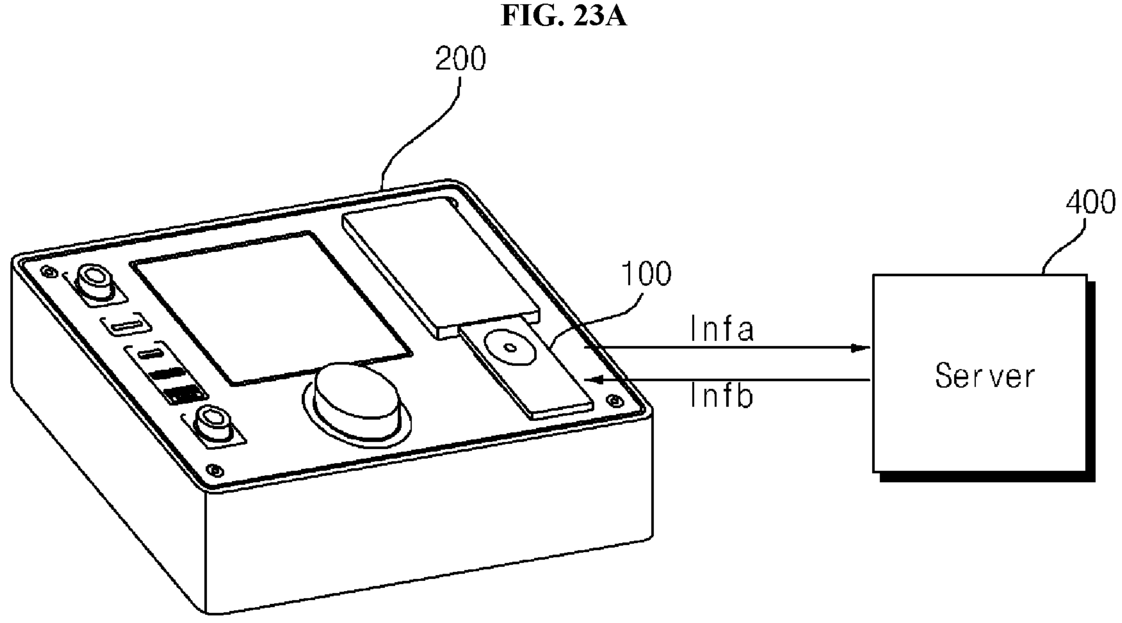
FIGS. 23A to 24B are diagrams referenced to describe the operation method of FIG. 22 according to embodiments of the present disclosure.

FIG. 23A shows a situation in which the connection terminal 153 of the biosensor cartridge 100 is coupled to the interface 205 of the biosensor diagnostic device 200, and a captured code image or information Infa corresponding to the captured code image (e.g., QR code) is transmitted to an external server 400.

The external server 400 receives the captured code image or the information Infa corresponding to the captured code image S2216 and performs authentication through comparison with internal data.

When authentication is completed, the external server 400 transmits authentication information Infb S2220. Correspondingly, the wireless transceiver 260 of the biosensor diagnostic device 200 receives the authentication information Infb, as shown in FIG. 23A S2221.

Meanwhile, when the biosensor diagnostic device 200 receives the authentication information Infb from the server 400, the signal processor 295 in the biosensor diagnostic device 200 performs a diagnosis procedure.

Figure 23B:
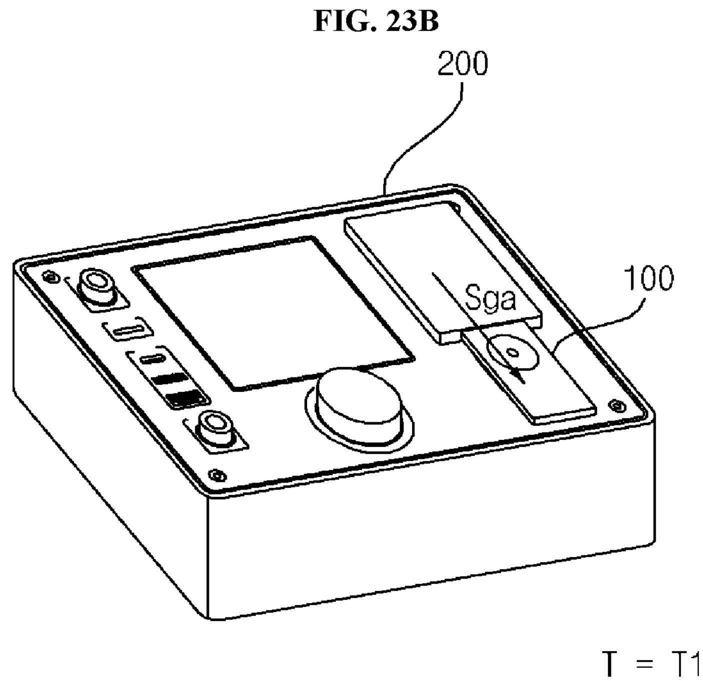
Figure 23C:
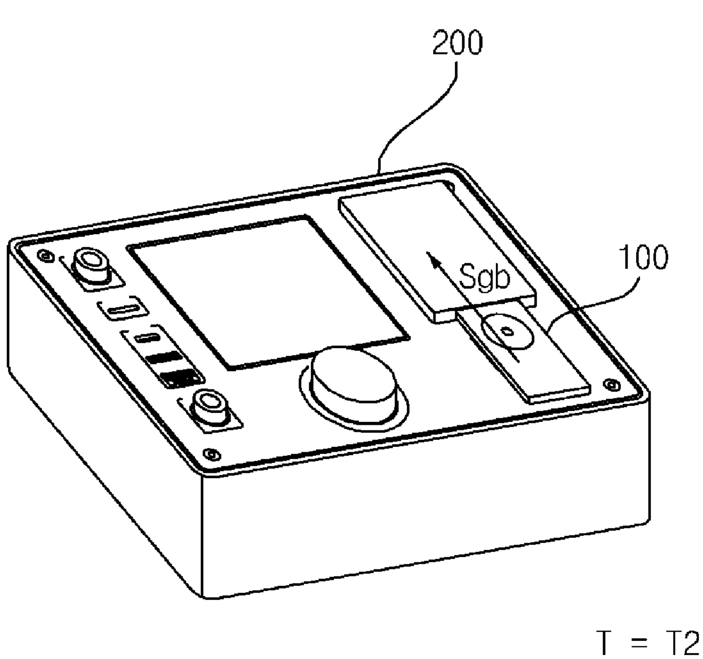
Figure 23D:
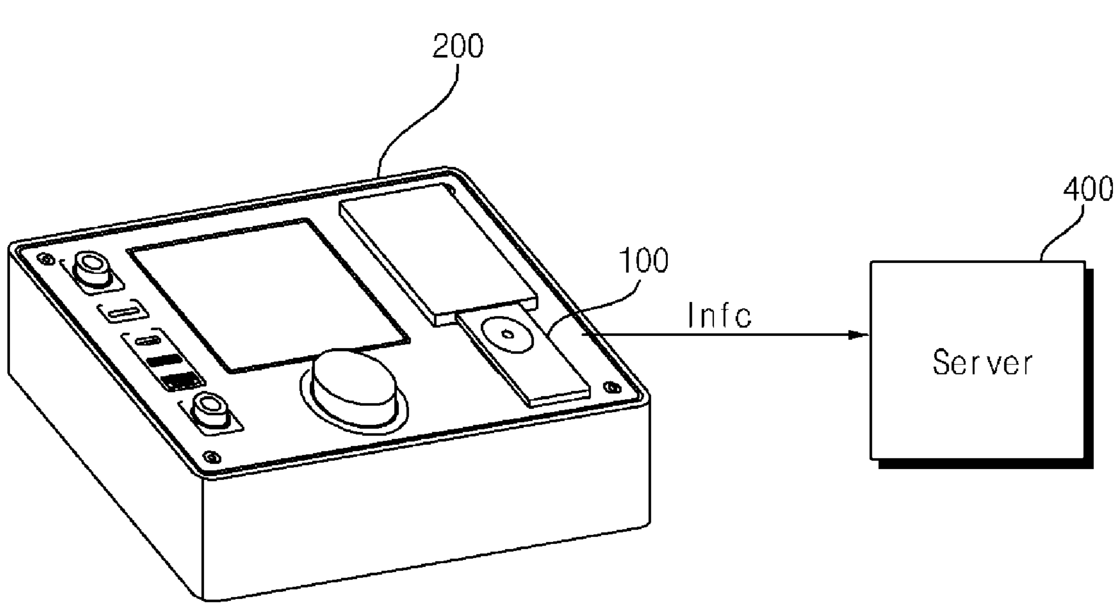
Figure 23E:
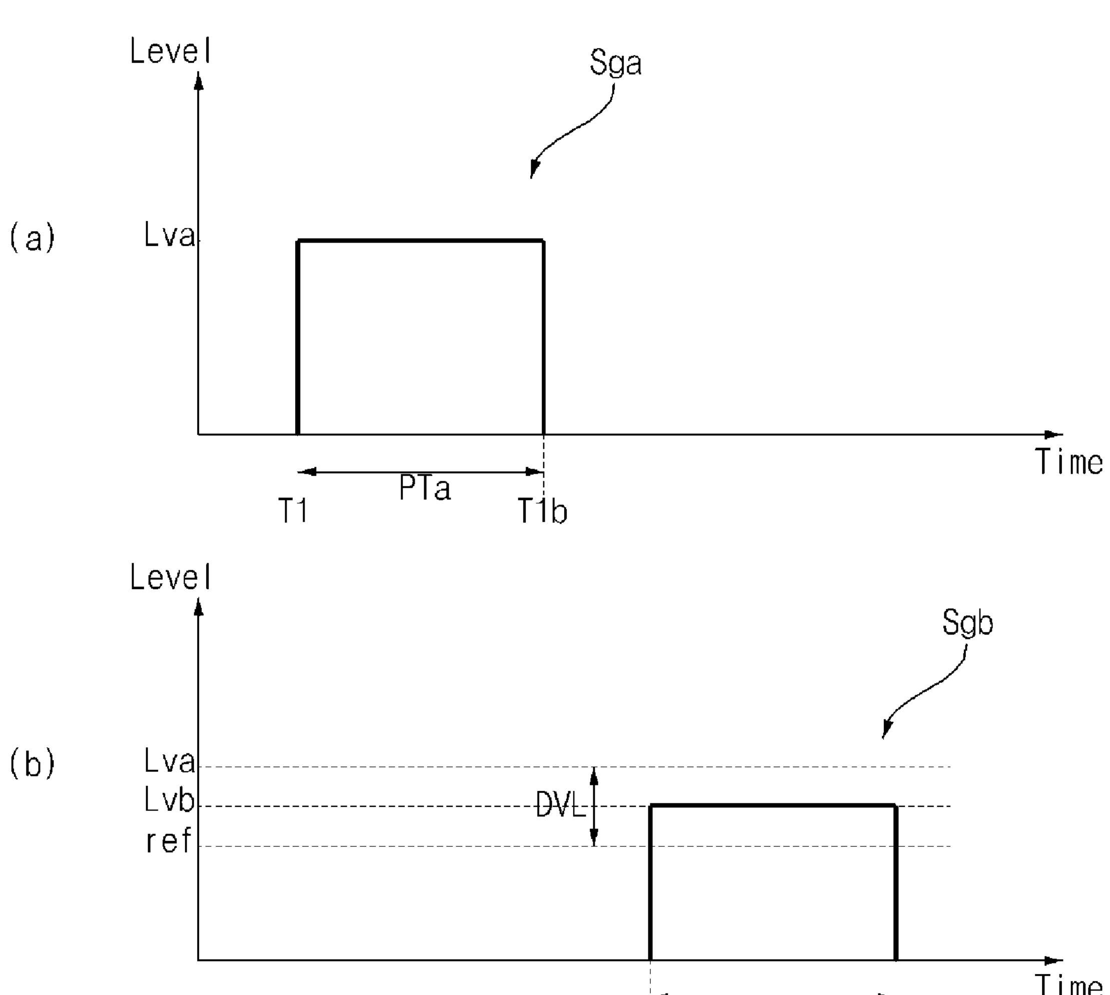

For example, when the authentication information Infb is received from the server 400, the interface 205, as shown in FIG. 23B, during the first period PTa, through the interface 205, outputs an electrical signal Sga of the first level Lva to the biosensor cartridge 100 S2225 (e.g., see part (a) of FIG. 23E).

Correspondingly, the biosensor cartridge 100 receives the electrical signal Sga of the first level Lva S2226.

FIG. 23B shows an example in which, at a first time point T1 which is the start time of the first period PTa, an electrical signal Sga of the first level Lva is transmitted from the biosensor diagnostic device 200 to the biosensor cartridge 100.

Meanwhile, the biosensor cartridge 100 can apply the electrical signal Sga of the first level Lva to at least one of the electrodes 535S, 535D, 535G of the sensor area 530.

And the biosensor cartridge 100 can output the electrical signal Sgb of the second level Lvb flowing through at least one of the electrodes 535S, 535D, 535G of the sensor area 530 during the second period PTb after the first period PTa S2230 (e.g., see part (b) of FIG. 23E).

In response to the above operation, the biosensor diagnostic device 200 can receive the electrical signal Sgb of the second level Lvb, as shown in FIG. 23C S2231.

FIG. 23C illustrates an example in which the electrical signal Sgb of the second level Lvb is output to the biosensor diagnostic device 200 from the biosensor cartridge 100 at the second time point T2 which is the start time point of the second period PTb.

Meanwhile, the signal processor 295 in the biosensor diagnostic device 200 can diagnose the existence of a target material based on a level difference DVL between the electrical signal Sga of the first level Lva and the electrical signal Sgb of the second level Lvb or the electrical signal Sgb of the second level Lvb and output diagnostic result information Infc S2240.

And the signal processor 295 in the biosensor diagnostic device 200 can transmit the diagnostic result information Infc to the server 400 or the external terminal 300, as shown in FIG. 23D. In response to the transmission, the server 400 or the external terminal 300 can receive the diagnostic result information Infc S2246.

FIG. 23D illustrates a situation in which the diagnostic result information Infc is transmitted from the biosensor diagnostic device 200 to the server 400. Accordingly, a diagnosis result can be provided promptly and accurately.

FIG. 23E illustrates one example of the electrical signal Sga of the first level Lva during a first period PTa and one example of the electrical signal Sgb of the second level Lvb of a second period PTb.

Referring to the figure, the interface 205 of the biosensor diagnostic device 200 can output the electrical signal Sga of the first level Lva during the first period PTa from T1 to T1*b*.

Meanwhile, the interface 205 of the biosensor diagnostic device 200 can receive the electrical signal Sgb of the second level Lvb during the second period PTb from T2 to T2*b*.

Meanwhile, when the level of the electrical signal received from the biosensor cartridge 100 exceeds a reference level ref, as shown in FIG. 23E, part (b), the signal processor 295 can diagnose the existence of a target material based on the level difference DVL between the electrical signal Sga of the first level Lva and the electrical signal Sgb of the second level Lvb or the electrical signal Sgb of the second level Lvb and output the diagnostic result information Infc.

Meanwhile, when the level of the electrical signal received from the biosensor cartridge 100 is less than the reference level ref during the second period PTb, accurate diagnosis may not be achieved; therefore, the signal processor 295 can supply the electrical signal Sga of the first level Lva to the biosensor cartridge 100 through the interface 205 during a third period after the second period (PTb) and receive an electrical signal from the biosensor cartridge 100 during a fourth period after the third period.

And when the level of the electrical signal received from the biosensor cartridge 100 exceeds the reference level ref during the fourth period, the signal processor 295 can diagnose the existence of a target material based on the level difference DVL between the electrical signal Sga of the first level Lva during the third period and the electrical signal Sgb of the second level Lvb during the fourth period or the electrical signal Sgb of the second level Lvb during the fourth period and output diagnostic result information Infc. Accordingly, even though an electrical signal less than the reference level during the second period is received, a diagnosis result can be provided promptly and accurately.

Or, when the level of the electrical signal received from the biosensor cartridge 100 is less than the reference level ref during the second period PTb, the signal processor 295 can supply the electrical signal of the third level larger than the first level Lva to the biosensor cartridge 100 through the interface 205 during the third period after the second period (PTb), receive an electrical signal from the biosensor cartridge 100 during the fourth period after the third period, diagnose the existence of a target material based on the electrical signal received during the fourth period, and output the diagnostic result information Infc. Accordingly, even though an electrical signal less than the reference level during the second period is received, a diagnosis result can be provided promptly and accurately.

Meanwhile, the signal processor 295 can receive update data for the diagnosis result from the server 400.

As shown in FIG. 23E, the signal processor 295 can supply the electrical signal Sga of the first level Lva to the biosensor cartridge 100 through the interface 205 during the first period PTa and receive update data for a diagnosis result from the server 400 after receiving the electrical signal Sgb of the second level Lvb from the biosensor cartridge 100 during the second period PTb after the first period PTa.

Accordingly, through the interface 205, during the third period after receiving the update data from the server 400, the signal processor 295 can supply the electrical signal of the third level larger than the first level to the biosensor cartridge 100, receive an electrical signal from the biosensor cartridge 100 for the fourth period after the third period, diagnose the existence of a target material based on the electrical signal received during the fourth period, and output diagnostic result information Infc. Accordingly, a diagnosis result can be provided more promptly and more accurately based on the update.

Meanwhile, the signal processing device 295 can sequentially supply electrical signals of a plurality of levels to the biosensor cartridge 100 through the interface 205 during the first period PT1 and sequentially receive the electrical signal of a plurality of levels from the biosensor cartridge 100 during the second period PT2 after the first period PT1. Accordingly, a diagnosis result can be provided promptly and accurately based on electrical signals of a plurality of levels.

Figure 23F:
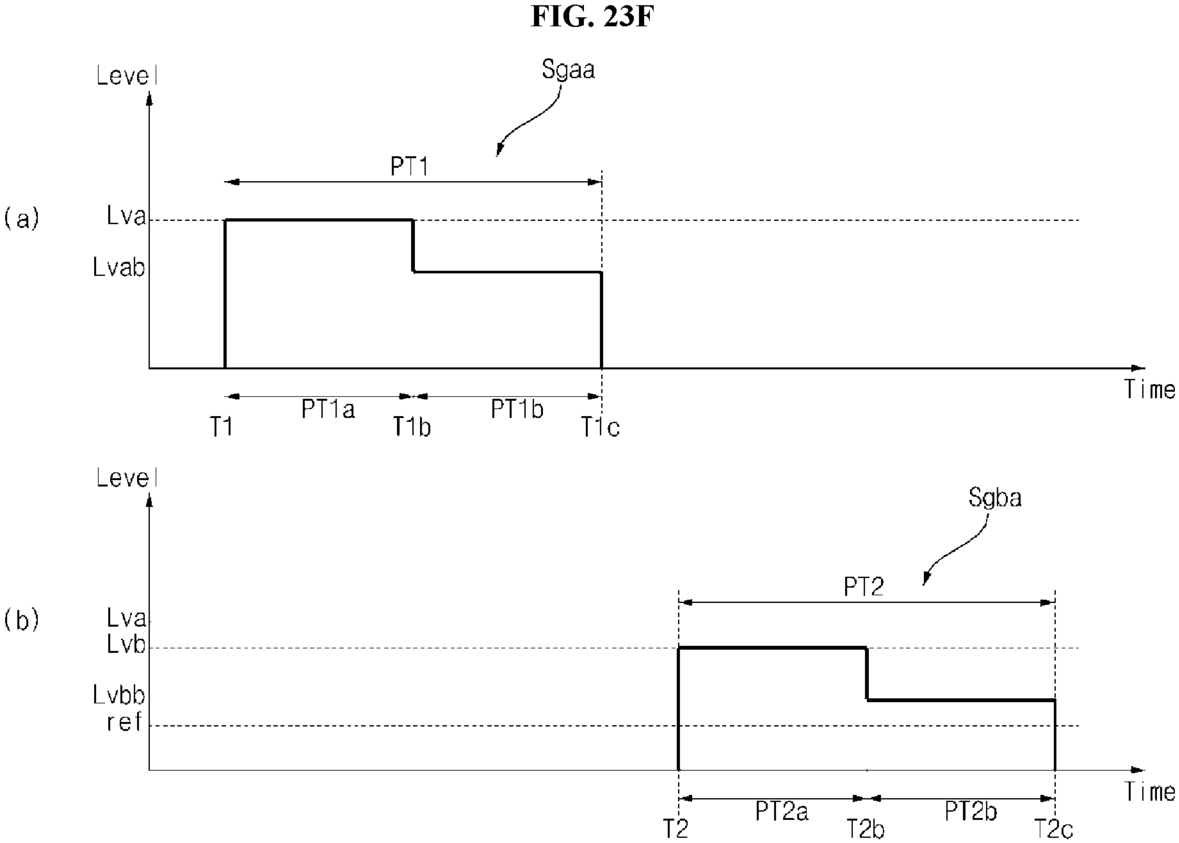

FIG. 23F illustrates an example of an electrical signal Sgaa having a plurality of levels Lva, Lvab sequentially during the first period PT1 and an example of an electrical signal Sgba of a plurality of levels Lvb, Lvbb during the second period PT2.

Referring to the figure, the interface 205 of the biosensor diagnostic device 200 can output the electrical signal Sgaa of the Lva level between T1 and T1*b*, which is a part of the first period PT1 and output the electrical signal Sgaa of the Lvab level lower than the Lva level between T1*b* and T1*c*, which forms another part of PT1.

Meanwhile, the interface 205 of the biosensor diagnostic device 200 can receive the electrical signal Sgba of the Lvb level between T2 and T2*b*, which is a part of the second period PT2 and receive the electrical signal Sgba of the Lvbb level lower than the Lvb level between T2*b* and T2*c*, which form another part of the second period PT2.

Meanwhile, the signal processor 295 can diagnose the existence of a target material based on the level difference between the electrical signal of a plurality of levels Lva, Lvab during the first period PT1 and the electrical signal of a plurality of levels during the second period PT2 or the electrical signal of a plurality of levels Lvb, Lvbb during the second period PT2 and output diagnostic result information.

Specifically, when a first biosensor cartridge 100 is equipped with the graphene-based multi-channel sensor chip 500, the signal processor 295 can diagnose the existence of a first target material based on the electrical signal Sgaa of Lva level and the electrical signal Sgba of Lvb level; and diagnose the existence of a second target material based on the electrical signal Sgaa of Lvab level and the electrical signal Sgba of Lvbb level. In other words, a diagnosis result on the existence of a plurality of target materials can be provided promptly and accurately.

Meanwhile, when different biosensor cartridges are coupled to the biosensor diagnostic device 200, it is possible to diagnose the existence of the same target material.

Figure 24A:
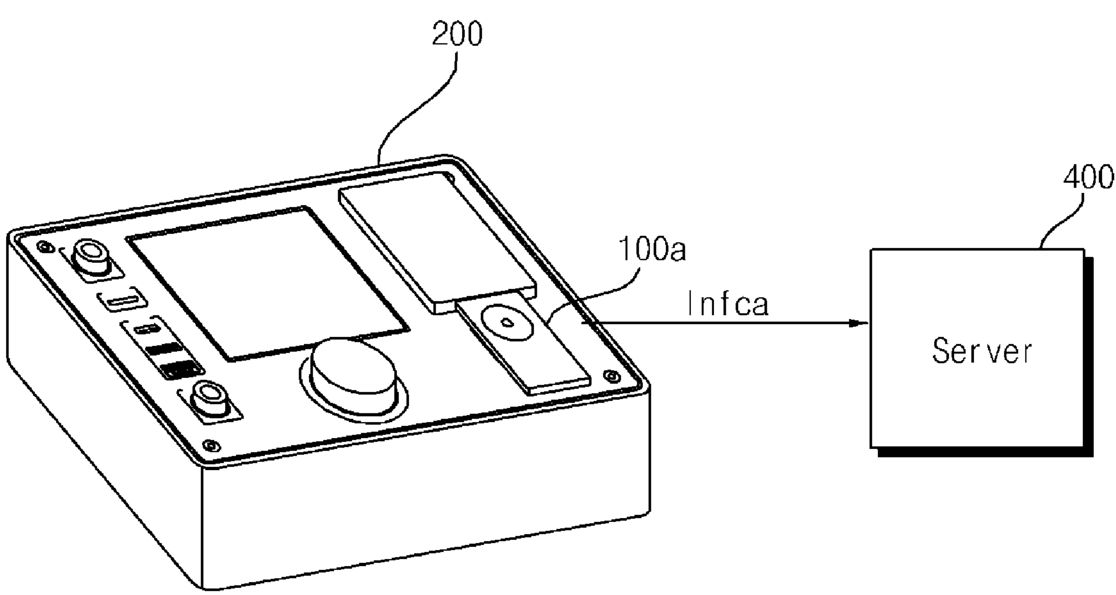

FIG. 24A illustrates an example in which the first biosensor cartridge 100*a* is coupled to the biosensor diagnostic device 200, and the first diagnostic result information Infca is transmitted to the server 400.

Figure 24B:
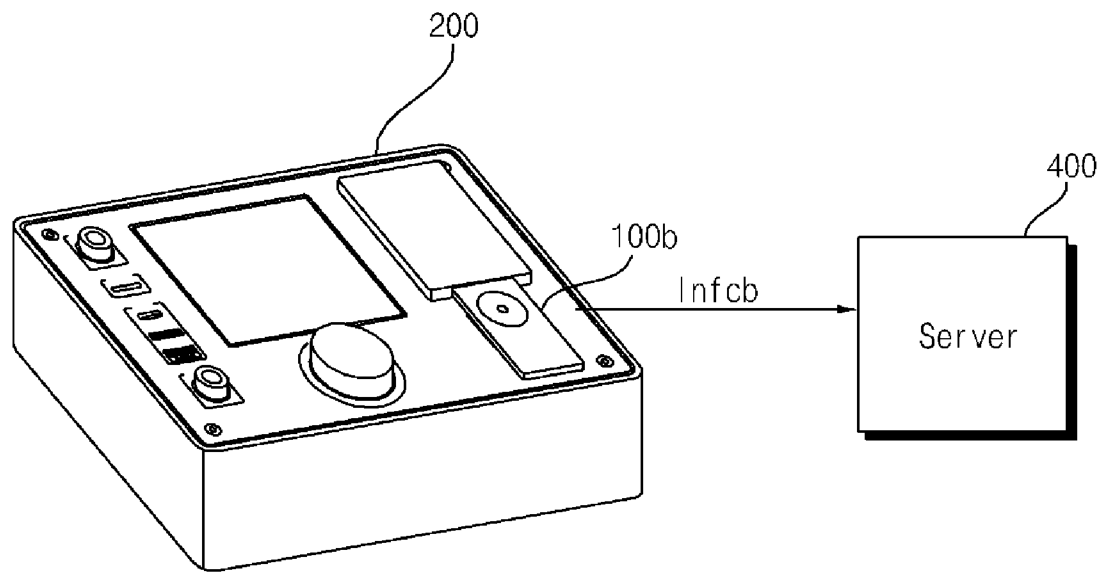

FIG. 24B illustrates an example in which the second biosensor cartridge 100*a* is coupled to the biosensor diagnostic device 200, and the second diagnostic result information Infcb is transmitted to the server 400.

Meanwhile, the signal processor 295 can extract target material type information from the image captured by the image reader 270.

When the target material types of the first biosensor cartridge 100*a* and the second biosensor cartridge 100*b* are the same, the signal processor 295 can output an electrical signal of the same level to the first biosensor cartridge 100*a* and the second biosensor cartridge 100*b*.

For example, as shown in FIG. 24A, when the interface 205 is coupled to the connection terminal 153 of the first biosensor cartridge 100*a*, the signal processor 295 can supply the electrical signal Sga of the first level Lva to the first biosensor cartridge 100*a*; as shown in FIG. 24B, when the interface 205 is coupled to the connection terminal 153 of the second biosensor cartridge 100*b*, the signal processor 295 can supply the electrical signal Sga of the same first level Lva to the second biosensor cartridge 100*b*.

As shown in FIG. 24A, when the interface 205 is coupled to the connection terminal 153 of the first biosensor cartridge 100*a*, the signal processor 295 can receive an electrical signal from the first biosensor cartridge 100*a*, diagnose the existence of a first target material, and output the first diagnostic information Infca.

Meanwhile, as shown in FIG. 24B, when the interface 205 is coupled to the connection terminal 153 of the second biosensor cartridge 100*b*, the signal processor 295 can receive an electrical signal from the second biosensor cartridge 100*b*, diagnose the existence of the same first target material, and output the second diagnostic information Infcb.

Meanwhile, when different biosensor cartridges can be coupled to the biosensor diagnostic device 200, it is possible to diagnose the existence of different target materials.

When it is determined based on the image captured by the image reader 270 that the target material types of the first biosensor cartridge 100*a* and the second biosensor cartridge 100*b* are different, the signal processor 295 can output electrical signals at different levels to the first biosensor cartridge 100*a* and the second biosensor cartridge 100*b*, respectively.

For example, as shown in FIG. 24A, when the interface 205 is coupled to the connection terminal 153 of the first biosensor cartridge 100*a*, the signal processor 295 can supply the electrical signal Sga of the first level Lva to the first biosensor cartridge 100*a*; as shown in FIG. 24B, when the interface 205 is coupled to the connection terminal 153 of the second biosensor cartridge 100*b*, the signal processor 295 can supply the electrical signal Sgb of the second level Lvb different from the first level Lva to the second biosensor cartridge 100*b*.

As shown in FIG. 24A, when the interface 205 is coupled to the connection terminal 153 of the first biosensor cartridge 100*a*, the signal processor 295 receives an electrical signal from the first biosensor cartridge 100*a*, diagnoses the existence of a first target material, and outputs the first diagnostic result information Infca.

Meanwhile, as shown in FIG. 24B, when the interface 205 is coupled to the connection terminal 153 of the second biosensor cartridge 100*b*, the signal processor 295 receives an electrical signal from the second biosensor cartridge 100*b*, diagnoses the existence of a second target material, and outputs the second diagnostic result information Infcb. Accordingly, using a plurality of biosensor cartridges 100, a diagnosis result on the existence of a plurality of target materials can be provided promptly and accurately.

Meanwhile, the signal processor 295 can extract information on the type of target material from the code image attached to the biosensor cartridge 100 and to output an electrical signal with a variable level through the interface 205 depending on the type of the target material. Accordingly, using a plurality of biosensor cartridges 100, a diagnosis result on the existence of a plurality of target materials can be provided promptly and accurately.

Meanwhile, the signal processor 295 can receive update data from the server 400, change the level of an electrical signal supplied to the biosensor cartridge 100 through the interface 205 based on the received update data, or change the number of levels of a plurality of electrical signals supplied to the biosensor cartridge 100. Accordingly, a diagnosis result can be provided promptly and accurately based on the update.

Throughout the document, preferred embodiments of the present disclosure have been described with reference to appended drawings; however, the present disclosure is not limited to the embodiments above. Rather, it should be noted that various modifications of the present disclosure can be made by those skilled in the art to which the present disclosure belongs without leaving the technical scope of the present disclosure defined by the appended claims, and these modifications should not be understood individually from the technical principles or perspectives of the present disclosure.

What is claimed is:

1. A biosensor diagnostic device comprising:

an interface configured to receive an electrical signal from a biosensor cartridge in response to being connected to a connection terminal of the biosensor cartridge;

an image reader configured to capture a code image on the biosensor cartridge;

a signal processor configured to process a signal received from the interface for generating diagnostic result information; and a wireless transceiver configured to transmit information corresponding to the code image and the diagnostic result information to a server or an external terminal, wherein the signal processor is configured to:

extract code information based on the code image captured by the image reader, transmit the code information to the server for authentication, and in response to receiving authentication information from the server, supply a first electrical signal of a first level to the biosensor cartridge through the interface during a first period and receive a second electrical signal of a second level from the biosensor cartridge during a second period after the first period.

2. The biosensor diagnostic device of claim 1, wherein the signal processor is configured to:

in response to receiving the authentication information from the server, transmit the diagnostic result information to the server or the external terminal.

3. The biosensor diagnostic device of claim 1, wherein the signal processor is configured to:

diagnose an existence of a target material being present in the biosensor cartridge based on a level difference between the first electrical signal of the first level and the second electrical signal of the second level, and output the diagnostic result information based on the level difference.

4. The biosensor diagnostic device of claim 1, wherein the signal processor is configured to:

in response to the second level of the second electrical signal received from the biosensor cartridge being less than or equal to a reference level during the second period, supply a third electrical signal of the first level to the biosensor cartridge through the interface during a third period and receive a fourth electrical signal from the biosensor cartridge during a fourth period after the third period.

5. The biosensor diagnostic device of claim 1, wherein the signal processor is configured to:

in response to the second level of the second electrical signal received from the biosensor cartridge being less than or equal to a reference level during the second period, supply a third electrical signal of a third level larger than the first level to the biosensor cartridge through the interface during a third period, receive a fourth electrical signal from the biosensor cartridge during a fourth period after the third period, diagnose an existence of a target material being present in the biosensor cartridge based on the fourth electrical signal received during the fourth period, and output the diagnostic result information based on the fourth electrical signal.

6. The biosensor diagnostic device of claim 1, wherein the signal processor is configured to:

receive update data from the server, supply a third electrical signal having a third level larger than the first level through the interface during a third period after receiving the update data from the server, receive a fourth electrical signal from the biosensor cartridge during a fourth period after the third period, diagnose an existence of a target material being present in the biosensor cartridge based on the fourth electrical signal received during the fourth period, and output the diagnostic result information based on the fourth electrical signal.

7. The biosensor diagnostic device of claim 1, wherein the signal processor is configured to:

extract target material type information on a type of target material to be diagnosed from the code image on the biosensor cartridge, and output an electrical signal of an updated level through the interface, the updated level being based on the target material type information.

8. The biosensor diagnostic device of claim 1, wherein the signal processor is configured to:

receive update data from the server, and change a level of an electrical signal supplied to the biosensor cartridge based on the update data or change a number of levels of a plurality of electrical signals supplied to the biosensor cartridge through the interface.

9. The biosensor diagnostic device of claim 1, wherein the signal processor is configured to:

in response to the interface being coupled to a connection terminal of a first biosensor cartridge, receive a first electrical signal from the first biosensor cartridge, diagnose an existence of a first target material being present in the first biosensor cartridge based on the first electrical signal and output first diagnostic result information based on the first electrical signal, in response to the interface being coupled to a connection terminal of a second biosensor cartridge, receive a second electrical signal from the second biosensor cartridge, and diagnose an existence of a second target material being present in the second biosensor cartridge based on the second electrical signal and output second diagnostic result information based on the second electrical signal.

10. The biosensor diagnostic device of claim 9, wherein, in response to the interface being coupled to the connection terminal of the first biosensor cartridge, the signal processor is configured to supply an electrical signal of a first level to the first biosensor cartridge, and wherein, in response to the interface being coupled to the connection terminal of the second biosensor cartridge, the signal processor is configured to supply another electrical signal of the first level to the second biosensor cartridge.

11. The biosensor diagnostic device of claim 1, wherein, the signal processor is configured to:

in response to the interface being coupled to a connection terminal of a first biosensor cartridge, receive a first electrical signal from the first biosensor cartridge, diagnose an existence of a first target material being present in the first biosensor cartridge and output first diagnostic result information based on the first electrical signal; and in response to the interface being coupled to a connection terminal of a second biosensor cartridge, receive a second electrical signal from the second biosensor cartridge, diagnose an existence of a second target material being present in the second biosensor cartridge and output second diagnostic result information based on the second electrical signal.

12. The biosensor diagnostic device of claim 11, wherein, in response to the interface being coupled to the connection terminal of the first biosensor cartridge, the signal processor is configured to supply an electrical signal of a first level to the first biosensor cartridge, and wherein, in response to the interface being coupled to the connection terminal of the second biosensor cartridge, the signal processor is configured to supply an electrical signal of a level different than the first level to the second biosensor cartridge.

13. A biosensor diagnostic device comprising:

an interface configured to receive an electrical signal from a biosensor cartridge in response to being connected to a connection terminal of the biosensor cartridge;

an image reader configured to capture a code image on the biosensor cartridge;

a signal processor configured to process a signal received from the interface for generating diagnostic result information; and a wireless transceiver configured to transmit information corresponding to the code image and the diagnostic result information to a server or an external terminal, wherein the signal processor is configured to:

extract code information based on the code image captured by the image reader, and transmit the code information to the server, wherein the interface supplies electrical signals of multiple levels sequentially to the biosensor cartridge through the interface during a first period in response to authentication information being received from the server and sequentially receives the electrical signals of multiple levels from the biosensor cartridge during a second period after the first period.

14. The biosensor diagnostic device of claim 13, wherein the signal processor is configured to:

diagnose a presence of one or more of a plurality of target materials based on at least one level difference between the electrical signals of the multiple levels supplied by the interface during the first period and the electrical signals of the multiple levels received by the interface during the second period and output the diagnostic result information based on the at least one level difference.

15. A biosensor system comprising:

a biosensor cartridge configured to receive an analysis specimen; and a biosensor diagnostic device, wherein the biosensor diagnostic device comprises:

an interface configured to receive an electrical signal from the biosensor cartridge in response to the biosensor diagnostic device being connected to a connection terminal of the biosensor cartridge;

an image reader configured to capture a code image on the biosensor cartridge;

a signal processor configured to process a signal received from the interface for generating diagnostic result information; and a wireless transceiver configured to transmit information corresponding to the code image and the diagnostic result information to a server or an external terminal, wherein the biosensor cartridge comprises:

a circuit board including the connection terminal for electrically connecting to the biosensor diagnostic device;

a biosensor chip configured to:

detect a target material in the analysis specimen, the biosensor chip including a reactant configured to specifically react with or attach to the target material, and transmit a generated electrical signal to the connection terminal of the circuit board; and a housing configured to accommodate the circuit board and the biosensor chip, wherein the connection terminal is exposed outside of the housing, and wherein the biosensor cartridge is concavely recessed from an upper surface of the housing to accommodate the analysis specimen and forms an accommodating portion over a sensor area of the biosensor chip, wherein the accommodating portion includes a pattern structure configured to lower a surface energy of a surface of the accommodating portion for preventing adhesion or absorption.

16. The biosensor system of claim 15, wherein the biosensor chip comprises:

a plurality of channels;

a source electrode and a drain electrode connected with ends of each of the plurality of channels; and a gate electrode spaced apart from the source electrode and the drain electrode, the gate electrode being configured to apply a bias voltage to the analysis specimen.

17. The biosensor system of claim 16, wherein the plurality of channels include:

a first channel group including a first type of reactant for reacting with a first target material; and a second channel group including a second type of reactant for reacting with a second target material different from the first target material.

* * * * *